(12) United States Patent
Chan et al.

(10) Patent No.: US 8,907,057 B2
(45) Date of Patent: Dec. 9, 2014

(54) PEPTIDES THAT TARGET DORSAL ROOT GANGLION NEURONS

(71) Applicants: Lawrence Chan, Houston, TX (US); Hideto Kojima, Otsu Shiga (JP); Tomoya Terashima, Otsu (JP)

(72) Inventors: Lawrence Chan, Houston, TX (US); Hideto Kojima, Otsu Shiga (JP); Tomoya Terashima, Otsu (JP)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/175,387

(22) Filed: Feb. 7, 2014

(65) Prior Publication Data
US 2014/0227348 A1 Aug. 14, 2014

Related U.S. Application Data

(62) Division of application No. 12/864,895, filed as application No. PCT/US2009/032643 on Jan. 30, 2009, now Pat. No. 8,674,071.

(60) Provisional application No. 61/024,892, filed on Jan. 30, 2008.

(51) Int. Cl.
| | |
|---|---|
| *A61K 31/00* | (2006.01) |
| *C07K 4/00* | (2006.01) |
| *C12N 15/62* | (2006.01) |
| *A61K 45/06* | (2006.01) |
| *A61K 9/127* | (2006.01) |
| *A61K 38/08* | (2006.01) |
| *C07K 7/06* | (2006.01) |

(52) U.S. Cl.
CPC ............. *A61K 9/127* (2013.01); *A61K 45/06* (2013.01); *A61K 38/08* (2013.01); *C07K 7/06* (2013.01)
USPC ........................... 530/329; 514/1.1; 536/23.1

(58) Field of Classification Search
None
See application file for complete search history.

(56) References Cited

U.S. PATENT DOCUMENTS

2003/0119018 A1 6/2003 Omura et al. .................. 435/6

OTHER PUBLICATIONS

Extended European Search Report issued in European Application No. 09705757.4, mailed Nov. 28, 2011.
Goss, "The therapeutic potential of gene transfer for the treatment of peripheral neuropathies," *Expert Reviews in Molecular Medicine*, 9(8):1-19, 2007.
Koizumi et al., "Modified adenoviral vectors ablated for coxsackievirus-adenovirus receptor, α, integrin, and heparan sulfate binding reduce in vivo tissue transduction and toxicity," *Human Gene Therapy*, 17:264-279, 2006.
Waehler et al., "Engineering targeted viral vectors for gene therapy," *Nature Reviews Genetics*, 8(8):573-587, 2007.
Du et al., "Cyclic arg-gly-asp peptide-labeled liposomes for targeting drug therapy of hepatic fibrosis in rats," *Journal of Pharmacology and Experimental Therapeutics*, 322(2):560-568, 2007.
Federici et al., "A means for targeting therapeutics to peripheral nervous system neurons with axonal damage," *Neurosurgery*, 60(5): 911-918, 2007.
McGuire et al., "A library-selected, langerhans cell-targeting peptide enhances an immune response," *DNA And Cell Biology*, 23(11): 742-752, 2004.
Oi et al., "Isolation of specific peptides that home to dorsal root ganglion neurons in mice," *Neuroscience Letters*, 434(3): 266-272, 2008.
PCT International Preliminary Report on Patentability issued in International Application No. PCT/US2009/032643, mailed Aug. 12, 2010.
PCT International Search Report and Written Opinion issued in International Application No. PCT/US2009/032643, mailed Jun. 2, 2009.
Siniscalco et al., "Neuropathic pain: is the end of suffering starting in gene therapy?"*Current Drug Targets*, 6:75-80, 2005.
Storek et al., "Sensory neuron targeting by self-complementary AAV8 via lumbar puncture for chronic pain," *PNAS*, 105(3):1055-1060, 2008.
Terashima et al., "DRG-targeted helper-dependent adenoviruses mediate selective gene delivery for therapeutic rescue of sensory neuronopathies in mice," *J. Clin. Invest.*, 119(7): 2100-2112, 2009.
Wang et al., "Gene transfer to dorsal root ganglia by intrathecal injection: effects on regeneration of peripheral nerves," *Molecular Therapy*, 12(2): 314-320, 2005.

*Primary Examiner* — John Ulm
(74) *Attorney, Agent, or Firm* — Fulbright & Jaworski LLP

(57) ABSTRACT

The present invention concerns methods and compositions that employ peptides that target dorsal root ganglion (DRG) neurons. In particular, the peptides are used to target therapeutic agents, such as proteins, liposomes, or viral particles comprising therapeutic polynucleotides, to one or more peripheral neuropathies or neuropathic pain, for example. In particular cases, the peripheral neuropathies or neuropathic pain is caused directly or indirectly by DRG neuronopathy.

9 Claims, 46 Drawing Sheets

A

| fiber sequence | WF | DRG1 | DRG2 | DRG3 | KO1S* |
|---|---|---|---|---|---|
| HSPG (91-94) | KKTK (AAAAAAACCAAG) | GAGA (GGCGCCGGCGCC) | GAGA (GGCGCCGGCGCC) | GAGA (GGCGCCGGCGCC) | GAGA (GGCGCCGGCGCC) |
| CAR (408-409) | SP (TCTCCT) | EA (GAGGCC) | EA (GAGGCC) | EA (GAGGCC) | EA (GAGGCC) |
| Linker (6a.a.) (542-543) | none | GGSGGG | GGSGGG | GGSGGG | GGSGGG |
| Insert sequence (amino residue) | none | C-SPGARAF-C | C-DGPWRKM-C | C-FGQKASS-C | none |

```
              G   G   S   G   G   G   (linker)
HI loop:  ACA GGA GGT TCC GGA GGT GGA GGA
          542         BspEI site        543
```

DRG specific motif

Before infection

After infection to 293-cre cells cis-acting sequences : A repeat I  -TTTGGGCGTAACCG-
                      A repeat II -TTTGGCCATTTTCG-
consensus sequence :               -TTTGNNNNNNNNCG-

PEPTIDES THAT TARGET DORSAL ROOT GANGLION NEURONS

This application claims priority to U.S. patent application Ser. No. 12/864,895, filed Jul. 28, 2010, which was a US §371 application of PCT patent application Ser. No. PCT/US2009/032643, filed Jan. 30, 2009, which claims priority to U.S. Provisional Patent Application Ser. No. 61/024,892, filed Jan. 30, 2008, all of which applications are incorporated by reference herein in their entirety.

STATEMENT REGARDING FEDERALLY SPONSORED RESEARCH OR DEVELOPMENT

This invention was made with government support under National Institutes of Health Grant No. HL-51586 and HL-59314. The United States Government has certain rights in the invention.

TECHNICAL FIELD

The present invention generally concerns at least the fields of neurology, cell biology, molecular biology, and medicine. In particular, the present invention concerns the field of dorsal root ganglion biology and treatment of diseases related thereto.

BACKGROUND OF THE INVENTION

Phage display is a powerful technology to identify peptide sequence motifs that target a particular tissue or cell type in the body (Arap et al., 2002; Kolonin et al., 2004; Sidhu, 2001). Coupling such peptides to drugs and genes would enable their targeted delivery to specific cells and tissues in vitro and in vivo (Arap et al., 2002; Petty et al., 2007; Sergeeva et al., 2006; White et al., 2004). A commonly used platform is the combinatorial filamentous M13 phage library that displays short random peptides fused to a minor coat protein (pIII) (Sidhu, 2001), which can be used to isolate specific cell type-binding peptides by a procedure called biopanning (Petty et al., 2007). In the present invention, the technology has been applied to identify peptide motifs that recognize, and are specifically taken up by, neurons in the dorsal root ganglion (DRG) in mice as an exemplary model for humans. DRG neurons are target cells for the treatment of diseases of the peripheral sensory nervous system (Sghirlanzoni et al., 2005), in certain embodiments of the invention For instance, neuropathic pain is a common symptom in various disorders, including metabolic abnormalities, malignancies, physical injuries, toxins and poisons, and hereditary diseases (Sghirlanzoni et al., 2005), and is the cause of much morbidity and misery. Although various pharmaceutical agents, anesthetics, surgical operations, or procedures such as transcutaneous electrical nerve stimulation, have been used to treat the symptoms of neuropathic pain (Mendell and Sahenk, 2003), such palliative treatments are mostly non-targeted and of limited efficacy (Mendell and Sahenk, 2003). DRG neurons are the primary afferent neurons and can be classified into two broad groups: large and small neurons. Large neurons are thought to be involved mainly in proprioception, while most small neurons are involved in nociception (Zhang and Bao, 2006). Both neuronal populations have also been subclassified by biochemical and histological methods, such as lineage tracing or immunostaining of different markers (neurotransmitters, cell surface carbohydrates) (Dodd and Jessell, 1985; Kusunoki et al., 1991; Marmigere and Ernfors, 2007; Price and Flores, 2007). The present invention provides novel therapeutics and treatment methods for disease processes affecting the peripheral sensory nervous system (Goss, 2007).

Dysfunction of neurons in dorsal root ganglion (DRG) occurs in a variety of sensory neuronopathies (Sghirlanzoni et al., 2005; Kuntzer et al., 2004), including hereditary (Swanson et al., 1965), autoimmune (Malinow et al., 1986), nutritional (Montpetit et al., 1988), metabolic (Yasuda et al., 2003) and neoplastic diseases (Wanschitz et al., 1997). DRG neuronal disorders are associated with neuropathic pain, loss of sensation and sensory ataxia (Sghirlanzoni et al., 2005; Kuntzer et al., 2004). Delivery of neurotrophic factors can minimize neuronal damage in the DRG (Chattopadhyay et al., 2005; Wang et al., 2005; Pezet et al., 2006). However, neurotrophic polypeptides are susceptible to proteolytic degeneration and their therapeutic effects are short-lived; direct delivery of therapeutic genes proves to be more effective (Xu et al., 2003). Herpes simplex virus (Chattopadhyay et al., 2005) and poliovirus (Jackson et al., 2003) injected through subcutaneous or intramuscular routes are taken up by endocytosis at nerve terminals and travel via axonal transport to somas of DRG neurons. While the approach works in normal functioning nerves, the efficacy of such a strategy is greatly compromised under disease conditions. To circumvent this problem, direct injection into DRG neurons by microneurosurgery can be accomplished by the removal of a piece of vertebra to gain access to the DRG (Xu et al., 2003; Glatzel et al., 2000). Such a maneuver is, however, not practical for repeated injections, which is likely required for chronic disorders. In contrast, intrathecal (IT) injection is a far less invasive procedure that is used routinely in clinical practice (Wang et al., 2005). Nevertheless, DRGs are ensheathed in the dura and bathed in cerebrospinal fluid (CSF). Gene delivery vectors could disperse and be taken up elsewhere leading to complications, including meningitis (Driesse et al., 2000). To optimize the chance for successful DRG neuron delivery while minimizing undesired off-target effects, targeted gene delivery would be an ideal strategy for delivering genes to DRG neurons (Waehler et al., 2007).

Adenovirus (Ad) is an efficient gene transfer system in vitro as well as in vivo because of its capacity to infect both quiescent and proliferating cells, a broad spectrum of tissue transduction susceptibility and relative ease with which the vector can be produced in high titer. Helper-dependent adenoviral vector (HDAd) is the most advanced Ad, which is devoid of all viral coding sequences. The lack of potentially harmful Ad viral gene expression is associated with markedly reduced toxicity. HDAd-mediated in vivo gene delivery in rodents and nonhuman primates has been found to have an excellent safety profile and protracted transgene expression (Seiler et al., 2007; Brunetti-Pierri and Ng, 2008). Other advantages of HDAd are a large cloning capacity (up to 37 kb) and a greatly attenuated adaptive host immune response (Muruve et al., 2004). Thus, in specific embodiments the invention concerns HDAd as the backbone for the targeted vector for DRG neuron delivery.

The cellular tropism of Ad serotype 5 (Ad5) is determined by the cell-surface expression of primary attachment sites, the Coxsackie and Adenovirus receptor (CAR) (Bergelson et al., 1997; Tomko et al., 1997) and heparan sulfate proteoglycans (HSPG) (Dechecchi et al., 2001) and/or low-density lipoprotein receptor-related protein, and via the integrins, which act as secondary internalization receptors (Shayakhmetov et al., 2005; Koizumi et al., 2006; Parker et al., 2006). Cells deficient in the expression of these receptors are transduced at a greatly reduced efficiency. Little or no CAR is expressed by DRG neurons, which are poor targets for unmodified Ads (Hotta et al., 2003). Considerable effort has been expended on the generation of first generation Ads that target normally refractory tissues, as well as their retargeting to alternative cell-type specific receptors. Three major strategies have been employed in this respect: genetic modification of Ad capsid proteins, conjugation of adaptor proteins such as antibody, or bispecific fusion proteins, and chemical modification by polymers with targeting ligands (Waehler et al., 2007; Mizuguchi and Hayakawa, 2004). Genetic modification appears to the most popular of these approaches. This technology is particularly appealing for HDAd because capsid proteins of HDAd are supplied by the helper virus (HV). Armed with a library of targeting HVs, one can produce HDAds that potentially target any tissue by applying the specific HV at the final amplification. To date, despite the many potential advantages of HDAd, targeting HDAd by genetic modification has been limited to the introduction of peptide ligands into the HI loop (Biermann et al., 2001) or replacement of fiber gene with that of a different Ad serotype (Wang et al., 2005).

BRIEF SUMMARY OF THE INVENTION

In general, the present invention concerns methods and compositions for the treatment of medical conditions that involve dorsal root ganglion neurons, including specific subtypes thereof. In specific aspects of the invention, the present invention concerns methods and compositions for treating peripheral neuropathies, as well as neuropathic pain, for example. In particular embodiments, the present invention concerns a novel strategy for the treatment of sensory neuronopathies, for example using a sensory neuron-targeted helper-dependent adenoviral vector In certain embodiments, there are peptides that home to mouse dorsal root ganglion (DRG). These peptides were obtained from an exemplary phage library expressing random 7-mer peptides fused to a minor coat protein (pIII) of the M13 phage. An in vitro biopanning procedure yielded 113 phage plaques after five cycles of enrichment by incubation with isolated DRG neurons and two cycles of subtraction by exposure to irrelevant cell lines. Analyses of the sequences of this collection identified three peptide clones that occurred repeatedly during the biopanning procedure.

Phage-antibody staining revealed that the three exemplary peptides bound to DRG neurons of different sizes. The peptides were injected as individual GST-peptide fusion proteins into the subarachnoid space of mice and there was the appearance of immunoreactive GST in the cytosol of DRG neurons with a similar size distribution as that observed in vitro, indicating that the GST-peptide fusion proteins were recognized and taken up by different DRG neurons in vivo. The identification of homing peptide sequences provides a powerful tool for future studies on DRG neuronal function in vitro and in vivo, and opens up the possibility of neuron-specific drug and gene delivery in the treatment of diseases affecting DRG neurons.

In additional embodiments, an enzyme gene was delivered to mice with the enzyme deficiency (hexB-ko). These mice have peripheral neuropathy and abnormal functional tests, although they are known in the art for having mental retardation but not peripheral neuropathy (the inventors tested if they had neuropathy because it can objectively be measured). The treatment significantly ameliorated the functional deficiencies. The peptide was engineered to the coat of HDAd, and there was homing to DRG neurons. Therefore, the inventors used the re-targeted HDAd to deliver the hexB to the subarachnoid space and successfully targeted the DRG neurons. Wildtype Ad delivery did not work.

In one embodiment of the invention, there is a method of targeting a dorsal root ganglion neuron in an individual, comprising the step of delivering to the individual one or more peptides from Table 2, or a derivative thereof. In a specific embodiment, the peptide is selected from the group consisting of SPGARAF (SEQ ID NO:1), DGPWRKM (SEQ ID NO:2), FGQKASS (SEQ ID NO:3), or a mixture thereof. In an additional embodiment, the individual has a peripheral neuropathy or neuropathic pain.

In certain embodiments of the present invention, methods and compositions are employed to engineer fiber-modified HDAd and demonstrate the efficacy of HDAd bearing DRG neuron-specific targeting peptide (Oi et al., 2008) to correct a genetic deficiency and reverse its associated sensory deficit in a mouse model (Sango et al., 1995; Sango et al., 2002). Targeting ligands were introduced into the fiber of HV lacking the CAR and HSPG binding sites and showed that HV lacking primary attachment sites has markedly impaired ability to transduce 293 cells and DRG neurons in vitro, and that addition of DRG targeting peptide ligands efficiently retargets HV to DRG neurons. In addition, using Cre-expressing HDAd amplified in the presence of fiber-modified HVs, there was high efficiency DRG neuron targeting in vivo following intrathecal injection into ROSA-GFP transgenic mice. Finally, efficacy of the targeting strategy to correct a genetic deficiency in DRG neurons was demonstrated, reversing specifically the peripheral sensory nervous system dysfunction in mice with β-hexosaminidase deficiency. In certain embodiments of the invention, targeted HDAd gene therapy for DRG neuron disorders is useful.

In one embodiment of the invention, there is an isolated peptide of SEQ ID NO:1, SEQ ID NO:2, SEQ ID NO:3, or a modified peptide having one, two, or three conservative substitutions compared to SEQ ID NO:1, SEQ ID NO:2, or SEQ ID NO:3, respectively, or a combination thereof. In a specific embodiment, the peptide is comprised in a pharmaceutically acceptable excipient. In a particular embodiment, the peptide is linked to a protein, such as a therapeutic protein, or a liposome. In certain aspects, the protein is present on the surface of a helper-dependent adenoviral particle. In particular cases, the viral particle is defined as further comprising a therapeutic polynucleotide.

In another embodiment of the invention, there is a method of targeting a dorsal root ganglion (DRG) neuron in an individual, comprising the step of delivering to the individual an effective amount of one or more peptides of the invention. In a specific embodiment, the individual has DRG neuronopathy. In certain cases, the DRG neuronopathy results in a neuropathy. In particular cases, the individual has pain, hyperalgesia, hypoalgesia, or ataxia. In specific embodiments, the helper-dependent adenoviral particle is delivered intrathecally.

In a certain embodiment of the invention, there is a method of treating a DRG neuronopathy in an individual, comprising the step of delivering to the individual an effective amount of a therapeutic agent linked to one or more peptides of the invention or an effective amount of a liposome comprising a therapeutic agent, wherein the is liposome linked to one or more peptides of the invention.

In an additional embodiment, there is a method of treating a DRG neuronopathy in an individual, comprising the step of delivering to the individual an effective amount of one or more peptides of the invention. In certain cases, the DRG neuronopathy results in a neuropathy. In particular cases, the individual has pain, hyperalgesia, hypoalgesia, or ataxia. In specific embodiments, the helper-dependent adenoviral particle is delivered intrathecally. In certain cases, the invention is utilized for sensory neuropathy and/or sensory neuronopathy.

In certain embodiments, there is one or more polynucleotides that encodes a peptide or a peptide and protein of the invention. In certain aspects, the peptide is linked covalently to the protein, and in particular cases the peptide and protein are fused as a proteinaceous molecule and/or are encoded by a single polynucleotide.

In particular embodiments of the invention, a therapeutic protein is NGF, EGF, FGF, BDNF, IGF1, CTNF, PDNF, VAD, DEVD, NGN1, NGN2, NGN3, RUNX3, or a signal peptide. In specific embodiments, a therapeutic polynucleotide that encodes a therapeutic protein is selected from the group consisting of NGF, EGF, FGF, BDNF, IGF1, CTNF, PDNF, VAD, DEVD, NGN1, NGN2, NGN3, RUNX3, IL-10, anti-TNFα, EPO, or prepro-β endorphin.

In specific aspects of the invention, DRG neuronopathy results in a neuropathy selected from the group consisting of neuropathies associated with metabolic disease, hereditary disease, neoplasm, infectious disease, injury, or in autoimmune disease. In a specific embodiment, the individual has pain, hyperalgesia, hypoalgesia, or ataxia. In a particular embodiment, the helper-dependent adenoviral particle is delivered intrathecally.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
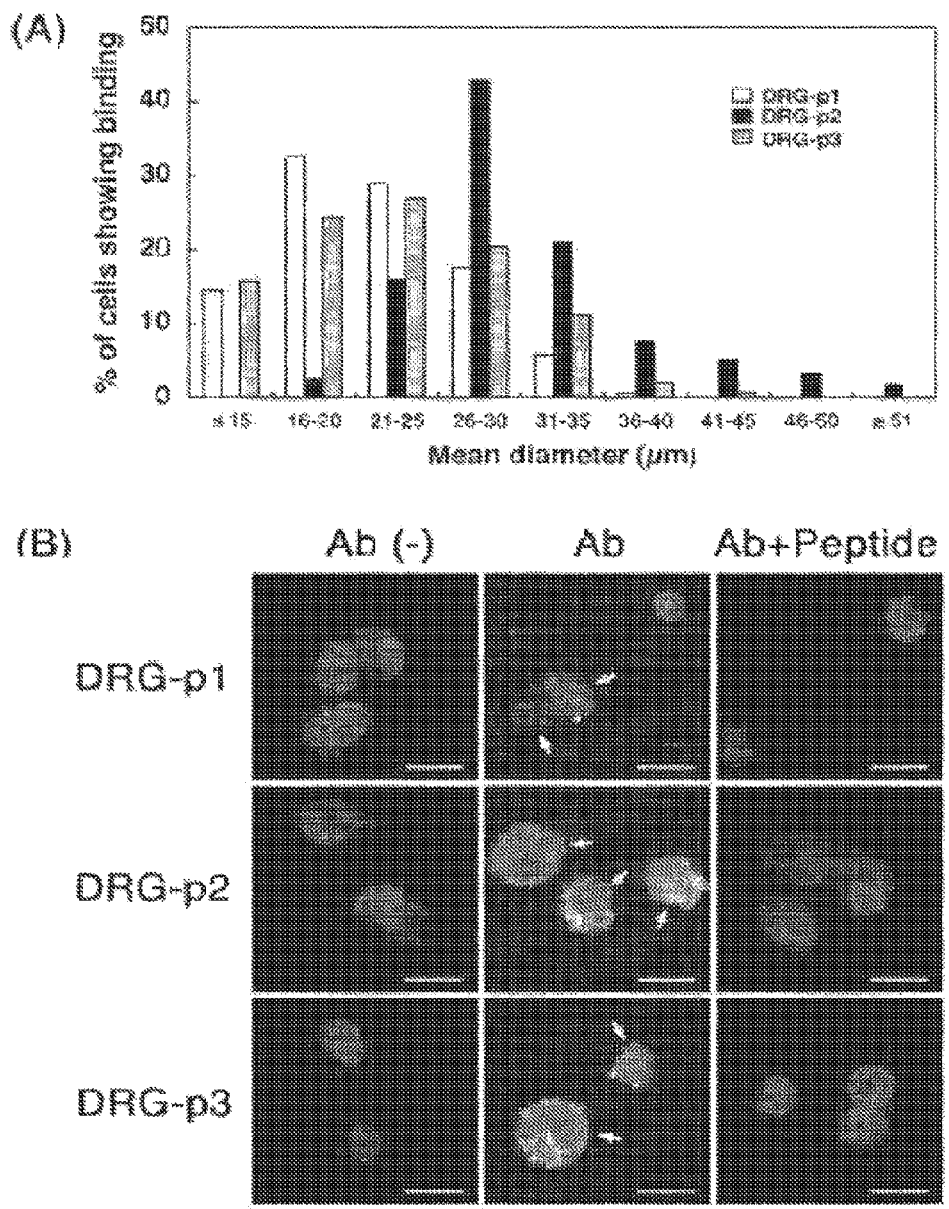
FIG. 1 shows binding of 3 different phages to cultured-DRG neurons. The cells were analyzed by a confocal laser-scanning microscopy. (A) Cell size distribution of the DRG neurons positive for DRG-p1, DRG-p2 or DRG-p3. (B) Bindings of the 3 different phage clones to mouse DRG neurons. Positive reactions stained with anti-fd antibody (Ab) are green. Ab (−) is without antibody and Ab+ peptide is antibody plus peptides ($10^{-4}$ M) corresponding to each phage. Nuclei were stained with PI (red). Bars=20 µm.

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

I. General Embodiments of the Present Invention

In the present invention, the inventors have isolated three exemplary peptides that recognize specific, defined sizes of DRG neurons. These peptides are useful for targeting DRG neurons and for therapeutics for diseases involving specific subtypes of DRG neurons, for example.

In certain aspects, the invention concerns methods and compositions that target therapeutic genes to dorsal root ganglion (DRG) neurons for the treatment of DRG neuronopathy, a common disorder for which there is no satisfactory treatment. The inventors inserted DRG homing-peptides to the fiber of helper virus (HV), an adenovirus (Ad) that is detargeted for binding to Coxsackie and Ad receptor and heparan sulfate proteoglycans, and used it to generate DRG-targeting helper-dependent Ad (HDAd). Intrathecal injection of the HDAd produced a 100-fold higher transduction of DRG neurons and a markedly attenuated inflammatory response as compared to unmodified HDAd. The inventors tested this treatment strategy in a disease model by injecting HDAd-β-hexosaminidase β-subunit to ⊕-hexosaminidase-deficient mice. Delivery of the targeting HDAd reinstated neuron-specific β-hexosaminidase production, reversed the gangliosidosis, and ameliorated peripheral sensory dysfunction. The development of DRG neuron-targeted HDAd with proven efficacy is useful for the treatment of sensory neuronopathies of diverse etiologies.

II. Peptides of the Invention

In certain embodiments, the present invention concerns novel compositions comprising at least one peptide. In one embodiment of the invention, there is an isolated peptide from Table 2, for example of SEQ ID NO:1, SEQ ID NO:2, SEQ ID NO:3, or a modified peptide thereof having one, two, three, four, or more conservative substitutions compared to SEQ ID NO:1, SEQ ID NO:2, or SEQ ID NO:3, respectively; or a combination thereof.

As used herein, a peptide is a composition of from about 3 to about 25 amino acids, although in specific embodiments the peptide is between 5 and 20 amino acids, 5 and 15 amino acids, 5 and 10 amino acids, 6 and 10 amino acids, 7 and 10 amino acids, 8 and 10 amino acids, 9 and 10 amino acids, 5 and 9 amino acids, 6 and 9 amino acids, 7 and 9 amino acids, 8 and 9 amino acids, 5 and 8 amino acids, 6 and 8 amino acids, 7 and 8 amino acids, 5 and 7 amino acids, or 6 and 7 amino acids in length. In specific cases, the peptide is 5 amino acids in length, 6 amino acids in length, 7 amino acids in length, 8 amino acids in length, 9 amino acids in length, 10 amino acids in length, 11 amino acids in length, and so forth.

The peptide may comprise at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In particular embodiments, the peptide may comprise some identity to, such as be derived from, a peptide of Table 2, and such a composition may be referred to a derivative of a peptide of Table 2. For example, a peptide that has one, two, or three amino acids that are different from any of the peptides of Table 2 (including SPGARAF, DGPWRKM, and FGQKASS, for example) may be employed. Biologically functional equivalents of the peptides of Table 2 may be employed and are thus defined herein as those peptides wherein selected amino acids may be substituted. Functional activity of these biologically functional equivalent peptides includes the ability to home to dorsal root ganglion neurons, and this may be tested in accordance with the exemplary methods of the invention provided herein.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/ or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and/or arginine (4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein, for example. As detailed therein, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (0.4); proline (−0.5±1); alanine (0.5); histidine (0.5); cysteine (1.0); methionine (1.3); valine (1.5); leucine (1.8); isoleucine (1.8); tyrosine (2.3); phenylalanine (2.5); tryptophan (3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

In certain embodiments, the peptide is biocompatible that produces no significant untoward effects when applied to, or administered to, a given organism according to the methods and amounts described herein. Organisms include, but are not limited to, mammals, including humans, dogs, cats, horses, cows, pigs, goats, and sheep. Such untoward or undesirable effects are those such as significant toxicity or adverse immunological reactions. In preferred embodiments, biocompatible peptide-containing compositions will generally be peptides essentially free from toxins, pathogens and harmful immunogens.

Peptides may be made by any technique known to those of skill in the art, including the expression of proteins and their further processing or the chemical synthesis of peptides, for example. In certain embodiments a peptide may be purified or isolated. Generally, "purified" will refer to a specific peptide composition that has been subjected to fractionation to remove various other proteins, polypeptides, or peptides, and which composition substantially retains its activity, as may be assessed, for example, by an assay as would be known to one of ordinary skill in the art for the specific or desired peptide.

III. Utilization of the Peptides of the Invention

In particular embodiments of the invention, one or more peptides from Table 2, including SPGARAF, DGPWRKM, or FGQKASS, for example, are administered to an individual in need thereof. In particular cases, the individual has, is suspected of having, or is at risk for having one or more peripheral neuropathies or neuropathic pain, for example.

Peripheral neuropathy as used herein refers to damage to the nerves of the peripheral nervous system, and this may result from diseases of the nerve or as a side effect of a systemic illness, for example. Peripheral neuropathies can present and have origin in a variety of ways, and in some cases the nerve is affected, whereas in other cases the neuromuscular junction is affected. Peripheral neuropathies may either be symmetrical and generalized or focal and multifocal, and such a presentation is useful in determining the cause of the peripheral nerve disease.

Exemplary causes of peripheral neuropathy include, for example, genetic diseases, such as Friedreich's ataxia or Charcot-Marie-Tooth syndrome, for example; metabolic/endocrine disorders, such as diabetes mellitus, chronic renal failure, porphyria, amyloidosis, liver failure, or hypothyroidism, for example; toxic origins, such as alcoholism, drugs (vincristine, phenytoin, isoniazid), organic metals, and/or heavy metals, for example; inflammatory diseases, such as Guillain-Barré syndrome, systemic lupus erythematosis, leprosy, or Sjögren's syndrome; vitamin deficiency states, such as vitamin B12, vitamin A, vitamin E, or thiamin, for example; or other causes, such as malignant disease, HIV, radiation, or chemotherapy.

Generalized peripheral neuropathies are symmetrical, affecting the peripheral nervous system in its entirety. They may occur because of a variety of systematic illnesses and disease processes. These types of neuropathies are further subdivided into several categories, including distal axonopathies, myelinopathies, or neuronopathies. Distal axonopathies stem from some metabolic or toxic derangement of neurons, such as from metabolic diseases including diabetes, renal failure, deficiency syndromes (malnutrition or alcoholism, for example), or the effects of toxins or drugs. Myelinopathies are the result of a primary attack on myelin causing an acute failure of impulse conduction, such as from acute inflammatory demyelinating polyneuropathy (AIDP; aka Guillain-Barré syndrome), chronic inflammatory demyelinating polyneuropathy (CIDP), genetic metabolic disorders (e.g., leukodystrophy), or toxins. Finally, neuronopathies are caused by destruction of peripheral nervous system neurons, and they may be caused by motor neuron diseases, sensory neuronopathies (e.g., Herpes zoster), toxins or autonomic dysfunction, for example, although in some cases they are caused by neurotoxins, such as vincristine, a chemotherapy agent.

The methods and compositions of the present invention may also be utilized for treating neuropathic pain. Neuropathic pain is chronic pain that often is accompanied by tissue injury, wherein the nerve fibers themselves might be damaged, dysfunctional, or injured, for example. Such damaged nerve fibers send incorrect signals to other pain centers, therefore, the effect of a nerve fiber injury includes a change in nerve function both at the site of injury and areas around the injury.

Neuropathic pain usually appears to have no obvious cause and often responds poorly to conventional pain treatment, sometimes getting worse instead of better with time. For some people, it can lead to serious disability. One exemplary type of neuropathic pain is phantom limb syndrome, following removal of a limb. Other common causes of neuropathic pain include alcoholism; back, leg, and hip problems; chemotherapy; diabetes; facial nerve problems; HIV infection or AIDS; multiple sclerosis; shingles; and/or spinal surgery, for example. Symptoms of neuropathic pain include numbness, shooting pain, burning pain, and/or tingling.

IV. Medical Conditions Affecting DRG Neurons

In particular embodiments of the invention, there are methods and compositions suitable for use in the treatment of medical conditions that affect DRG neurons. In a specific embodiment, the medical condition is a DRG neuronopathy.

In specific embodiments, the medical condition includes neuropathic pain, which can occur among patients with various metabolic and inflammatory disorders, including diabetic neuropathy for individuals that suffer neuropathic pain caused by sensory neuron dysfunction. In specific embodiments, individuals with ganglionopathies, for example, caused by autoimmune diseases or drug toxicities, may utilize the present invention for neuropathic pain. In specific embodiments, treatment of these and other sensory neuronopathies by intrathecal DRG-targeting HDAd that express neurotrophic factors or analgesic peptides is a useful application of the invention.

V. Therapeutic Proteins and Polynucleotides Encoding Same

In some embodiments, the present invention comprises therapeutic proteins, for example linked to DRG neuron-targeting peptide, or polynucleotides encoding the therapeutic proteins. Exemplary therapeutic proteins include those that ameliorate at least in part a DRG neuronopathy or at least one clinical symptom caused directly or indirectly thereby. Exemplary agents include growth factors, transcriptional factors, signal peptides, or enzymes.

Exemplary genes and gene products that may be considered therapeutic in certain embodiments of the invention include the following: growth factors such as NGF, EGF, FGF, BDNF, IGF1, CTNF, PDNF, or anti-apoptotic peptides such as VAD, DEVD, or transcription factors such as NGN1, NGN2, NGN3, RUNX3, or signal peptides. Thus, in certain embodiments, NGF, EGF, FGF, BDNF, IGF1, CTNF, PDNF, VAD, DEVD, NGN1, NGN2, NGN3, RUNX3, IL-10, anti-TNFα, EPO, or prepro-β endorphin are employed.

Additional exemplary genes and/or proteins for use in the invention for therapeutic benefit in conjunction with the peptide include the following known in the art: self-complementary AAV8 via lumbar puncture (for example) (Storek et al., 2008); knockdown of $Na_v1.3$, $Na_v1.8$, VGCC, NMDA receptors and opioid receptors, spinal opioid receptors, P2X receptors and c-fos (Sinaiscalco et al. (2005); and NGF (including using liposomes) (Wang et al., 2005). Additional references exhibiting use of liposomes for peptide targeting include Du et al. (2007), McGuire et al. (2004), and U.S. Pat. No. 7,238,665, which is incorporated by reference herein in its entirety.

VI. Pharmaceutical Preparations

Pharmaceutical compositions of the present invention comprise an effective amount of one or more peptides that target dorsal root ganglions and, in some cases, an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one peptide will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The peptide may utilize different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The peptide may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more of the peptides and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the peptide may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the peptide is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the peptide may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,737,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound peptide may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VII. Kits of the Invention

Any of the peptide compositions described herein may be comprised in a kit. In a non-limiting example, an additional agent may also be comprised in a kit. The kits will thus comprise, in suitable container means, a peptide and, in some cases, an additional agent of the present invention.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the peptide and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition, in which case the container means may itself be a syringe, pipette, and/or other such like apparatus from which the formulation may be applied to an infected area of the body, injected into an animal, and/or even applied to and/or mixed with the other components of the kit.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation of DRG Neuron-Binding Peptides

Adult C57BL/6 mice aged 8-12 weeks were used in all experiments, and were housed in an animal room with a 12-h light and 12-h dark cycle in an illumination-controlled facility. All experiments were conducted with the approval of the Research Center for Animal Life Science at Shiga University of Medical Science. A phage library expressing random 7-mer peptides fused to a minor coat protein (pIII) of the M13 phage, at a complexity of about $1.3 \times 10^9$ independent sequences, was purchased from New England BioLabs (The Ph.D.-C7C Phage display Peptide Library kit, Beverly, Mass.). Rabbit anti-fd bacteriophage antibody was purchased from Sigma Aldrich Corp. (St. Louis, Mo.). Donkey FITC-labeled anti-rabbit IgG was purchased from Chemicon (Temecula, Calif.) The three synthetic peptides, DRG1: SPGARAF (SEQ ID NO:1), DRG2: DGPWRKM (SEQ ID NO:2), DRG3: FGQKASS (SEQ ID NO:3), were supplied from Yanaihara Institute (Shizuoka, Japan). Various cell lines; mouse neuroblastoma cells (Neuro-2a), human embryonic kidney epithelial cells (HEK-293), opossum kidney cells, were purchased from American Type Culture Collection (Manassas, VA) for use in a subtractive panning protocol. These cultured cells were maintained in DMEM medium with 10% fetal calf serum (FCS, Invitrogen, Gaithersburg, MD) with antibiotics at 37° C. in 5% $CO_2$.

Mouse DRG neurons were isolated from lumbar segments L1-L5 of C57BL/6 mice using an enzymatic procedure described previously (Terashima et al., 2005). The neurons were purified with 30% percoll (MP Biomedicals, Solon, Ohio), washed twice with Ham's F12 medium supplemented with 10% fetal calf serum (Invitrogen), and then plated on poly-L-lysine (Sigma)-coated 10 cm dishes for in vitro biopanning or on 8 well Lab-Tek Chamber Slides (NUNC, Naperville, Ill.) for in vitro phage binding. The cells were allowed to attach at 37° C. for 12 hours in 5% $CO_2$.

The in vitro phage display library screening protocols described by Hong et al. (2000) were employed with minor modifications. Briefly, after washing isolated DRG neurons three times with PBS, the culture medium was changed FCS-free DMEM medium. Then, $1 \times 10^{10}$ plaque-forming units (pfu) of the M13 phage library were added to isolated DRG neurons ($1 \times 10^6$/well), and incubated at 37° C. in 5% $CO_2$ for 10 min. After washing three times, the bound phages were recovered by grinding the cells with protease inhibitor in DMEM medium. Aliquots were diluted appropriately and infected E. coli ER2738, mixed with Agarose Top, and incubated in LB/IPTG/X-gal plates at 37° C. overnight. After titrating plaque forming units, phages in the aliquot were further amplified by infecting E. coli with them in a shaker at 37° C. for 4.5 h. Phages from the E. coli were purified, and $1\times10^{10-11}$ pfu were added to isolated DRG neurons again. In all, five such rounds of screening with DRG neurons were carried out. To select more specific phages for DRG neurons, a subtractive panning protocol (Nicklin et al., 2000) against irrelevant cell lines (Neuro-2a, HEK-293, and opossum kidney cells from American Type Culture Collection, Manassas, Va.) was performed twice. These cultured cells were maintained in DMEM medium with 10% fetal calf serum (FCS, Invitrogen, Gaithersburg, Md.) with antibiotics at 37° C. in 5% $CO_2$. To avoid the selection of polystyrene and poly-L-lysine-specific peptides, a subtractive panning protocol against poly-L-lysine culture dishes was also performed twice (Adey et al., 1995).

In vitro phage binding to DRG neurons was carried out on cultured neuronsin 8-well chamber slides following three washes with PBS to clear the cell surface ($n=1\times10^5$ cells/well). Cells were incubated at 37° C. for 1 h with either the three selected phages or control library phage at $2\times10^9$ pfu/well ($1\times10^{10}$ pfu/ml), with or without synthetic peptides ($10^{-4}$ or $10^{-6}$ M; DRG1: SPGARAF (SEQ ID NO:1), DRG2: DGPWRKM (SEQ ID NO:2), DRG3: FGQKASS (SEQ ID NO:3), which had 7 amino-acid sequences homologous to the selected phages. Subsequently, unbounded phages and/or peptides were removed by washing the chamber slides three times with PBS. To detect phages bound to the cells, the cultured cells were fixed with 4% paraformaldehyde and incubated for 1 h with rabbit anti-fd antibody (diluted 1:1000 in PBS with 3% donkey serum, Sigma Aldrich Corp., St. Louis, MO), washed three times with PBS, and subsequently incubated with FITC-conjugated donkey anti-rabbit IgG diluted 1:1000 for 1 h (Chemicon, Temecula, CA). After three washes, the cells were treated with propidium iodine (PI) for nuclear staining, and then observed under a confocal laser-scanning microscope (LSM510, Carl Zeiss, Jena, Germany). For quantitative analysis, ten randomly selected fields in each well were photographed and diameters were measured (long and short) of the cells positive for phage immunostaining and PI staining. The mean cell size was calculated as the mean of the long and short diameter, and cell-size differences were evaluated in different groups.

To evaluate their binding to DRG cells in vivo, GST fusion proteins of three selected peptides were synthesized using the pGEX4T-1 vector kit (Amersham, Piscataway, N.J.) according to the manufacturer's instructions. Briefly, oligonucleotides for C-DRG1-C, C-DRG2-C, and C-DRG3-C were synthesized cloned into the pGEX4T-1 vector, and transformed in E. coli. The synthesized GST-fusion proteins were pull down by Glutathione Sepharose 4B (Amersham), and purified. The purities and reactions to anti-GST antibodies (Amersham) were confirmed by gel-electrophoresis stained by Coomassie Blue and anti-GST immunoblotting.

Under intraperitoneal pentobarbiturate anesthesia (0.1mg/g BW), 10 µl (500 µg/ml) of purified GST-fusion proteins (GST-DRG1, GST-DRG2, GST-DRG3, or GST alone) were injected into the subarachnoid space of 8-week-old female C57BL/6 mice (n=3 each). After 1 h, the mice were sacrificed and transcardially perfused with cold saline followed by 4% paraformaldehyde, 0.5% glutaraldehyde and 0.3% picric acid in 0.1 M PBS (pH 7.4). The L5 DRGs were then isolated and cut sectioned (10 µm) for fluorescence immunohistochemistry. After blocking with 10% horse serum, the sections were incubated overnight at 4° C. with goat anti-GST antibody (Amersham) diluted 1:1000 and rabbit anti-neurofilament L (NF-L, non-phosphorylated form, Chemicon, Temecula, Calif.) antibody diluted 1:100 in PBST. The sections were incubated for 1 h with Alexa Fluor 488-labeled anti-goat IgG and Alexa Fluor 555-labeled anti-rabbit IgG (Molecular Probes, Eugene, Oreg.) at room temperature, mounted with VECTASHIELD mounting medium containing 4',6-diamidino-2-phenylindole (DAPI) (Vector Laboratories Inc., Burlingame, Calif.), and observed under a fluorescence microscope (Axioplan 2 imaging and Axiocam, Carl Zeiss, Jena, Germany). For quantitative analysis, the inventors took pictures of randomly selected fields and measured diameters (long and short) of the cells positive for GST, NF-L and DAPI. The mean cell size was calculated as the mean of the long and short diameters, and cell-size differences were evaluated in the three different groups.

BLAST (see the National Center for Biotechnology Information's website) searches of the mouse database with the phage peptide sequences were carried out to identify homologies with proteins of interest, including neuronal growth factors, cytokines, hormones, and cell adhesion molecules.

Data were analyzed by ANOVA for multiple comparisons and shown as mean±SD. Significance was assigned at $P<0.05$.

The inventors used an in vitro biopanning protocol and isolated 113 phage plaques in five rounds of screening with DRG neurons and four rounds of negative selection, two against irrelevant cell lines, and two against poly-L-lysine-coated culture plates. Of the 113 plaques, five displayed an identical 7-amino acid sequence (DRG1), four shared another 7-mer sequence (DRG2), and three others displayed a third shared sequence (DRG3); 17 other sequences (DRG4 to DRG20) were each shared by two different plaques. The sequences of the other 67 clones were all different from one another (Table 2).

| Name | Sequence | Counts | SEQ ID NO |
|---|---|---|---|
| DRG1 | SPGARAF | 5 | 1 |
| DRG2 | DGPWRKM | 4 | 2 |
| DRG3 | FGQKASS | 3 | 3 |
| DRG4 | TGFQSGS | 2 | 4 |
| DRG5 | DSSRTRL | 2 | 5 |
| DRG6 | DFIRTQA | 2 | 6 |
| DRG7 | LKHTNEA | 2 | 7 |
| DRG8 | QGAHNNN | 2 | 8 |
| DRG9 | NPHKAPN | 2 | 9 |
| DRG10 | NPSLQAP | 2 | 10 |
| DRG11 | PPWSSPK | 2 | 11 |
| DRG12 | AQSHNKL | 2 | 12 |
| DRG13 | LPTSKKM | 2 | 13 |
| DRG14 | NHLKNPA | 2 | 14 |
| DRG15 | TFSIGEK | 2 | 15 |
| DRG16 | QAIQNST | 2 | 16 |
| DRG17 | HNTNAQH | 2 | 17 |

| Name | Sequence | Counts | SEQ ID NO |
|---|---|---|---|
| DRG18 | TPSLPQT | 2 | 18 |
| DRG19 | NMPTQRS | 2 | 19 |
| DRG20 | PVRSPAV | 2 | 20 |
| DRG21 | SSQAPQS | 1 | 21 |
| DRG22 | DAQKNMN | 1 | 22 |
| DRG23 | GLQLSQT | 1 | 23 |
| DRG24 | SASNTQY | 1 | 24 |
| DRG25 | EGHLVSQ | 1 | 25 |
| DRG26 | SDPGNYM | 1 | 26 |
| DRG27 | ALDNVPH | 1 | 27 |
| DRG28 | PTKQHAK | 1 | 28 |
| DRG29 | TELQRHN | 1 | 29 |
| DRG30 | HTTSSLY | 1 | 30 |
| DRG31 | MGQNLRF | 1 | 31 |
| DRG32 | NLQLAPD | 1 | 32 |
| DRG33 | SSFRGAT | 1 | 33 |
| DRG34 | LHKSHLL | 1 | 34 |
| DRG35 | APPELRL | 1 | 35 |
| DRG36 | HRTIASG | 1 | 36 |
| DRG37 | TESIGDK | 1 | 37 |
| DRG38 | APDETER | 1 | 38 |
| DRG39 | KGLPPGH | 1 | 39 |
| DRG40 | PSGTPSY | 1 | 40 |
| DRG41 | SNRSPLM | 1 | 41 |
| DRG42 | TIGQSYR | 1 | 42 |
| DRG43 | SPTEGTP | 1 | 43 |
| DRG44 | PLSGAPW | 1 | 44 |
| DRG45 | DAPTHMH | 1 | 45 |
| DRG46 | TDFRSRV | 1 | 46 |
| DRG47 | LVLPPLA | 1 | 47 |
| DRG48 | SSSPARL | 1 | 48 |
| DRG49 | TATNTRT | 1 | 49 |
| DRG50 | DGAGTWV | 1 | 50 |
| DRG51 | EKHLAPR | 1 | 51 |
| DRG52 | PLTPLGF | 1 | 52 |
| DRG53 | MTPFMGS | 1 | 53 |
| DRG54 | DSPGWPH | 1 | 54 |
| DRG55 | GERHSLT | 1 | 55 |
| DRG56 | TTAVALR | 1 | 56 |
| DRG57 | NGLHVQR | 1 | 57 |
| DRG58 | TLSPRSA | 1 | 58 |
| DRG59 | HTGPFGL | 1 | 59 |
| DRG60 | LSTSSKK | 1 | 60 |
| DRG61 | TPPSPRT | 1 | 61 |
| DRG62 | PALSHST | 1 | 62 |
| DRG63 | TPSWSKK | 1 | 63 |
| DRG64 | STPAVPP | 1 | 64 |
| DRG65 | NLNAHHK | 1 | 65 |
| DRG66 | QHQKQGY | 1 | 66 |
| DRG67 | NKTTNIM | 1 | 67 |
| DRG68 | TSASLSS | 1 | 68 |
| DRG69 | RSSPPNT | 1 | 69 |
| DRG70 | SPPRPTG | 1 | 70 |
| DRG71 | VNTPERH | 1 | 71 |
| DRG72 | TPQYPKL | 1 | 72 |
| DRG73 | PTLLPHQ | 1 | 73 |
| DRG74 | NNANYRL | 1 | 74 |
| DRG75 | GPHFHQS | 1 | 75 |
| DRG76 | PAMNSVK | 1 | 76 |
| DRG77 | GTTPTST | 1 | 77 |
| DRG78 | HNSTRGS | 1 | 78 |
| DRG79 | DDSGPLR | 1 | 79 |
| DRG80 | NMHPTAT | 1 | 80 |
| DRG81 | HQNWRHT | 1 | 81 |
| DRG82 | PSTKYHS | 1 | 82 |
| DRG83 | PLRLAHQ | 1 | 83 |
| DRG84 | QMPGNNL | 1 | 84 |
| DRG85 | LATPLRN | 1 | 85 |
| DRG86 | LNGLKAA | 1 | 86 |
| DRG87 | TVSSHRA | 1 | 87 |

The three phage clones, DRG1, DRG2 and DRG3, were further analyzed since these 3 clones appeared at least three times by binding to DRG neurons in vitro; these phage clones were designated DRG-p1, DRG-p2 and DRG-p3, respectively.

The binding of the 3 different clones to isolated DRG neurons maintained in culture was analyzed (FIG. 1). DRG-p1 bound to 38% of the DRG neurons (83/219), DRG-p2 to 43% (100/231), and DRG-p3 to 29% (69/235), while the control phage library bound to 8% (45/539) of the DRG neurons. The addition of peptides ($10^{-4}$ M) with identical amino-acid sequences blocked the staining with anti-phage antibodies by 97% for DRG-p1, 94% for DRG-p2, and 94% for DRG-p3, while adding 10-6 M peptide blocked staining by 47% for DRG-p1, 54% for DRG-p2, and 53% for DRG-p3, as compared with similarly bound cultures stained with antibody alone. As each peptide was only capable of competing for the binding of the phage with an identical 7-amino acid sequence (data not shown), the phage-neuron binding was concluded to be sequence specific (FIG. 1B).

The cell size distribution of the DRG neurons that bound to individual phage clones was then analyzed. Interestingly, DRG-p1 and DRG-p3 staining occurred mainly in small-sized neurons with a mean diameter of 22.0±5.3 μm (for DRG-p1) and 23.2±6.7 μm (for DRG-3p), while DRG-p2 staining occurred mainly in large-sized neurons with a mean diameter of 30.9±7.0 μm (FIG. 1A). There was a significant difference between the mean diameter of the cells positive for DRG-p1 and that for DRG-p2 ($p<0.001$), and of the cells positive for DRG-p2 and for DRG-p3 ($p<0.001$), but no difference between the cells positive for DRG-p1 and DRG-P3.

Figure 2:
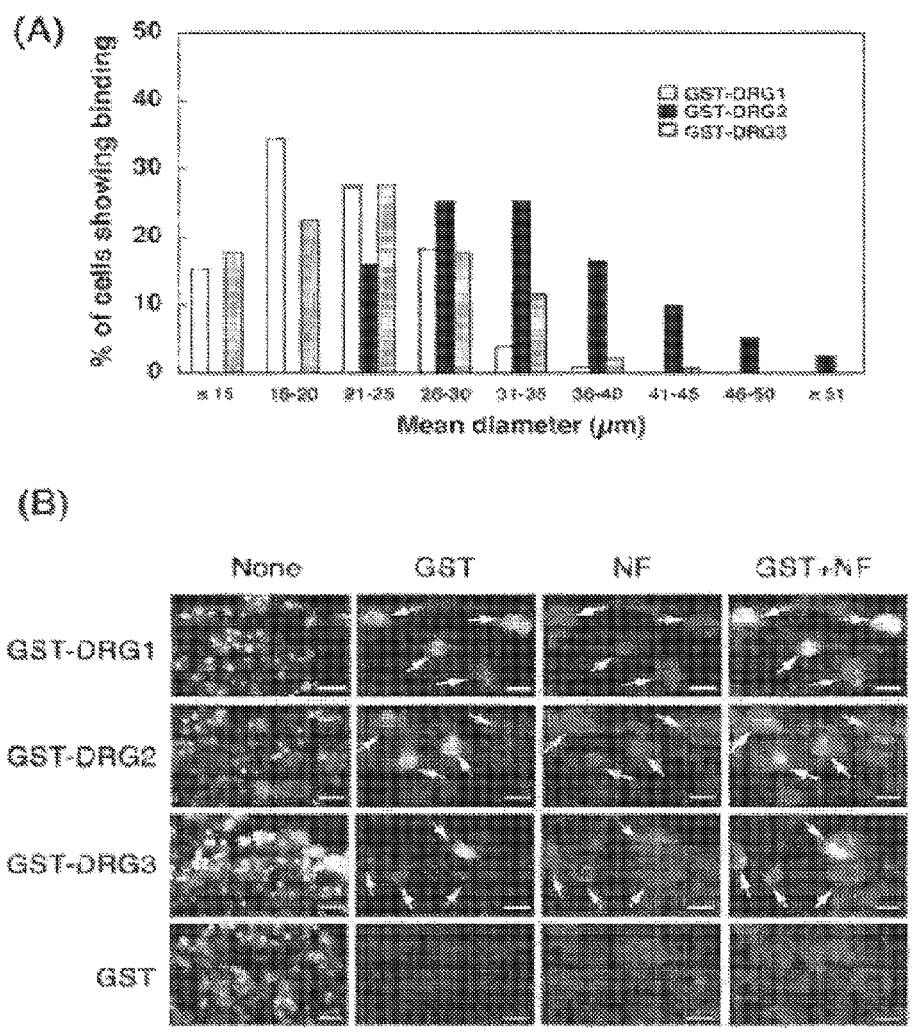
FIG. 2 demonstrates fluorescence microscopy of in vivo binding of GST-peptide-fusion proteins to DRG neurons. (A) Cell size distribution of the DRG neurons positive for GST-DRG1, GST-DRG2 or GST-DRG3. (B) Double immunofluorescence staining of DRG-neurons with anti-GST (green) and anti-neurofilament L (NF-L, non-phosphorylated form, red). Nuclei were stained with DAPI (blue). None indicates no primary antibody. Arrows indicated the cells positive for both GST and NF-L. Bars=20 µm.

To examine the DRG-targeting of peptides in vivo, individual GST-peptide-fusion proteins (5 μg each) or GST alone were injected into the subarachnoid space in C57BL/6 mice, the DRGs were isolated, and they were used in anti-GST immunostaining to detect the neuron-associated GST-peptide-fusion proteins (see Materials and Methods). Additionally, the inventors double-immunostained the cells against anti-neurofilament L (NF-L, non-phosphorylated form) antibodies, and found that essentially all (99%) cells positive for GST-peptide-fusion proteins were also positive for neurofilament (FIG. 2B). In DRG cells from control mice injected with GST, no anti-GST staining was observed (FIG. 2B). Furthermore, 39% (368/949) of the NF-L-positive neurons were positive for GST-DRG1, 25% (214/848) for GST-DRG2, and 14% (147/1081) for GST-DRG3. Cell size analysis showed that GST-DRG1- and GST-DRG3-positive cells were mainly small-sized neurons, whereas GST-DRG2-positive cells were mainly large-sized DRG neurons (FIG. 2B). The mean diameter of the cells positive for GST-DRG1 was 21.6±5.2 GST-DRG2 33.5±7.4 μm, and GST-DRG3 22.7±6.6 μm. There was a significant difference in mean diameter between GST-DRG1-positive cells and GST-DRG2-positive cells ($p<0.001$), and between GST-DRG2-positive and GST-DRG3-positive cells ($p<0.001$), but no size difference between GST-DRG1-positive and GST-DRG3-positive cells. Therefore, the cell size specificity of the three different peptides in phages in vitro (FIG. 1A) was confirmed by the in vivo-binding experiment. Moreover, as most of the GST-positive immunoreactivity was detected in the cytoplasm of the DRG neurons (FIG. 2B), and as anti-GST antibodies used in this experiment were specific for recombinant GST-peptides fusion proteins synthesized in E. coli, and did not react with mouse endogenous GST, the bound GST-peptide-fusion proteins appear to have been internalized into the cytosol of the targeted neurons. In contrast, the GST immunoreactivities in the central nervous system (brain and spinal cord) was examined, and there was no specific staining. Possible endogenous candidates in the mouse protein database were searched for that might bind to the DRG, "receptors" for the three 7-amino acid peptides, and the same DRG1 7-amino-acid sequence in the extra cellular matrix protein TM14 (NP_077199.2) was found (de Vega et al., 2007). However, 6 out the 7 amino acids were located in the putative signal peptide and not in the putative binding domain in TM14. The mouse neuronal differentiation-related protein (NDRP, NP_001096649.1) has the same 7-amino acid sequence as that in DRG2 (Kato et al., 2000). NDRP is expressed in the sensory neuronal system including in DRG neurons, though the current knowledge of its function is limited. There were no peptide sequences in the database similar to that in DRG3.

The inventors used the in vitro screening of a C7C peptide library displayed on M13 filamentous phages against isolated mouse DRG neurons to isolate phage-clones that encompassed three different 7-amino acid peptides that displayed specific binding for these neurons in vitro. Immunohistochemical analysis following the injection of GST-peptide fusion proteins in vivo demonstrated that the three peptides bind to DRG neurons with different sizes; furthermore, these fusion proteins were internalized into the cytoplasm of the targeted neurons.

The Ph.D.-C7C Phage display Peptide Library kit expresses random 7-amino acid peptides fused to the minor coat protein (pIII) of the M13 phage. By sequence analysis, only 113 phage plaques were represented in the bound peptide, consistent with a very efficient selection process (Table 2). The final binding studies allowed identification of three phages (DRG1, DRG2, or DRG3) that occurred repeatedly. In specific embodiments of the invention, the efficient identification of these clones was the result of multiple rounds of positive and negative selection using the biopanning protocol (Liang et al., 2006), although in specific cases some of the other 84 clones (Table 2) are true DRG-binding peptide-phages. The three clones that were analyzed further showed interesting specificities to the targeted neurons: DRG-p1 and DRG-p3 to small-sized neurons and DRG-p2 to large-sized neurons. Moreover, the size specificity of target neurons for individual peptides was confirmed by in vivo binding experiments: GST-DRG1 and GST-DRG3 recognized small-sized neurons, and GST-DRG2 recognized large-sized neurons. Since both DRG1 and DRG3 recognized small sized neurons, two peptide ligands might bind to the same cell populations. Therefore, double staining was performed of isolated DRG neurons after the incubation with DRG-p1 and GST-DRG3 by antibodies against phage and GST, respectively. Double positive staining was obtained in 51% of DRG-p1-positive neurons, and was in 71% of GST-DRG3-positive neurons, respectively. The result indicates that both DRG1 and DRG3 recognized different targeting molecules, but may bind to the same cell populations in specific subpopulations in small-sized neurons. Histologically, mammalian sensory DRG neurons have been classified into two major types: large-light and small-dark cells on the basis of their staining characteristics seen under light microscopy (Lawson, 2002). Clinically, peripheral sensory neuropathy (including neuronopathy) has been classified into two types based on fiber size: large fiber sensory neuropathy and small fiber sensory neuropathy (Mendell and Sahennk, 2003; Sghirlanzoni et al., 2005). The symptom typically found in large fiber sensory neuropathy is an ataxic gait, and that in small fiber sensory neuropathy is mainly pain (Mendell and Sahennk, 2003; Sghirlanzoni et al., 2005). Neuronal size is directly related to axonal characteristics (Lawson, 2002; Lawson and Waddell, 1991; Sghirlanzoni et al., 2005). Thus, each targeting motif included in DRG1, DRG2, DRG3, and, potentially, in some of the other 84 peptides sequences, may be useful tools for pathophysiological analysis such as a cell-identification marker, or for the generation of gene-delivery constructs for sensory neuropathies (Liu et al., 2005; Mata et al., 2006; Sah, 2006).

The inventors also tried to determine the size of the targeted protein using the whole homogenate of DRG tissues from mice, and found some specific bands by Western blotting analysis. Since those bands are proteins targeted by the peptides, in specific aspects of the invention, they are further clarified.

In conclusion, the inventors have used in vitro phage display technology to isolate and identify three different exemplary peptides that bind to DRG neurons in vitro and in vivo. It was further shown that the peptides recognize neurons of two different sizes. In further studies the binding proteins and their receptors are identified. Nevertheless, the three DRG neuron-specific peptides are useful for the generation of molecular delivery systems targeting different DRG neurons in vivo.

Example 2

Production of Fiber-Modified Helper Virus

Figure 3:
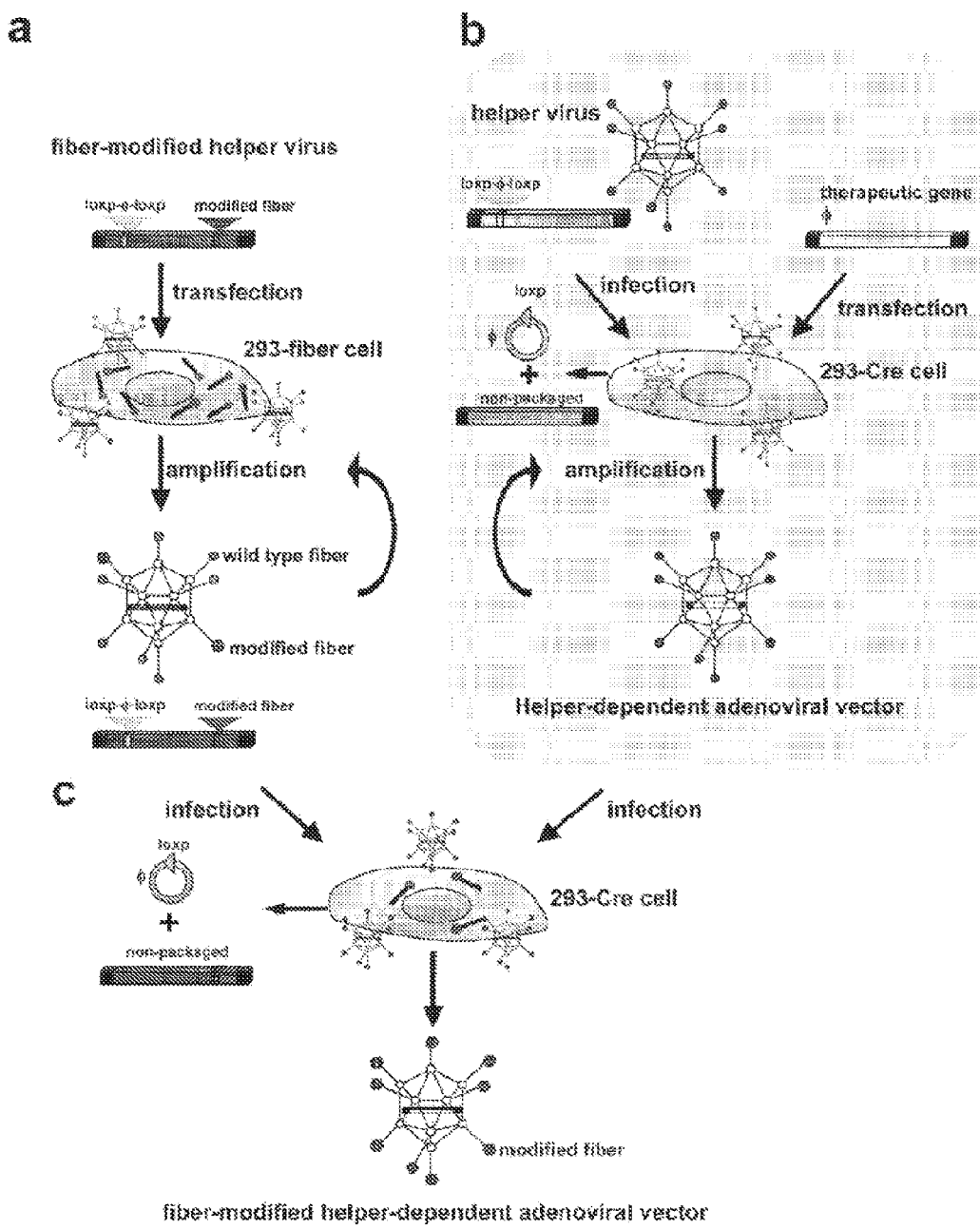
FIG. 3 Strategy for construction of fiber-modified helper-dependent adenoviral vectors (HDAd). (a) Construction of fiber-modified helper virus (HV). HV is a first generation E1-deleted Ad vector containing the packaging signal flanked by loxP sequences. This HV provides all of the components necessary for replication and packaging of HDAd genome in trans, but cannot be packaged by itself upon coinfection of Cre expressing packaging cells with HDAd due to the excision of the packaging signal for HV. The first step to construct targeted HDAd is to produce fiber-modified HV. In the approach, HV is detargeted by ablation of primary docking sites, CAR and HSPG, and then adding a targeting peptide ligand. HV produced by transfection contains no primary docking sites to 293 cells for infection and is unable to reinfect for amplification. To overcome this problem, 293 cells were established expressing Ad serotype 5 wild type fiber (293-fiber). HV produced on 293-fiber has both wild type and modified fiber and can infect 293 cells effectively while the modified fiber genome is maintained. But, the wild type fiber can be removed by infection of 293 cells. (b) Construction of HDAd. The genome of HDAd contains only essential cis-acting elements (inverted terminal repeats for replication and the packaging signal) and is introduced into packaging cells expressing Cre by transfection. By coinfection with HV containing wild type fiber, HDAd genome is packaged into Ad particles. HV continues to provide all of the components necessary for replication and packaging, but the HV genome cannot be packaged. (c) Generation of fiber-modified HDAd. Final step of production of fiber-modified HDAd is coinfection of 293Cre with HDAd and HV made on 293-fiber cells. HDAd genome is packaged into viral particles encoded by HV genome, which results in HDAd capsids containing modified fiber.
Figure 4:
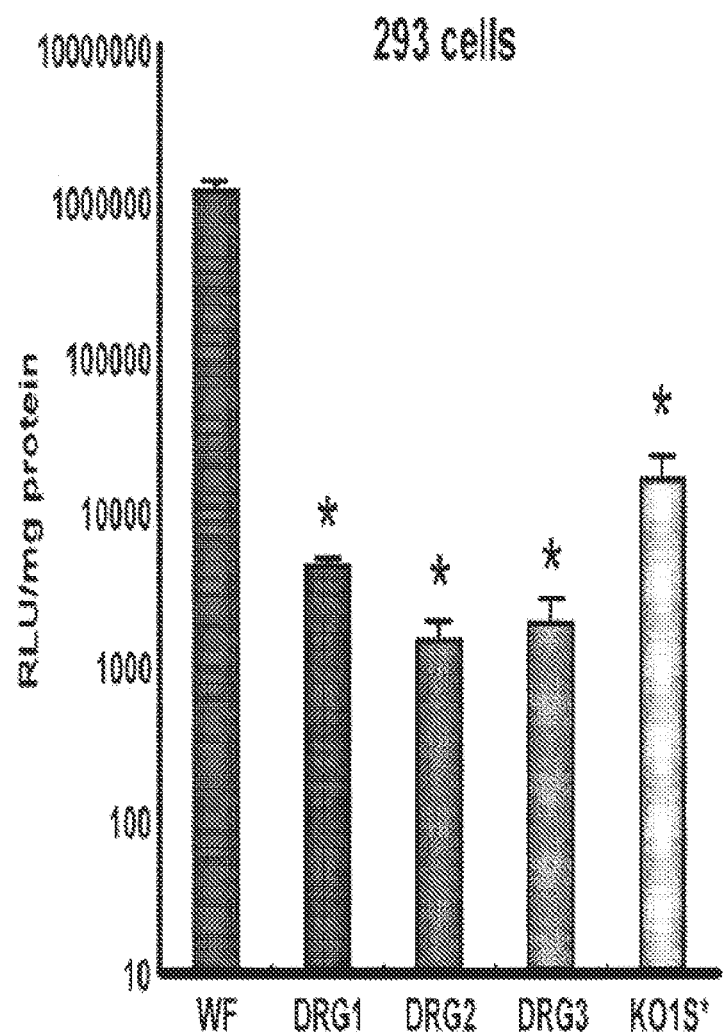
FIG. 4 Transduction of DRG neurons by fiber-modified helper virus (HV). (a) Features of modified fiber proteins. WF contained Ad5 wild type fiber. All other HVs had the KO1S* backbone which has the BspEI site (blue letters) within 6 amino acids linker (fourth row; SEQ ID NO:6) and modification of heparan sulfate proteoglycan (HSPG) binding site (KKTK; corresponding sequence is SEQ ID NO:104) to GAGA (second row; corresponding sequence is SEQ ID NO:105) and Coxsackie and Adenovirus receptor (CAR) binding site (SP) to EA (third row). DRG homing peptides (DRG1, DRG2 and DRG3) were inserted into the BspEI site in the HI loop of fiber protein (bottom), with insert sequences corresponding to SEQ ID NO:107, SEQ ID NO:108, and SEQ ID NO:109, respectively. Numbers show the position of amino acid in the fiber protein. (b) Luciferase activity in 293 cells. 293 cells were infected with HVs at 1,000 viral particles (vp)/cell and were harvested 24 hours after infection for luciferase assay. Results are expressed as relative light units (RLU) per mg protein (n=6). (c) Luciferase activity in HV infected DRG neurons. Primary DRG neurons were infected and luciferase activity was determined as described in (b). (d) LacZ expression in nervous system. $1 \times 10^8$ vp of fiber modified HVs were injected into C57BL/6 mice through subarachnoid space at lumbar level. Mice were sacrificed 5 days after HV injection and stained for LacZ expression. Upper panels show whole DRG tissues with nerves and lower panels showed brain and spinal cord. Scale bar, 2 mm. Arrows in the WF group indicate X-gal positive areas at nerve portion in upper panel and at dorsal intermediate sulcus of spinal cord in lower panel. Arrowhead shows the position of vector injection. (e) Luciferase activities in nervous systems. $1 \times 10^8$ vp of fiber-modified HVs were injected into C57BL/6 mice as described in (d) and neuronal tissues were harvested 5 days after injection. (f) Long term LacZ expression in DRG. Mice were treated with $1 \times 10^8$ vp of HV-WF or -DRG1 and were sacrificed at various time. LacZ mRNA in DRG was quantified by real time RT-PCR and normalized to β-actin mRNA. Data are expressed as relative to the LacZ mRNA in the HV-WF group at day 60. *$P<0.001$, $P<0.01$ and *$P<0.05$ vs. WF group.
Figure 4:
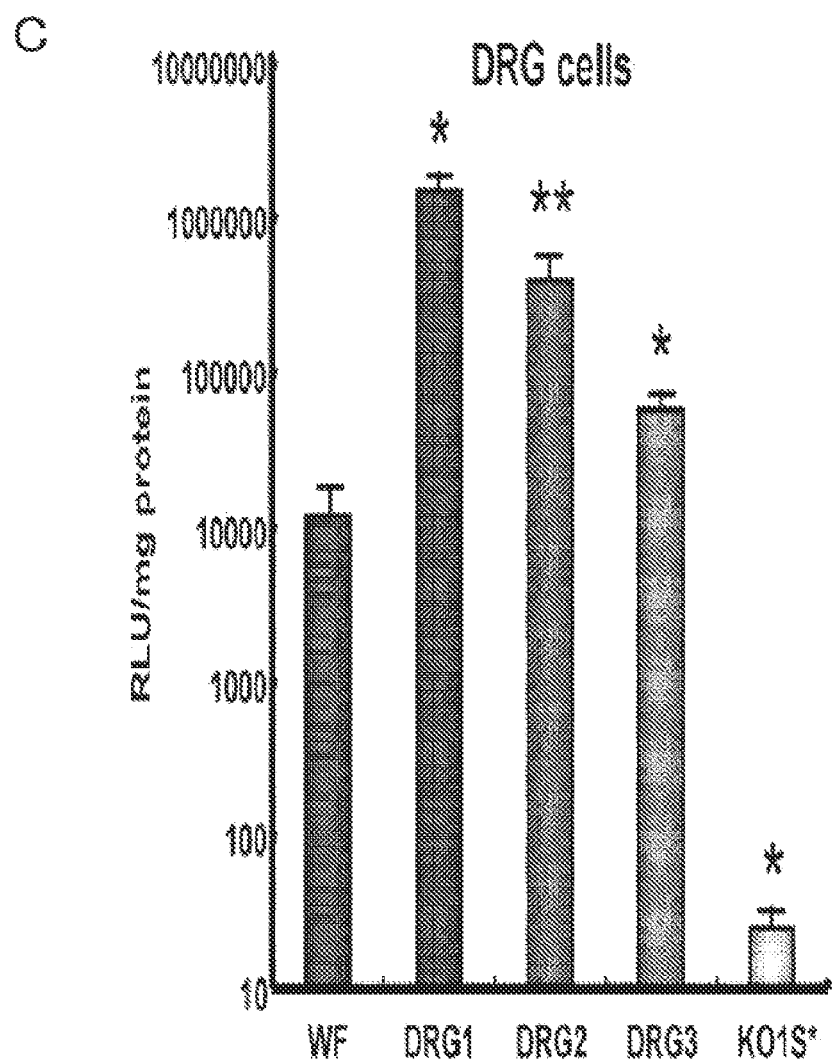
Figure 4:
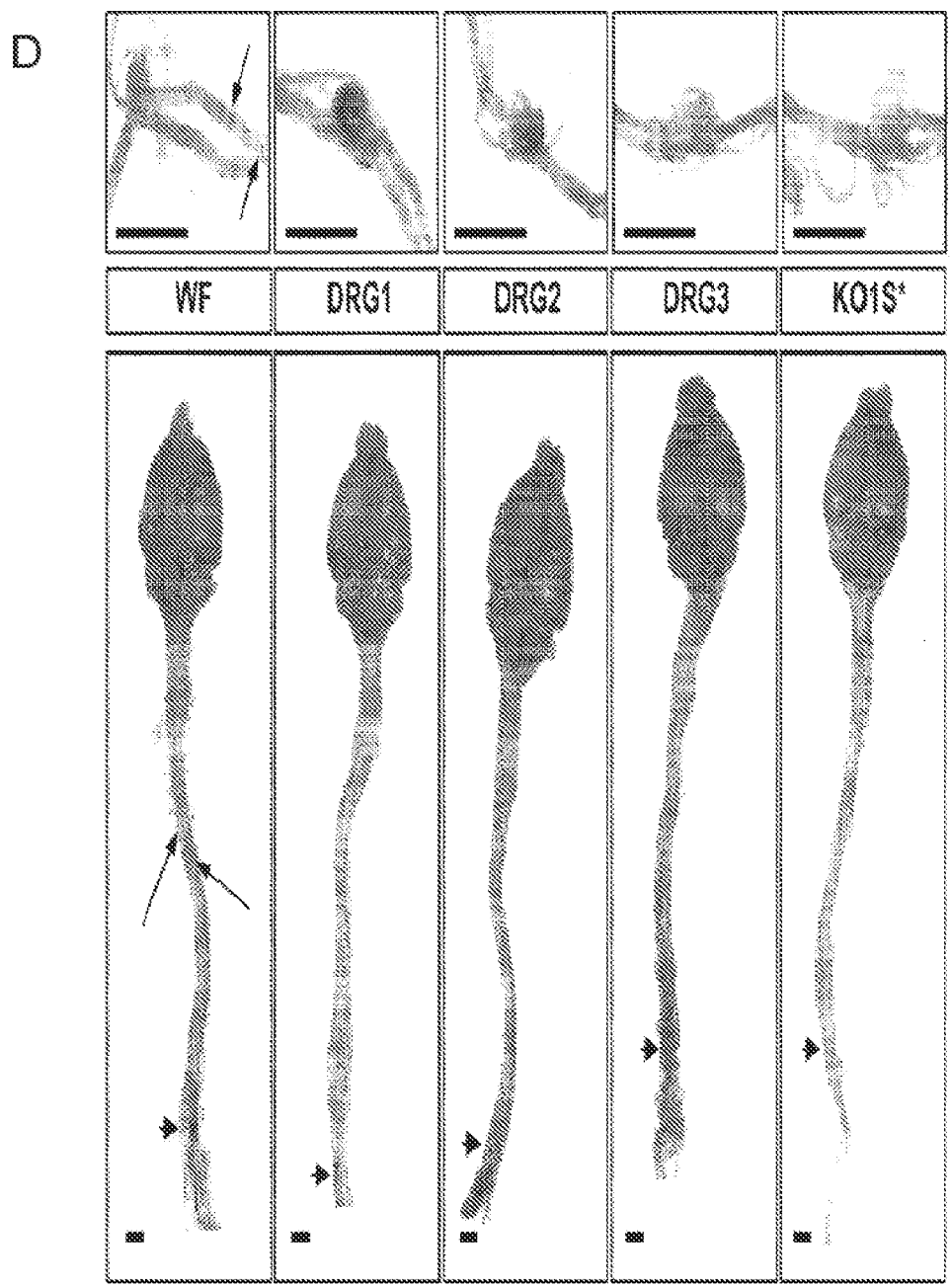
Figure 4:
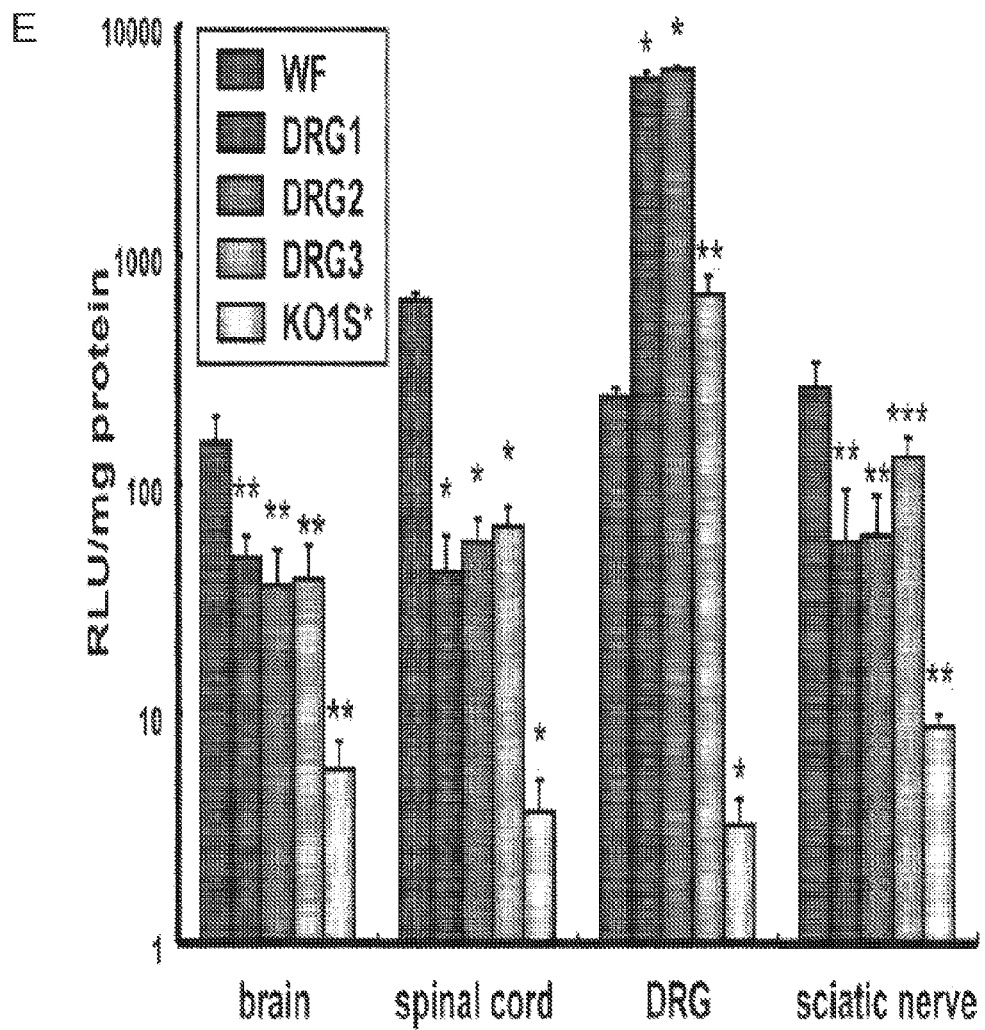
Figure 4:
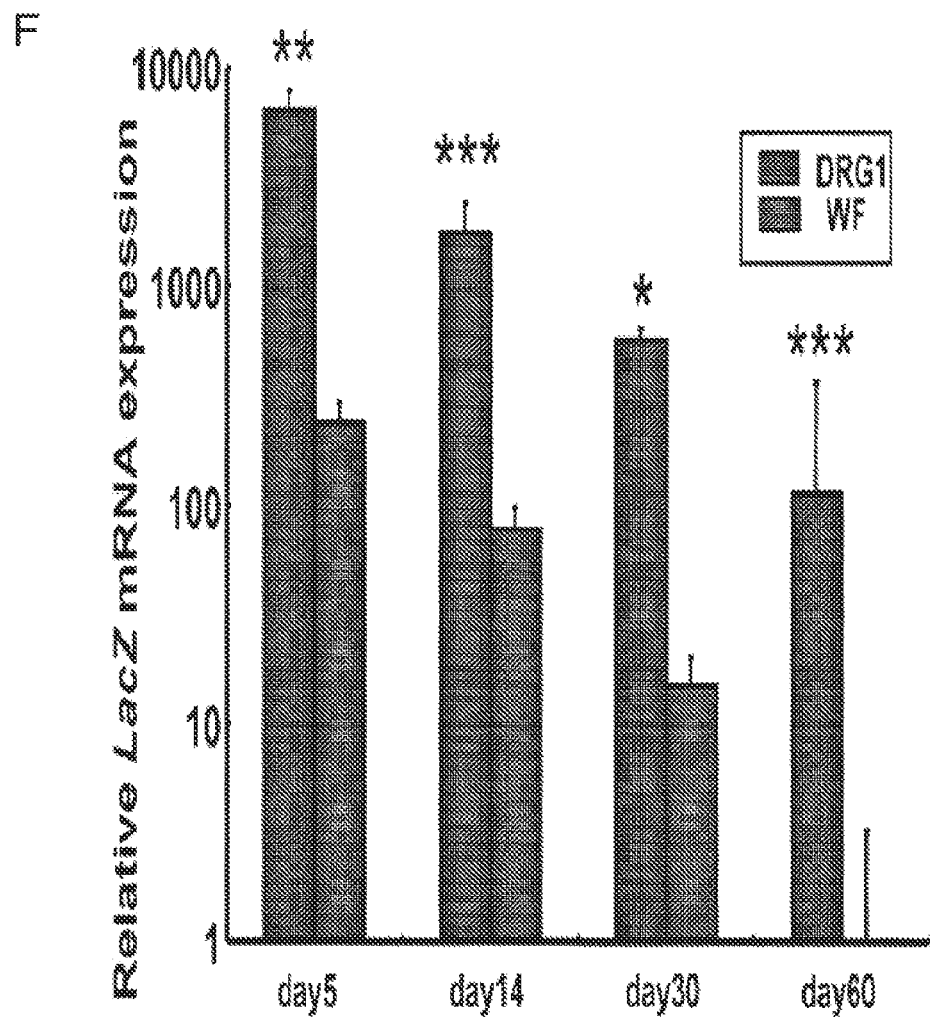
Figure 5:
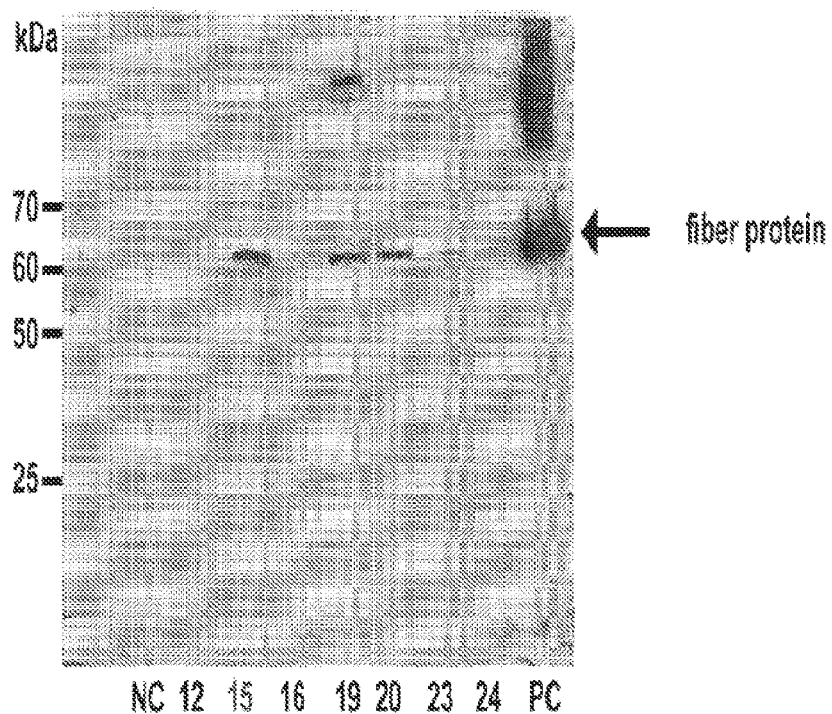
FIG. 5 Generation of 293-fiber cell and structure of fiber-modified helper viruses (HVs). (a) Immunoblot analysis of 293 cells expressing adenovirus serotype 5 (Ad5) fiber protein. (upper panel). Upper panel: The 62 kDa band corresponds to the monomer of fiber protein. High molecular size bands are the predicted trimer of the fiber protein. The clone 15 highlighted in red was further characterized for complementation of wild type fiber for HV amplification. Lower panel: structure of lentiviral vector expressing Ad5 wild type fiber. (b) Nucleotide sequence of the HI loop in fiber-modified HV genome. DNA was extracted from purified HV and characterized by DNA sequence analysis. *Nucleotide change from T to G as a result of subcloning targeting motif into the BspEI site. Illustrated sequence for HV-KO1S* is SEQ ID NO:111; for HV-DRG1 is SEQ ID NO:112; for HV-DRG2 is SEQ ID NO:113; and for HV-DRG3 is SEQ ID NO:114.
Figure 5:
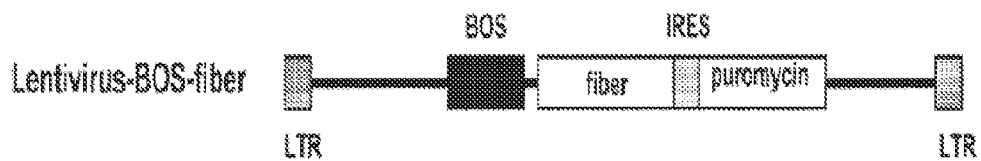
Figure 5:
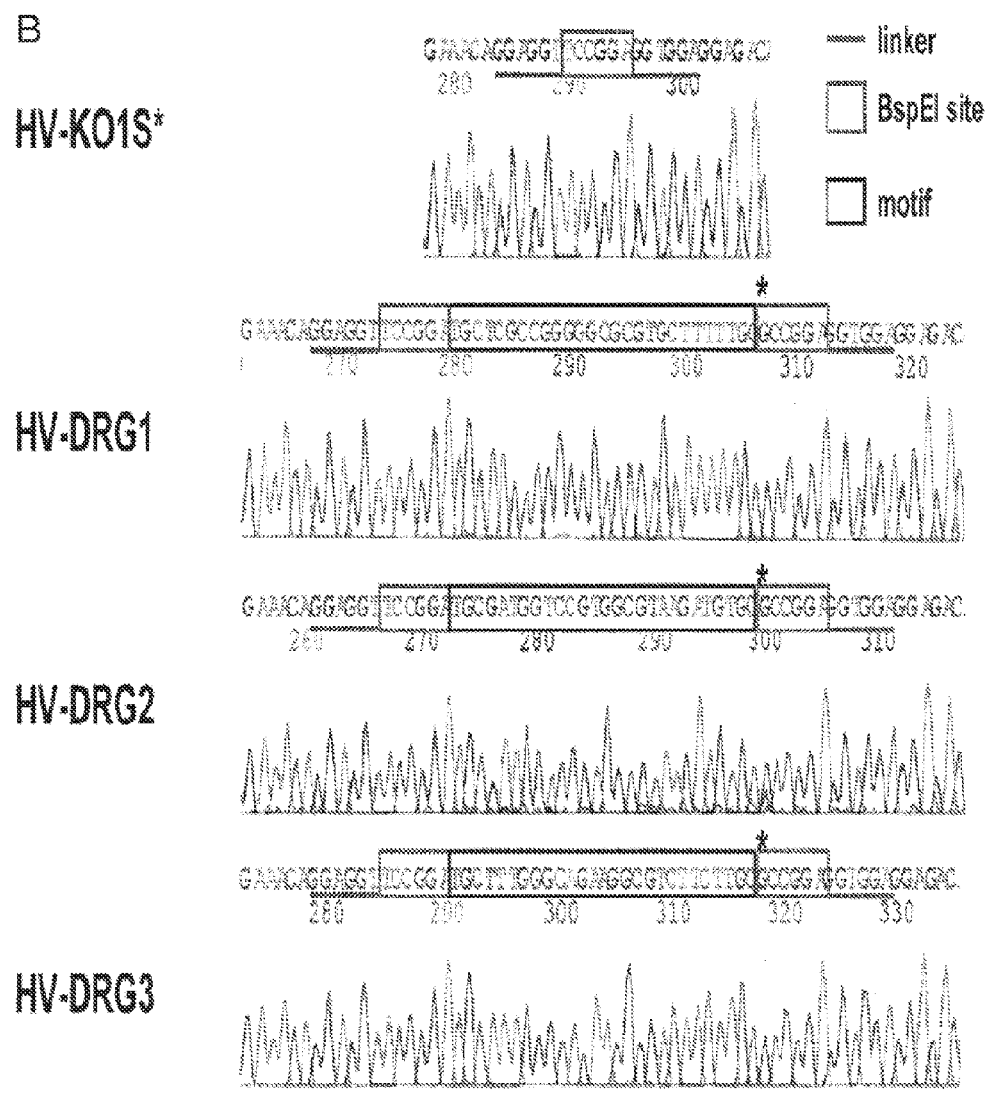

In a routine method for HDAd production, all necessary factors for packaging HDAd genome are supplied in trans by a helper virus (HV), a first generation Ad. In this scheme, HDAd that expresses the gene of interest (e.g., a therapeutic transgene) can be made to target specific organ or cell type simply by using an appropriate HV at the final amplification (Kim et al., 2001). There is no need to engineer a new HDAd (FIG. 3), in specific embodiments. To produce targeted HV, the inventors first attenuated the natural tropism by ablating the binding sites of Ad5 fiber to its canonical primary docking receptors, CAR and HSPG (Kritz et al., 2007). To circumvent the very poor infectivity of KO1S* mutant Ad (which lack both binding sites) toward 293 cells, 293 cells were established expressing Ad5 wild type fiber (293-fiber) to incorporate wild type fiber into the capsid of HV-KO1S* (FIG. 3a). Fiber-modified HV generated on 293-fiber had both wild type fiber and modified fiber encoded by HV genome. A total of 5 HVs were generated: [i] HV-WF containing wild type fiber: [ii] HV-KO1S* a detargeted HV; and [iii, iv, & v] 3 HVs on a HV-KO1S* backbone that contains individual DRG-targeting motifs, DRG1, DRG2 and DRG3 (FIG. 4a) (Oi et al., 2008). Fiber-modified HVs were initially generated on 293-fiber cells and subsequently amplified on 293 cells to remove wild type fibers in the final HV capsid. Proper fiber modification in the genome of individual HVs was verified by DNA sequencing (FIG. 5b).

Example 3

Figure 6:
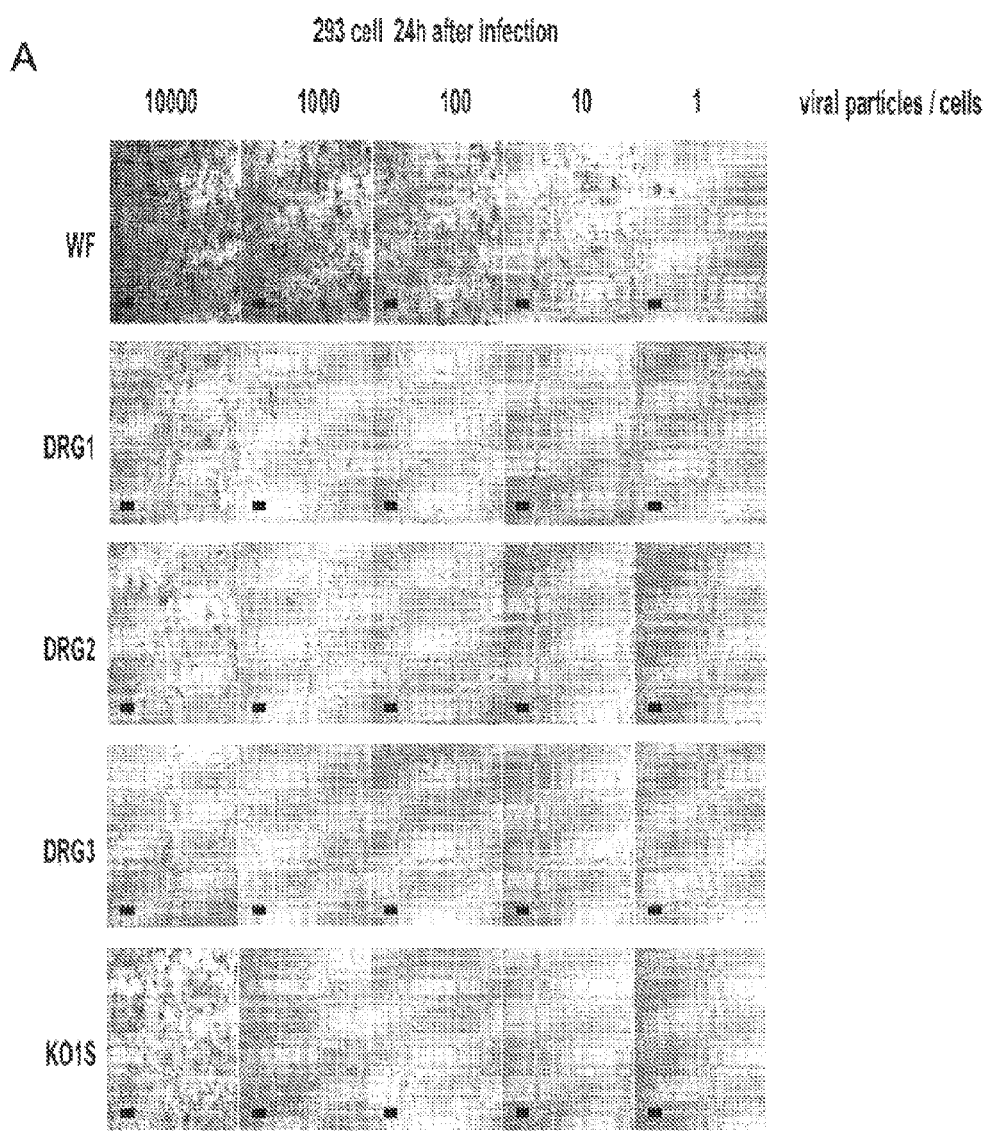
FIG. 6 LacZ expression in cells following infection with fiber-modified helper virus in vitro. (a) X-gal stain of 293 cells 24 hours after infection with fiber-modified HVs at $1-1 \times 10^4$ vp/cell. Bar, 50 mm. (b) X-gal stain of DRG neurons. Bar, 20 mm.
Figure 6:
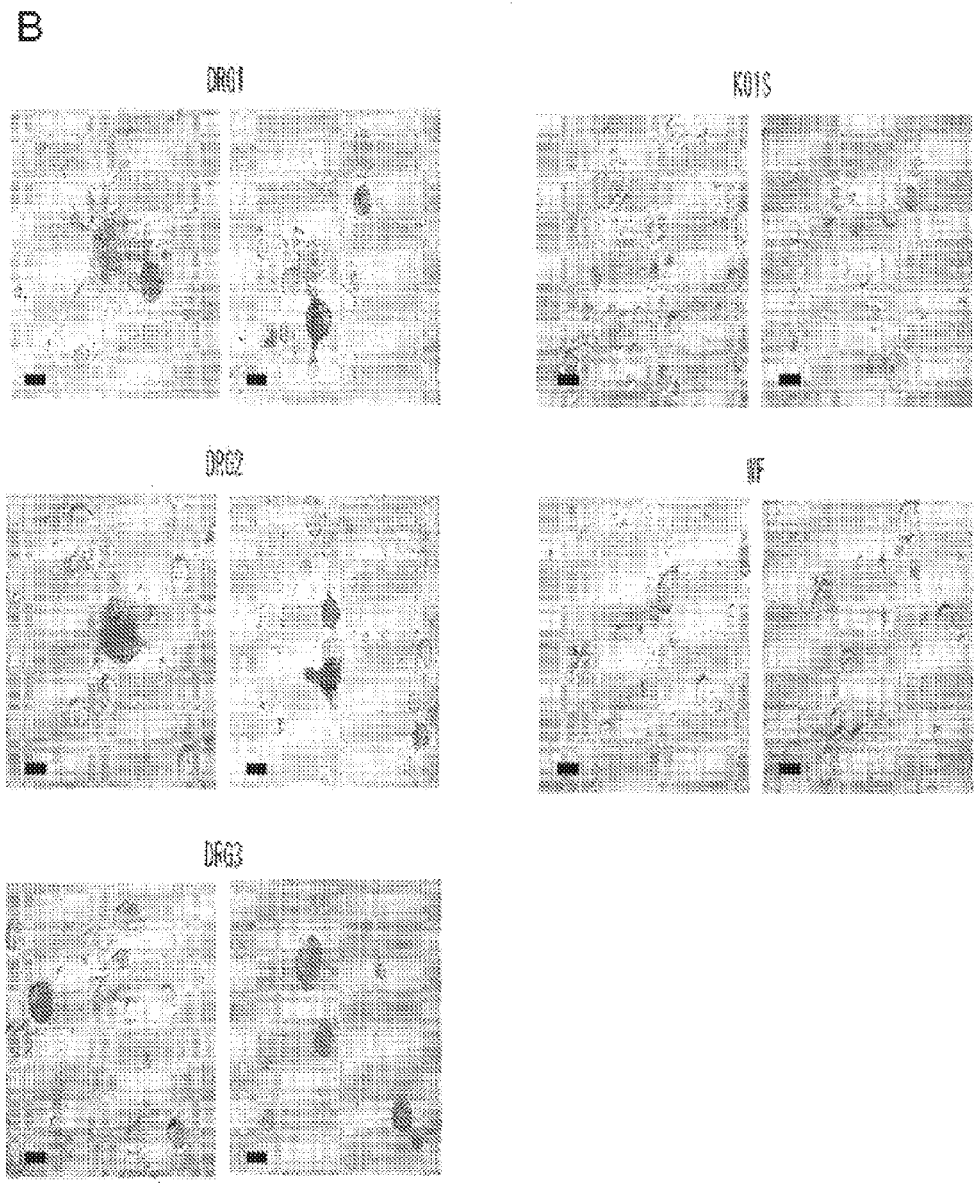

HV Containing DRG Neuron Targeting Motifs Efficiently and Specifically Transduces DRG Neurons In Vitro and In Vivo As compared to wild-type fiber HV (HV-WF), HV-KO1S* showed 100-fold lower infectivity to 293 cells (FIG. 4b, note log scale), indicating that HV-KO1S* had lost its capacity to interact with primary docking sites on 293 cells. As the different DRG motif-containing HVs were engineered on an HV-KO1S* backbone, they also transduced 293 cells poorly (FIG. 4b, see also FIG. 6a). Transduction of isolated DRG neurons by HV-WF was about 100-fold less efficient than that of 293 cells. In contrast, HVs containing DRG targeting motifs 1-3 all displayed markedly enhanced transduction of isolated DRG neurons (FIG. 4c, note log scale). Interestingly, HV-DRG1 showed the highest transduction efficiency followed by DRG2 and DRG3. Compared to HV-WF, HV-DRG1 showed 100-fold higher efficiency of transduction of DRG neurons in vitro, while HV-KO1S* displayed minimal transduction capacity (<1% of that of HV-WF, and <0.001% that of HV-DRG1). (see also FIG. 6b).

Figure 7:
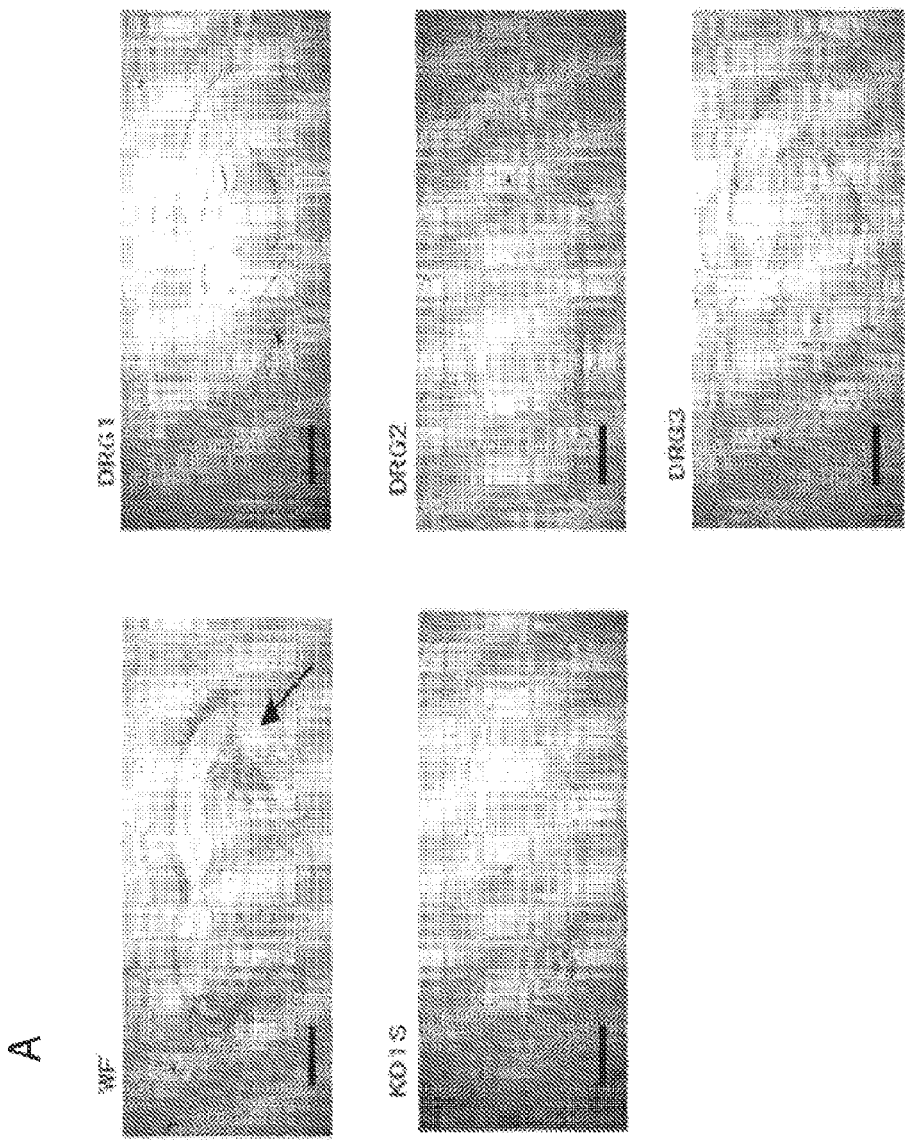
FIG. 7 X-gal stain of nervous tissues. $1 \times 10^8$ vp of fiber-modified HVs were injected into wild type C57/BL6 mice via subarachnoid space at the lumbar level. Mice were sacrificed for X-gal staining 5 days after HV injection. (a) Brain. Arrow shows X-gal stain in the lateral ventricular region. Bar, 1200 mm. (b) Spinal cord. Arrow shows central canal of spinal cord. Bar, 250 mm. (c) DRG. Bar, 100 mm. (d) Sciatic nerve. Arrows indicate X-gal positive areas at the surface of nerves. Bar, 50 mm.
Figure 7:
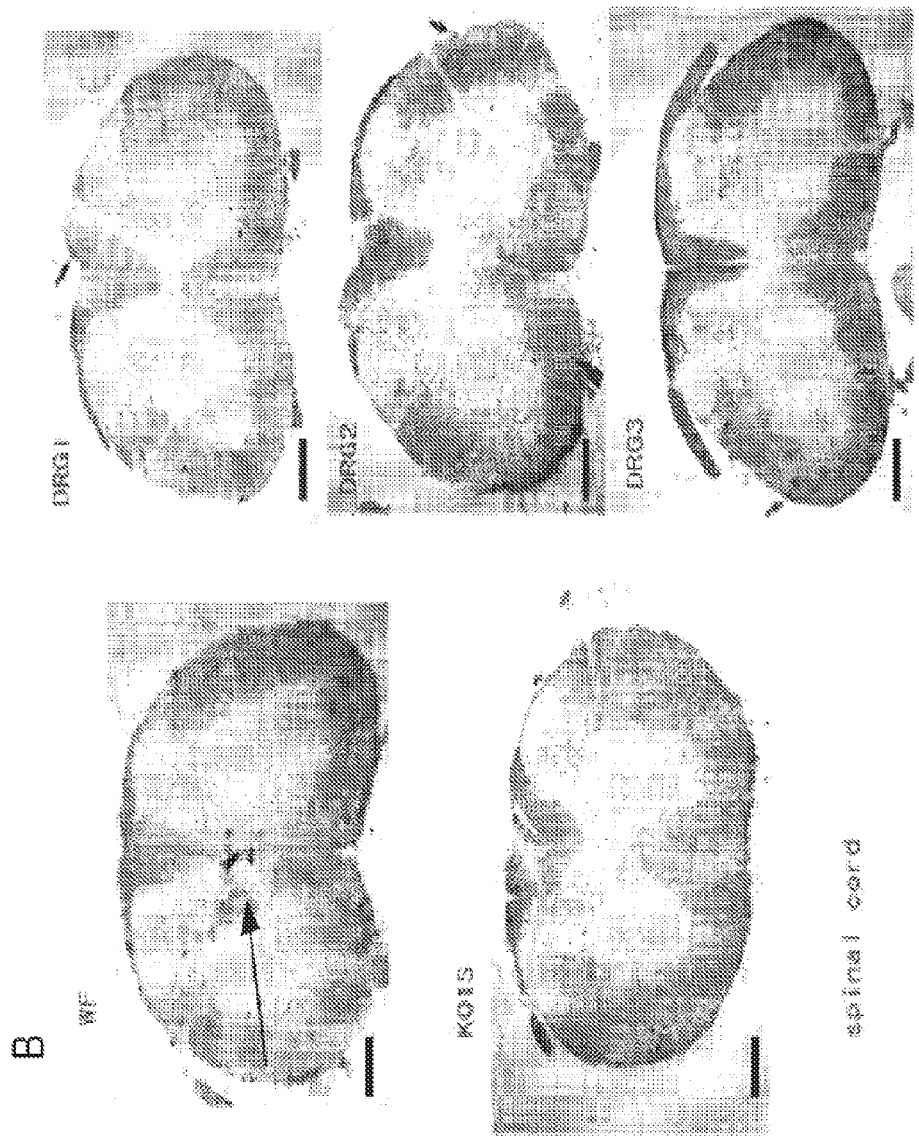
Figure 7:
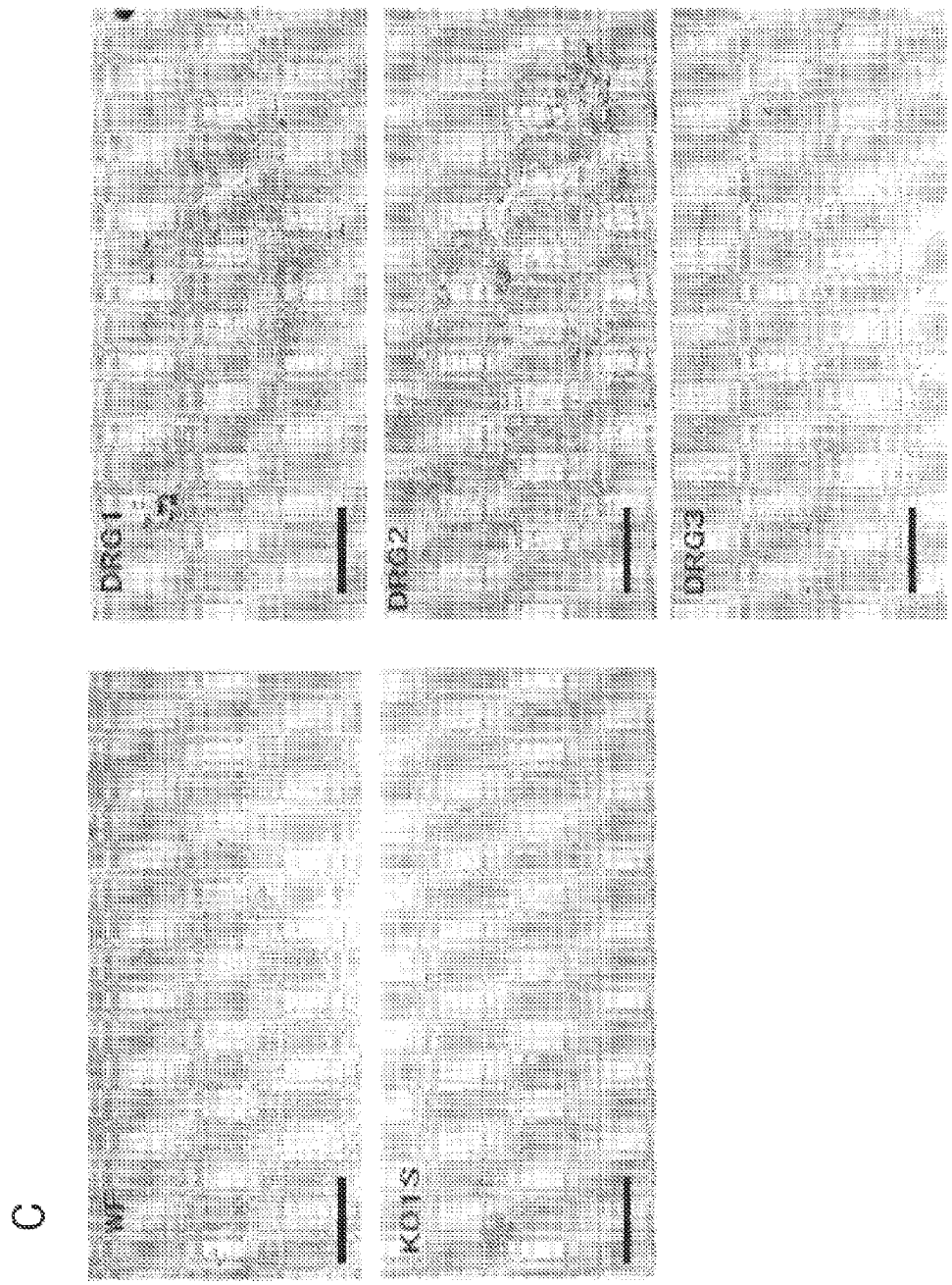
Figure 7:
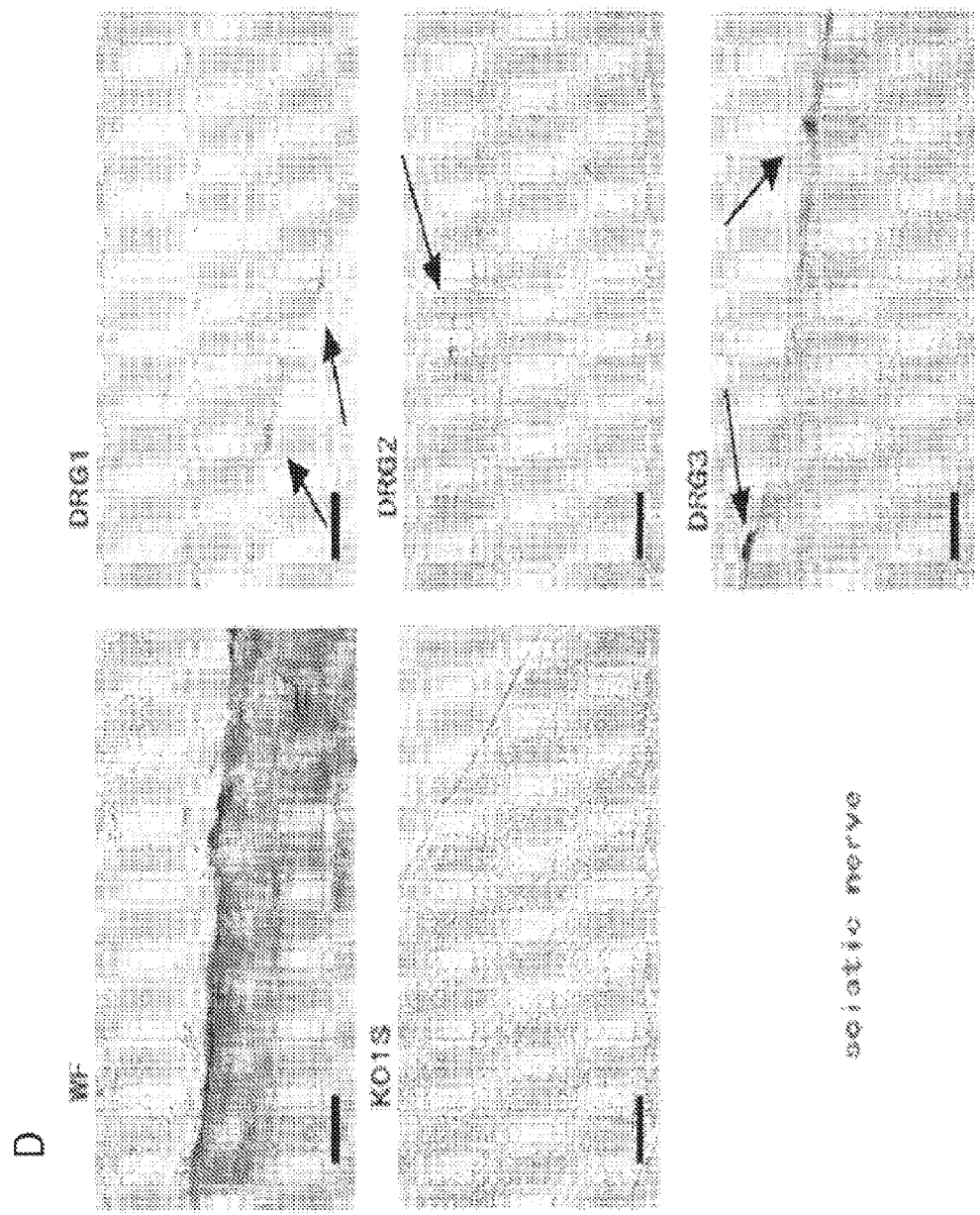

The transduction efficiency of DRG neurons was investigated by the different HVs in vivo by injecting $1 \times 10^8$ viral particles (vp) of HVs containing dual βgeo (β-galactosidase-neo fusion protein) and luciferase gene cassettes into the subarachnoid space of C57BL/6 mice and compared the biodistribution of the-fiber modified HVs five days later. X-gal staining was barely detectable in DRG of mice treated with HV-WF or HV-KO1S*. In contrast, transduction of DRG by HVs containing DRG targeting motifs was evident from the X-gal staining (FIG. 4d, FIG. 7c). Occasional punctate X-gal reaction product was detected in the root fibers leading to the DRG in HV-WF treated mice. Close microscopic observation revealed rare X-gal positive areas in the brain of mice treated with HV-WF (e.g., an X-gal positive area was identified in the lateral ventricular region. see FIG. 7a online), but almost never in the brain of mice treated with other HVs. The spinal cord stained positive around the vector injection site and at the dorsal intermediate sulcus and central canal in mice treated with HV-WF. Although scant staining was found in the injection sites of mice treated with HV-DRG1, -DRG2 and -DRG3, there was no staining in mice treated with HV-KO1S* (FIG. 4d, FIG. 7b). X-gal positive areas were also identified on the surface of the sciatic nerve in the WF, and to a much smaller extent, the DRG1, DRG2 and DRG3 groups, but not in the KO1S* group (FIG. 7d).

The observation based on X-gal staining pattern was corroborated by quantifying HV-induced luciferase activity. Again, there was low luciferase activity in the HV-WF group in all tissues, whereas high luciferase activity was present almost exclusively in the DRG of the three DRG-targeting HV-treated animals. Transduction by HV-DRG1 and DRG2 was 100-fold higher than that by HV-WF. HV-DRG3 was substantially less efficient, being only 4-fold higher than HV-WF (FIG. 4e, note log scale). Luciferase activity from HV-KO1S* (detargeted) was negligible in all tissues. Long-term LacZ mRNA expression induced by HV-WF and HV-DRG1 by quantitative RT-PCR. The expression of LacZ mRNA decreased over time in both groups (FIG. 4f, note log scale). By 60 days, LacZ mRNA was barely detectable in the WF group, but was still present at a substantial level in the DRG1 group.

Example 4

Figure 8:
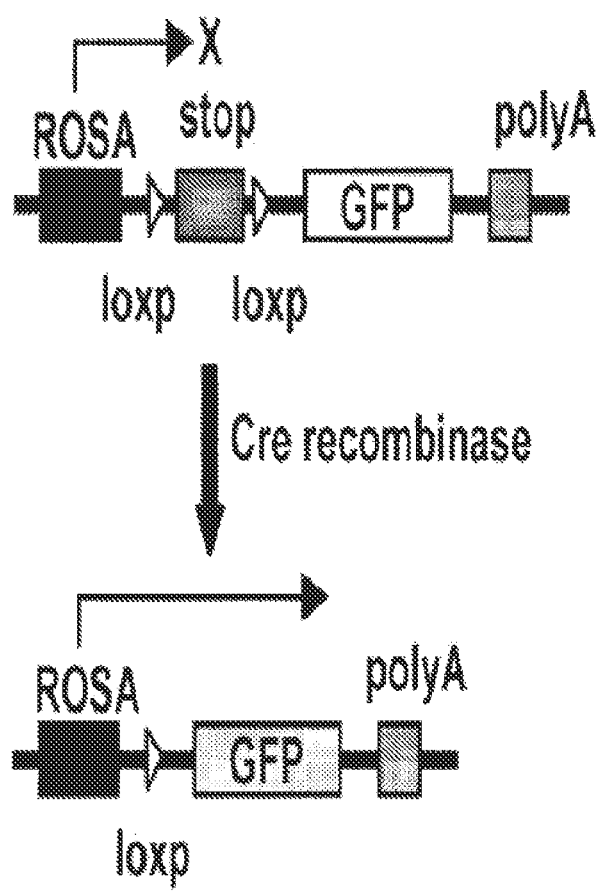
FIG. 8 Helper-dependent adenoviral vectors harboring DRG neuron homing peptides transduce DRG neurons and turn on GFP expression in ROSA-GFP transgenic mice. (a) A schematic presentation of the strategy to evaluate targeting tissues in ROSA-GFP transgenic mice using fiber-modified HD Ad expressing Cre. In ROSA-GFP mice, GFP gene expression is blocked by a STOP fragment flanked by loxP sequence. Upon excision of the STOP fragment by Cre expression, GFP is expressed. Thereby, GFP expression is dependent on HDAd-mediated Cre gene transfer. (b,c) Cre and GFP mRNA expression in neuronal tissues. $1 \times 10^8$ vp of fiber-modified HDAd expressing Cre were injected through subarachnoid space at lumbar level into ROSA-GFP mice. Neuronal tissues were harvested 5 days after vector injection and mRNA was quantified by real time RT-PCR. Results are expressed as relative to the mRNA level in DRG of mice treated with HDAd containing wild type fiber. *$P<0.05$ and **$P<0.01$ vs. WF group, #$P<0.05$, ##$P<0.01$ vs. KO1S* group. HV contamination in fiber-modified HDAd determined by real time PCR ranged from 0.0007 to 0.037%. (d) Immunoblot analysis of Cre and GFP protein expression 5 days after HDAd injection. 20 μg protein was loaded on 7.5-15% SDS-PAGE. Band intensities were normalized to GAPDH. Protein expression is expressed relative to that of HDAd-WF. (e) GFP expression in DRG. Upper and middle panels show whole DRG tissues. Upper panel is under GFP filter and the middle is under bright filter. Broken lines outline the margin of DRG tissues. Bottom panel is DRG sections with DAPI nuclear stain. Bar, 100 μm. (f,g) Long term Cre and GFP mRNA expression in DRG. $1 \times 10^8$ vp of HDAd-WF-Cre or HDAd-DRG1-Cre were injected into ROSA-GFP mice and sacrificed at various time points for quantitation of Cre and GFP mRNAs in DRG. The mRNA levels are expressed as relative to the mRNA in HDAd-WF-Cre-treated mice sacrificed at day 60. *$P<0.001$, **$P<0.01$ vs. WF group.
Figure 8:
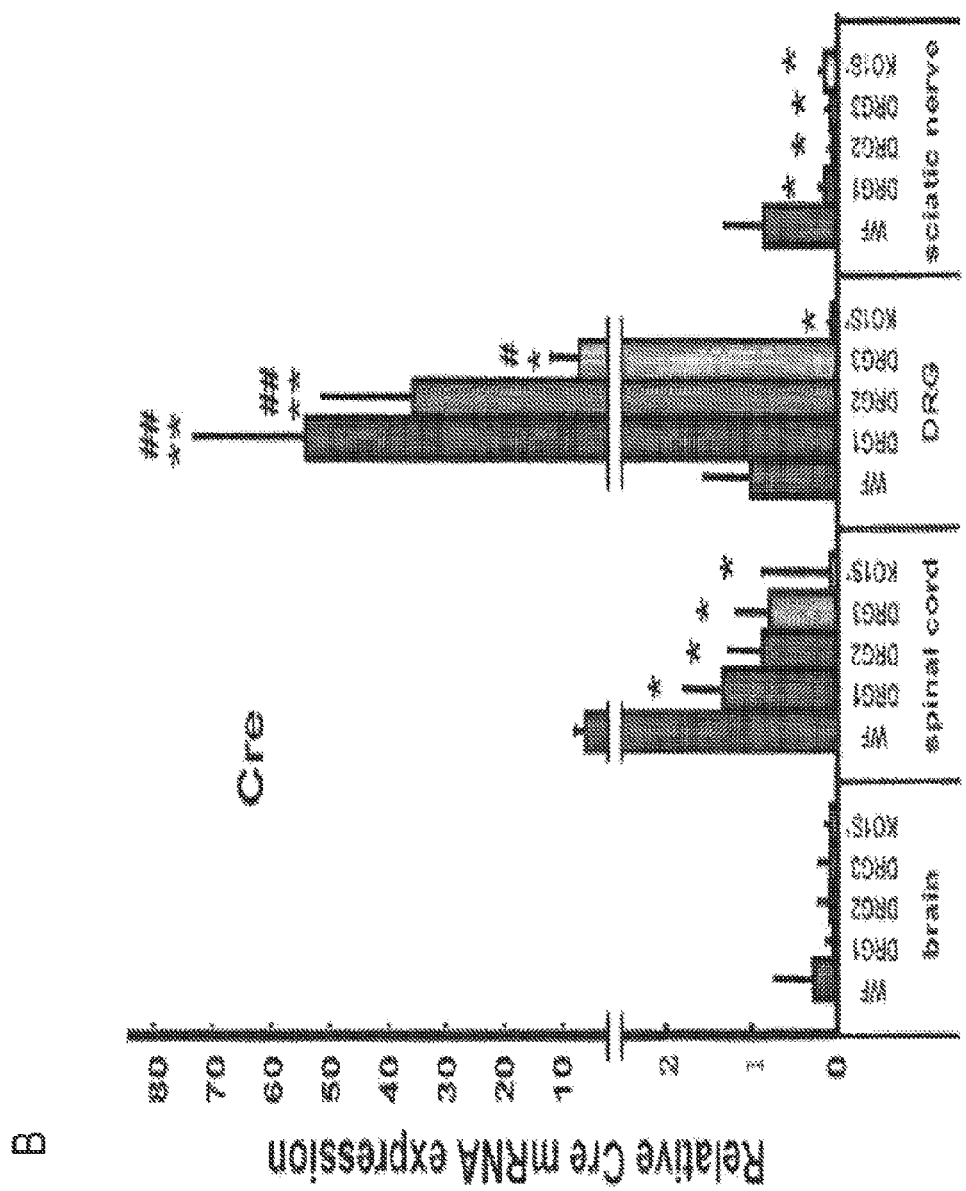
Figure 8:
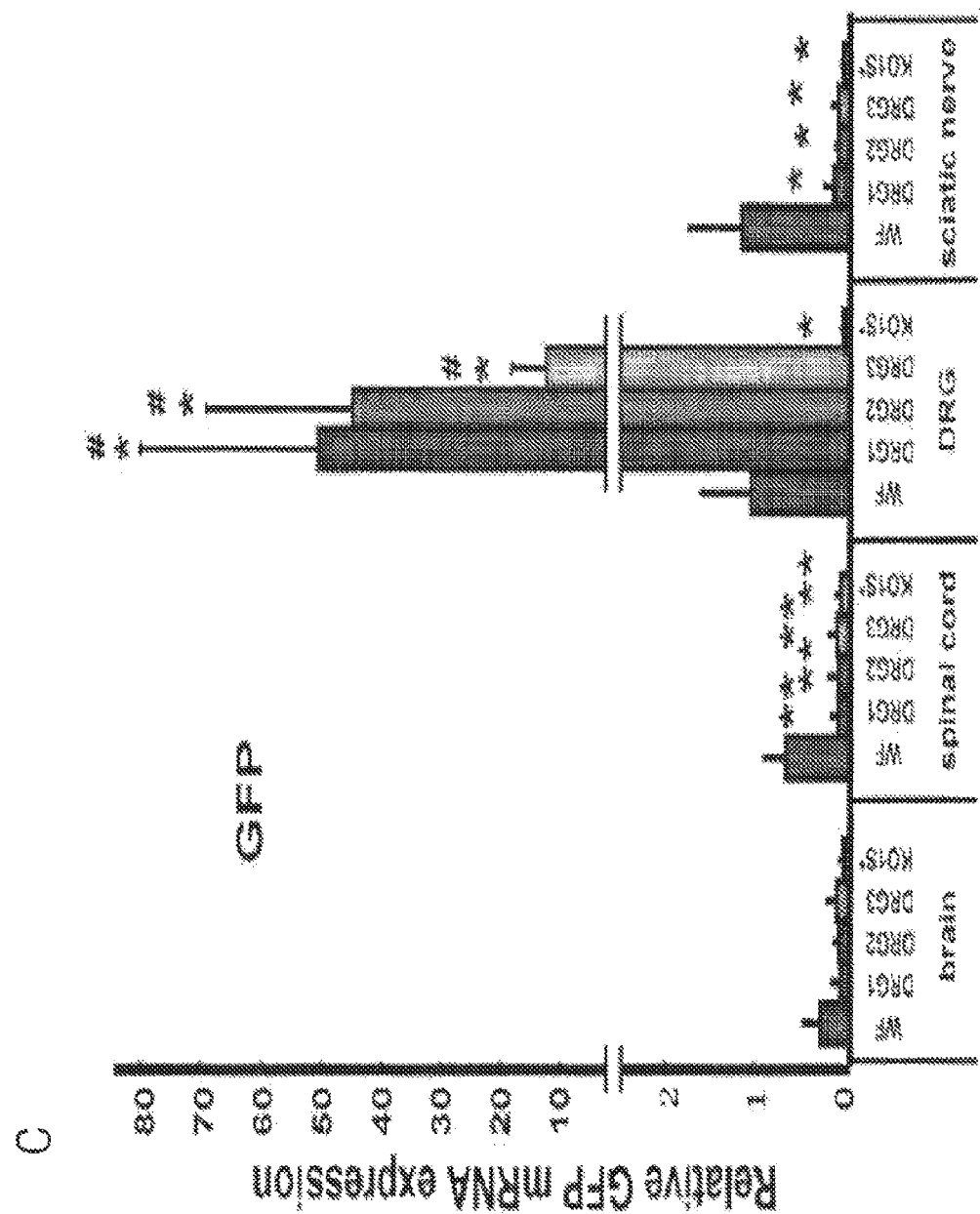
Figure 8:
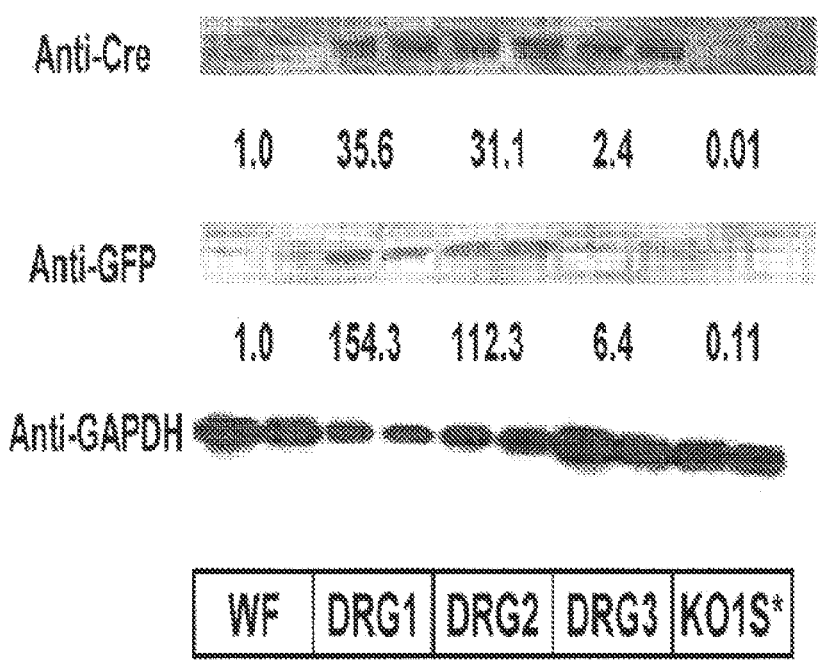
Figure 8:
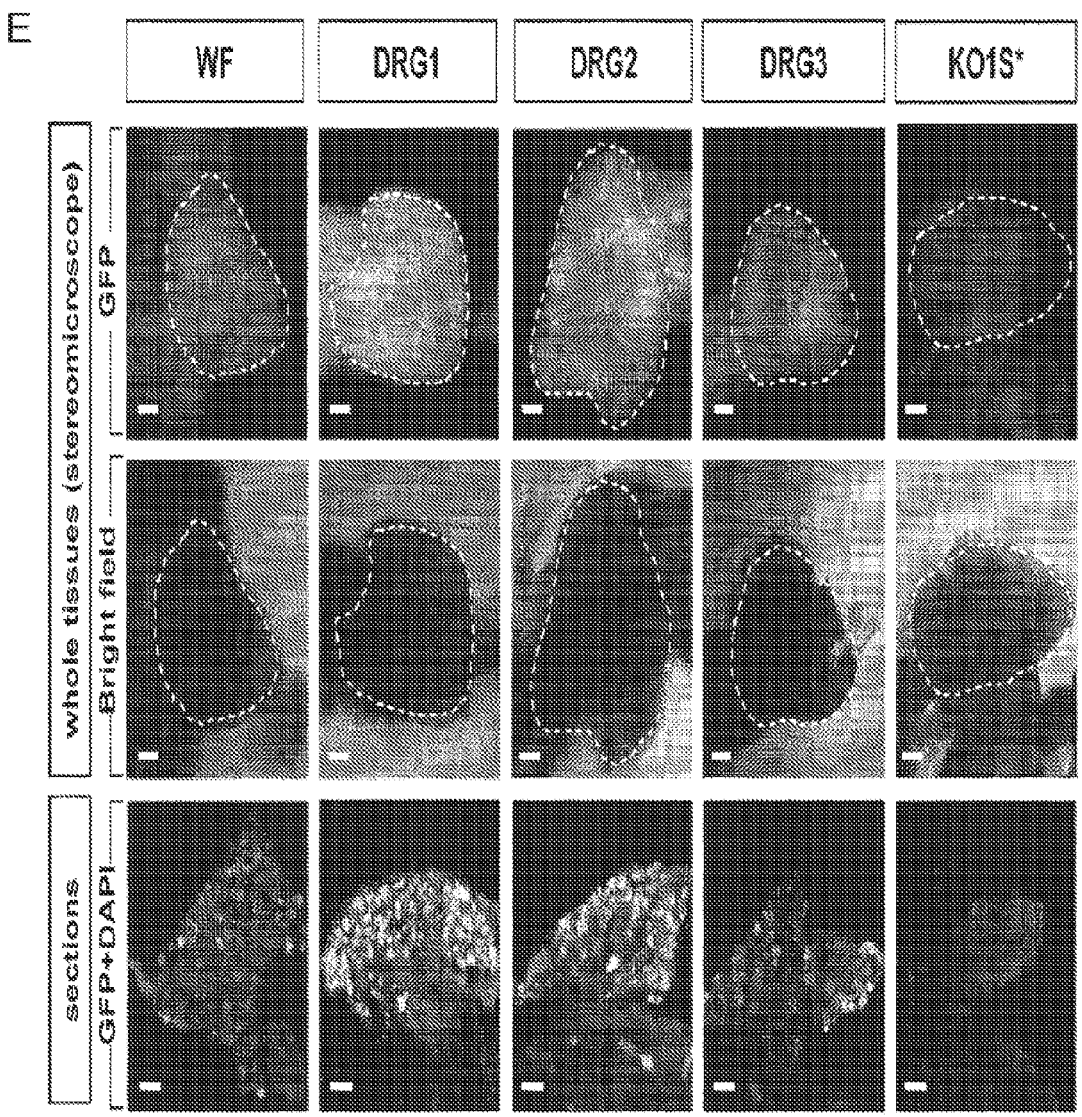
Figure 8:
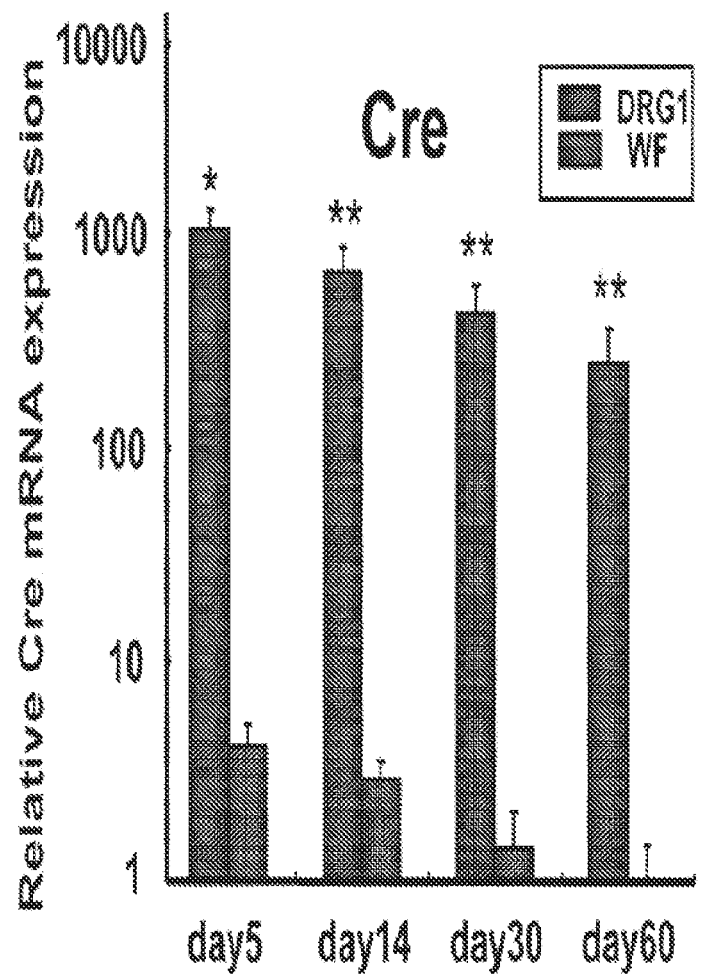
Figure 8:
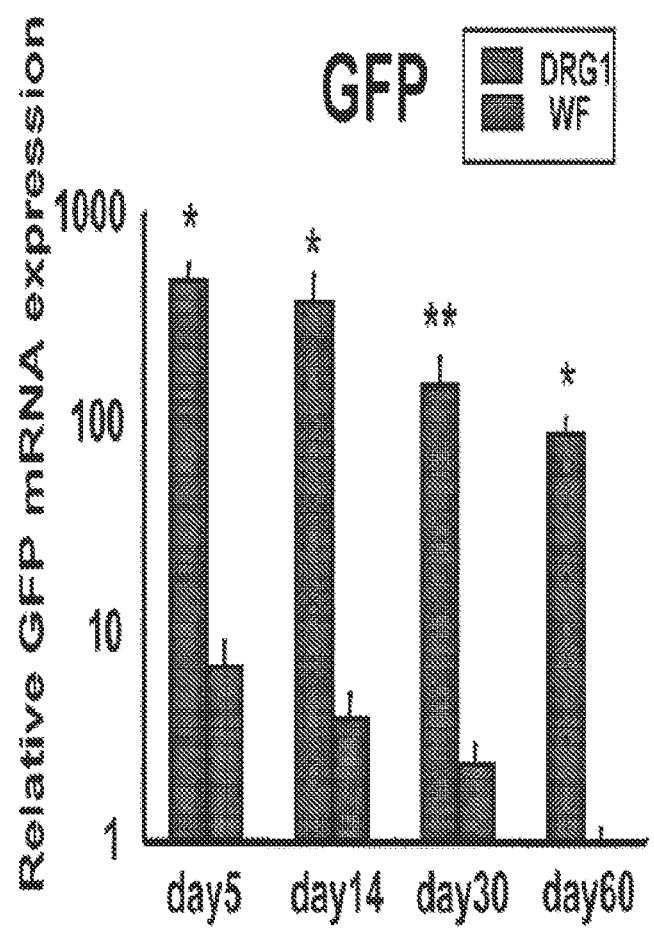

Fiber-Modified HDAd Vectors Expressing Cre Turn on GFP Expression in DRG Neurons of Rosa-GFP Mice To test whether HDAd containing DRG targeting motifs in the fiber transduce the intended targets, ROSA-GFP mice were utilized, in which transgenic GFP expression is interrupted by the Stop fragment flanked by loxP sequences. Upon Cre-mediated excision of the Stop fragment, GFP is expressed (FIG. 8a). HDAd expressing Cre driven by EF-1 promoter were generated using HV-WT (HDAd-WF-Cre) and then the inventors switched vector capsids by coinfection with HDAd-WF-Cre and HV-DRG 1, -DRG2, -DRG3 or -KO1S* (FIG. 3c). HDAd were injected locally into the subarachnoid space, mice were sacrificed 5 days later, and mRNA expression was determined by real time RT-PCR. The expression of Cre and GFP in different tissues (FIG. 8b,c) was consistent with the biodistribution of HV (FIG. 4c-e). All DRG neuron-targeting HDAd expressed Cre and GFP 10-50 fold higher than HDAd-WF-Cre in DRG, while HDAd-KO1S* showed minimal expression. The Cre mRNA level was barely detectable in brain and sciatic nerve. It was generally low in spinal cord, in which tissue the HDAd-WF-Cre led to the highest expression compared with the other tissues and other vectors tested (FIG. 8b). GFP mRNA expression was barely detectable in all three sites, i.e., brain, spinal cord and sciatic nerve (FIG. 8c). Furthermore, very low levels of Cre and GFP mRNA were detected in DRGs of the HDAd-WF-Cre-treated group (FIG. 8b,c). In contrast, HDAd-DRG1, -DRG2 and -DRG3 led to parallel high level expression of both Cre and GFP mRNA expression in DRGs of injected animals. In all cases, HDAd-KO1S* induced Cre and GFP expression was essentially undetectable. The relative mRNA levels were also reflected by the relative expression of Cre and GFP proteins by immunoblot analysis (FIG. 8d). HDAd-DRG1-Cre and -DRG2-Cre induced 30-fold higher protein levels than HDAd-WF-Cre. Similarly, GFP expression in mice treated with HDAd-DRG1-Cre or -DRG2-Cre was over 100-fold higher than that with HDAd-WF-Cre, while it was virtually undetectable in mice treated with HDAd-KO1S*-Cre (FIG. 8d).

Figure 9:
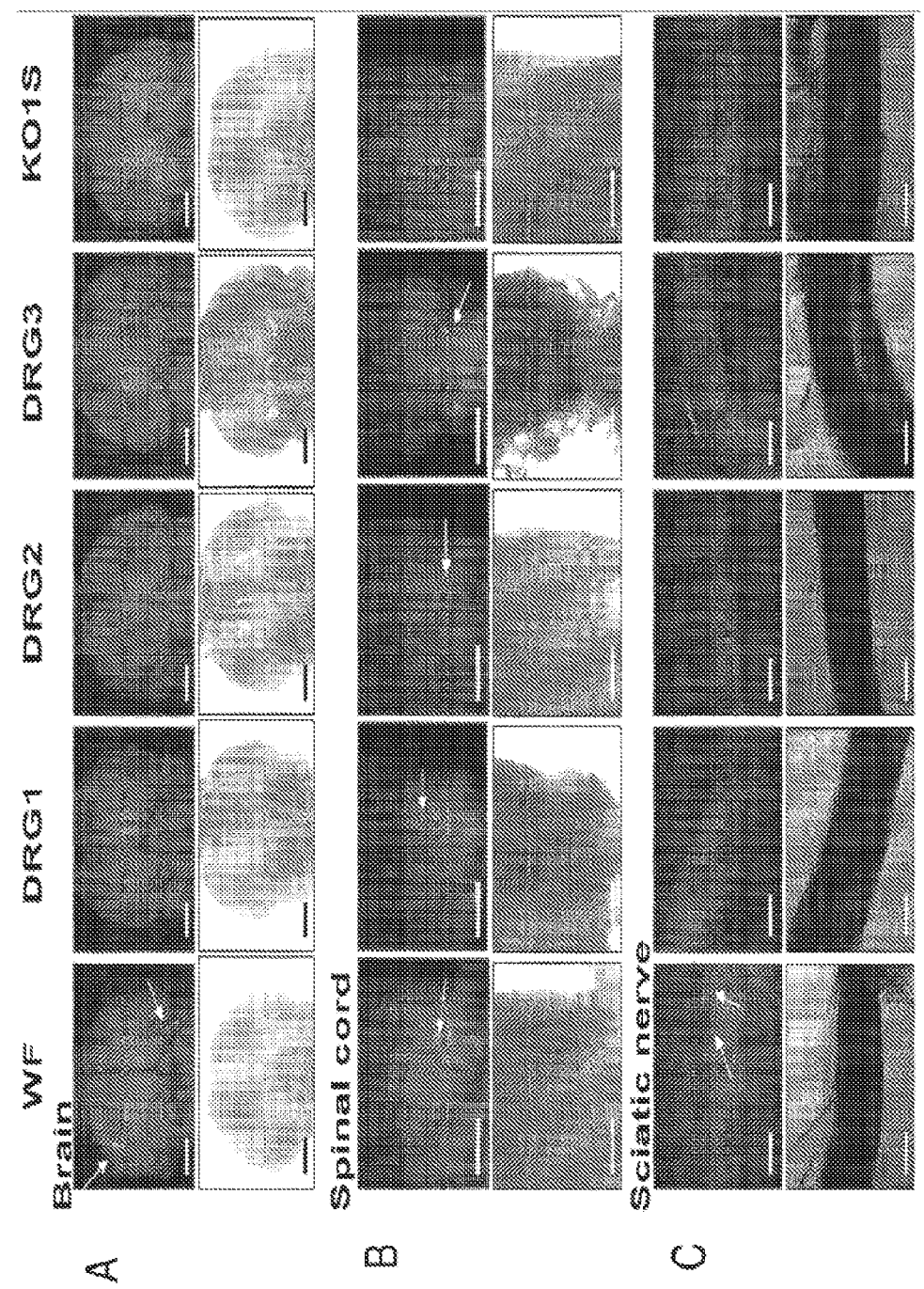
FIG. 9 Histological analysis of GFP expression in brain, spinal cord and sciatic nerve isolated from ROSA-GFP mice after administration of fiber-modified HDAd. (a-c) Whole tissue image. First row shows the image under GFP filter. Second row shows the same area under bright field. Bar, 2 mm in a, 500 mm in b, 200 mm in c.

By fluorescent microscopy, GFP fluorescence was readily detected in individual neurons of DRGs transduced by HDAd-DRG1 and -DRG2 (FIG. 8e, top panel). HDAd-DRG3-transduced DRGs emitted weak fluorescence; HDAd-WF also produced detectable but even weaker fluorescence. No fluorescence was detected in the KO1S* group. The proportion of GFP+ cells to DAPI+ neurons was 88.1% in the DRG1 group, 67.7% in the DRG2 group, 16.9% in the DRG3 group, and 6.3% in the WF group, respectively (FIG. 8e, bottom panel). A few scattered GFP+ areas were found in the brain and sciatic nerve of the WF group (Arrows, FIG. 9), while GFP+ areas were identified in the spinal cord at or close to the injection sites in all except the KO1S* group (FIG. 9).

Example 5

HDAds Produce Long-Term Transgene Expression with Markedly Attenuated Inflammatory Response Transgenes delivered by Ad including HDAd are essentially not integrated into the host genome, and their expression goes down with cell turnover. The level of Cre and GFP mRNA expression was compared in the DRG of HDAd-DRG1 and HDAd-WF treated groups. HDAd-WF treatment led to low level expression of both at day 5 with rapid decline in relative expression over the next two months, such that only 22.9% (for Cre) and 14.5% (for GFP) of the initial (5 day) mRNA level remained at 60 days (FIG. 8f,g). In contrast, HDAd-DRG1 treated DRGs led to greatly enhanced >100-fold higher Cre and GFP expression at day 5. Over the two months afterwards, mRNA expression went down at a greatly reduced rate and was 23.3% for Cre and 18.5% for GFP mRNA at day 60.

Figure 10:
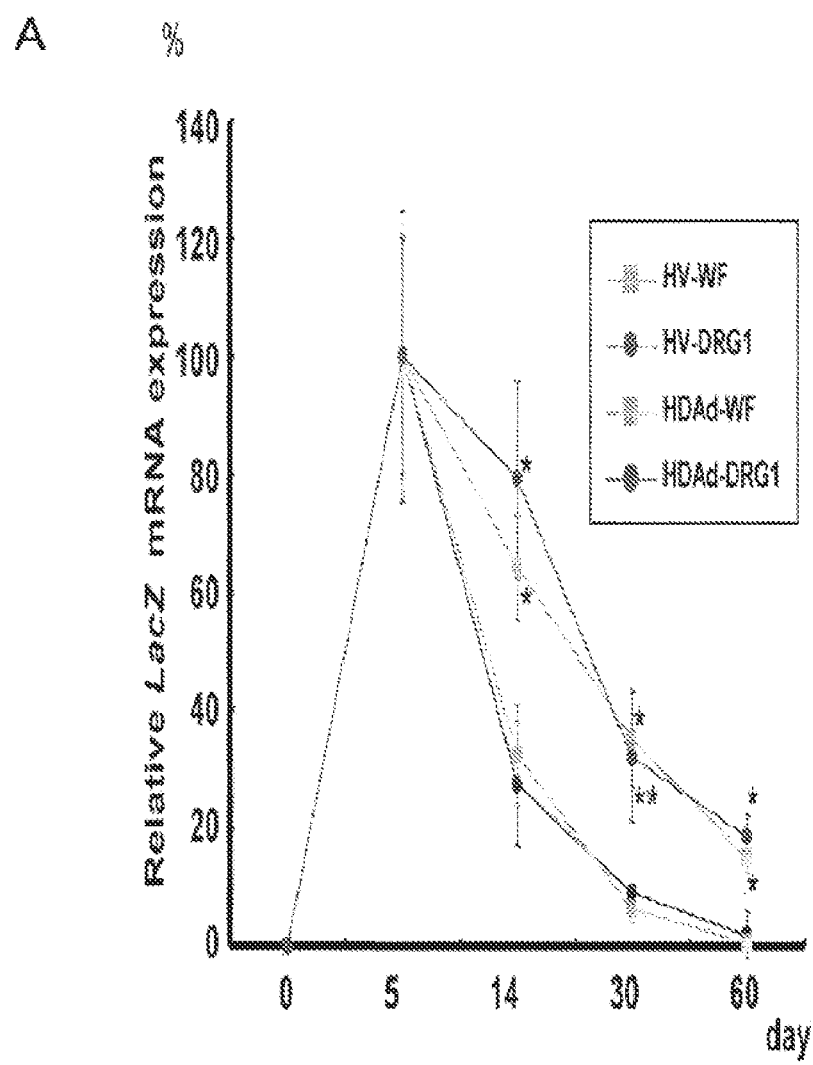
FIG. 10 Fiber-modified HDAd supports long-term transgene expression and improves safety profile. (a) Long term expression of lacZ gene in DRG. $1 \times 10^8$ of Ad vectors were injected into C57BL/6 wild type mice and DRG was isolated at various times for quantitation of LacZ mRNA. The LacZ mRNA levels were normalized to β-actin mRNA. All results are expressed as relative to LacZ mRNA level at day 5. *$P<0.001$, **$P<0.01$ vs. HV with the same fiber (e.g., HDAd-WF vs. HV-WF). (b-d) Targeted HDAd vector induces less inflammation. Cerebrospinal fluid (CSF) was collected at various time points and cytokines were measured by ELISA. *$P<0.01$ and **$P<0.05$ vs. HV-WF, †$P<0.01$ and ††$P<0.05$ vs. HDAd-WF, ‡$P<0.01$ and ‡‡$P<0.05$ vs. HV with the same fiber.
Figure 10:
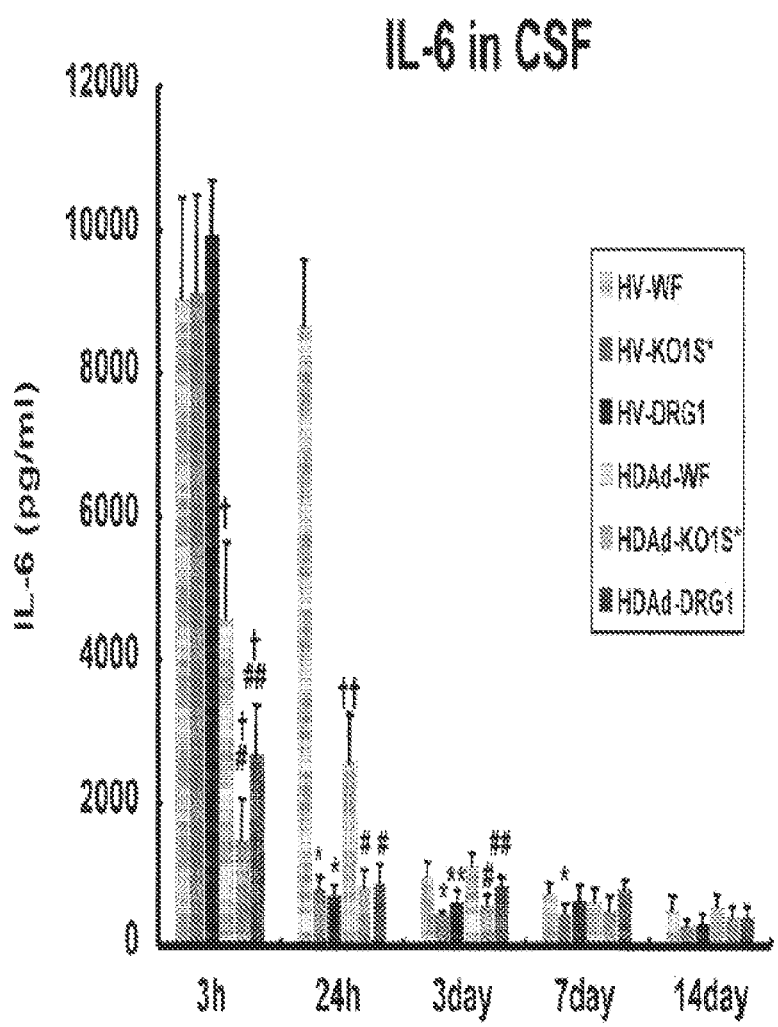
Figure 10:
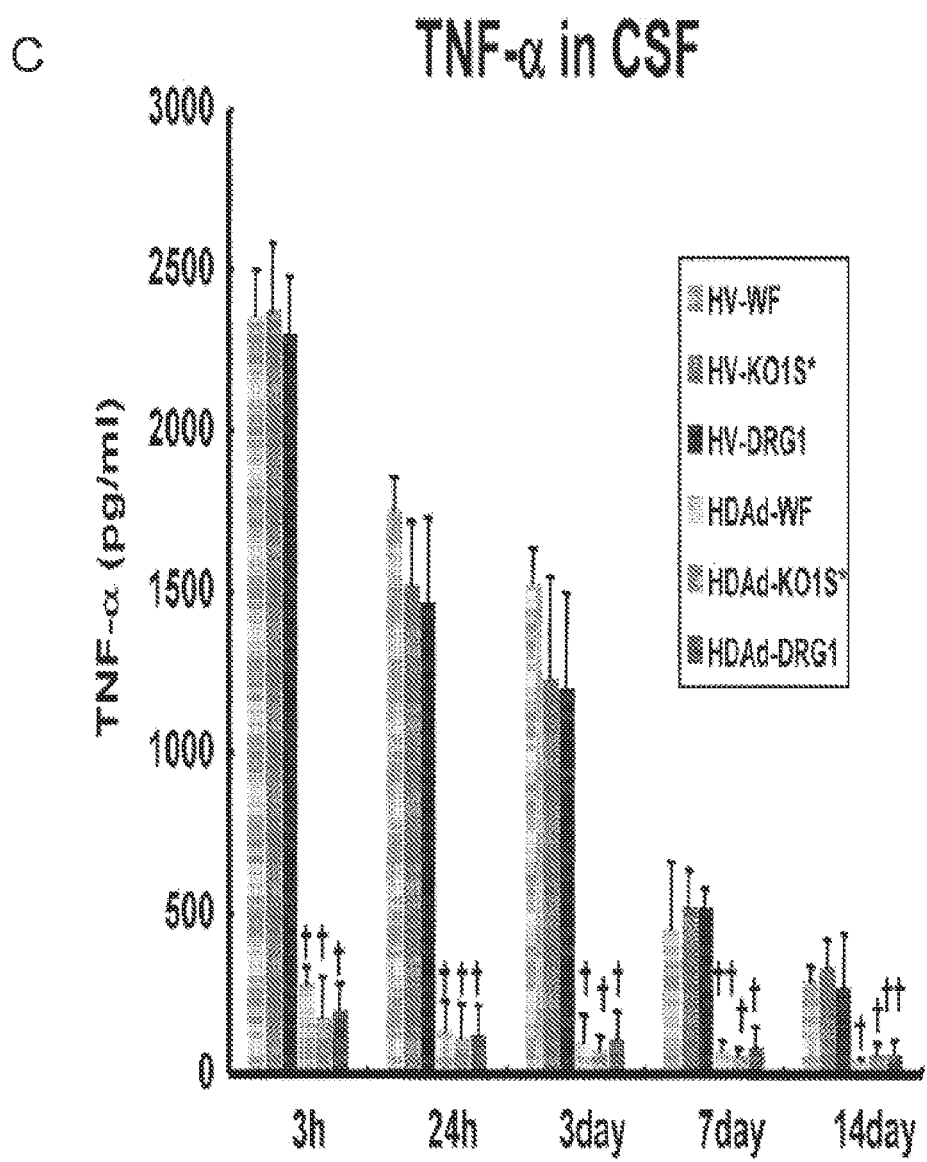
Figure 10:
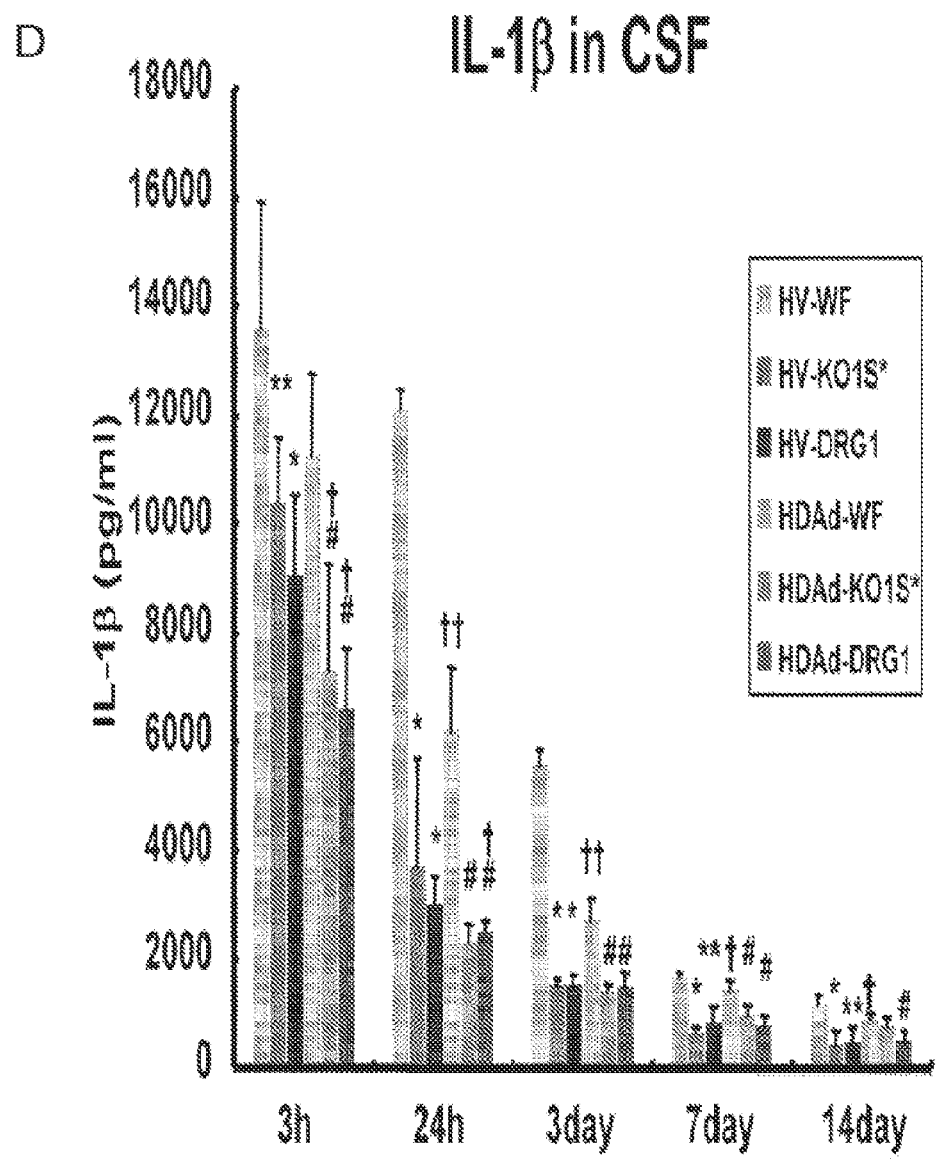

To further examine both the long-term transgene expression by HDAd and its effect on the host inflammatory response, βgeo expressing HDAd and HV were injected into mice. The inventors first quantitated LacZ mRNA expression for the next two months (FIG. 10a). Arbitrarily setting the LacZ mRNA expression level at day 5 as 100%, in the HDAd groups (for both HDAd-WF or HDAd-DRG1), expression level gradually decreased to ~20% at day 60. When the corresponding HVs (HV-WF or HV-DRG1) were used, the decline in mRNA was substantially faster, going down to about 0.4-1.7% of the initial level at day 60. Thus, the relative stability of transgene expression depends on the vector (HV vs HDAd), lasting substantially longer for HDAd than for HV, and not on the fiber type (wild-type, WF, vs DRG-targeted, DRG1). However, since the HDAd-DRG1 led to 100-fold higher initial expression, at the end of 60 days, HDAd-DRG1-mediated LacZ expression was still readily apparent while HV-mediated expression was no longer evident.

Figure 11:
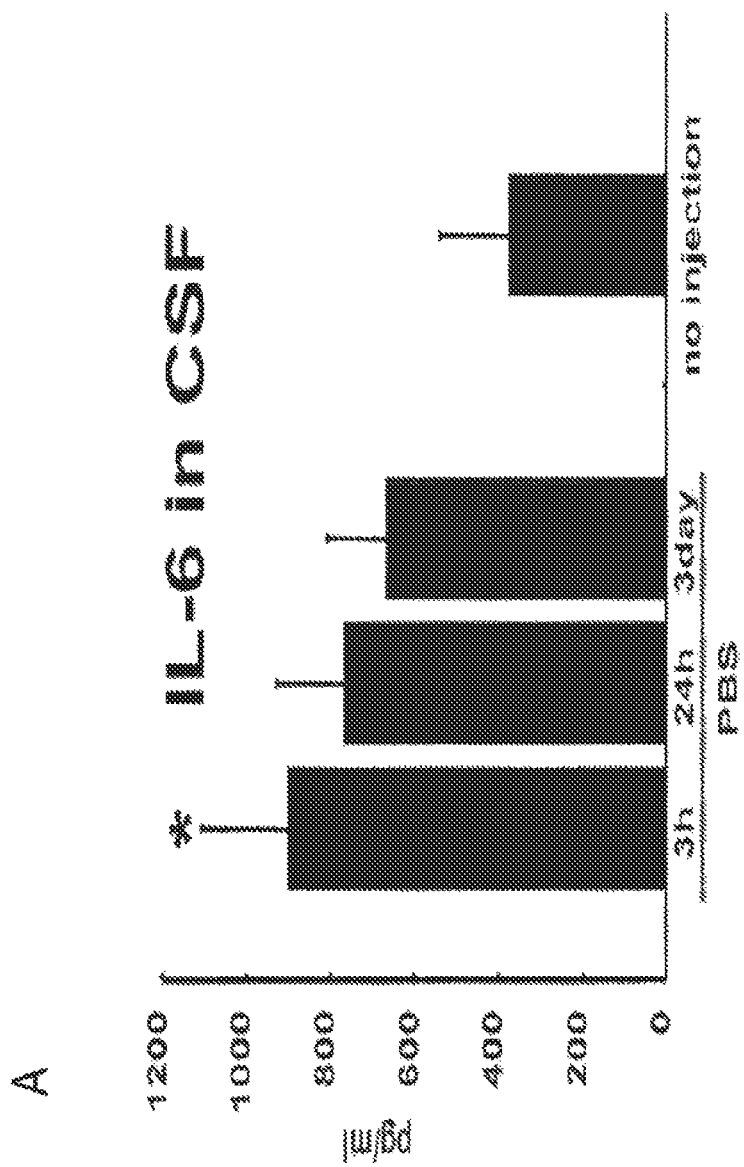
FIG. 11 Cytokine levels in cerebrospinal fluid (CSF). PBS was injected to C57BL/6 mice through subarachnoid space at lumbar level. CSF was collected at 3 hour, 24 hour and day 3. Cytokines were measured by ELISA. a. IL-6, b. TNF-α and c. IL-lb. *$P<0.01$ and **$P<0.05$ vs. no injection (n=3-4).
Figure 11:
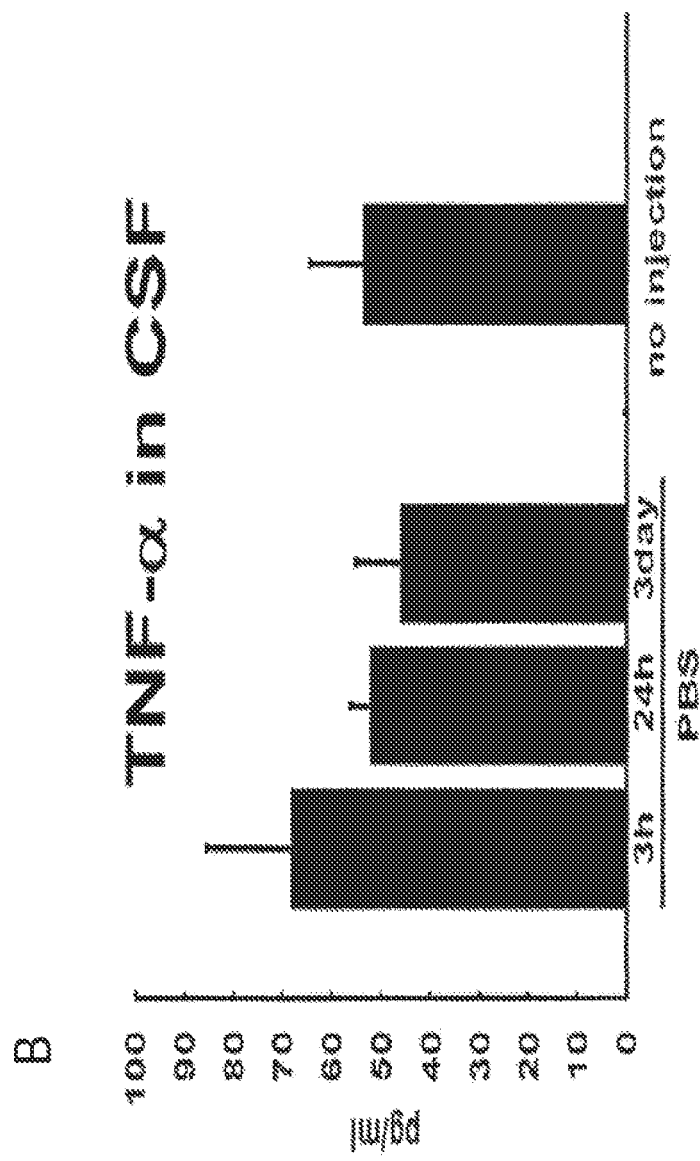
Figure 11:
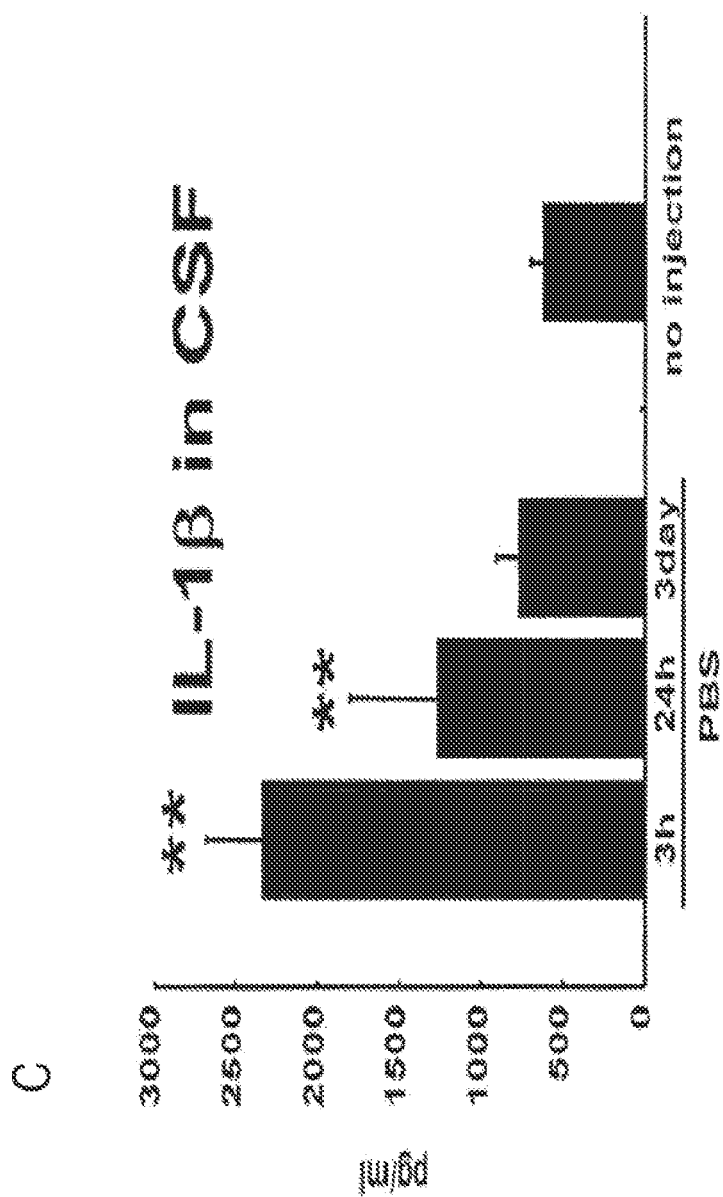

HDAd does not produce any viral proteins and HDAd-mediated transgene expression is largely free of chronic inflammatory response. Nonetheless, an acute inflammatory response can happen following HDAd or HV administration as a result of innate immunity. Acute toxicity was monitored by measuring cytokines secreted into the CSF. IL-6 level was increased 3 hours after vector injection in all groups, but to a much lesser extent in mice treated with HDAd. However, IL-6 production following HDAd-KO1S* and HDAd-DRG1 was significantly lower than that after HDAd-WF injection (FIG. 10b). Although IL-6 was still elevated in mice treated with HV-WF 24 hours later, it returned to the level similar to that treated with PBS (FIG. 11a) in all other groups, suggesting that attenuation of natural tropism reduces Ad-associated induction of IL-6. The secretion of TNF-α was not influenced by detargeting (FIG. 10c, FIG. 11b). However, the response to HDAd and HV differed markedly. HV produced a robust TNF-α response that lasted at least two weeks, while the response to HDAd was greatly attenuated (FIG. 10c). The kinetics of CSF IL-1p differed from that of IL-6 or TNF-α (FIG. 10d). Importantly, PBS alone increased IL-1β 4-fold 3 hours after injection and returned to pretreatment level by day 3 (FIG. 11c). IL-1β level was elevated in all groups 3 hours after the vector injection. Although the increase of IL-1β in the HV groups was higher than the HDAd groups, the difference, especially early on (at 3 h), was much smaller in comparison to that observed for IL-6 or TNF-α.

Example 6

A Single Injection of DRG-Targeting HDAd Expressing β-Hexosaminidase Restores Enzyme Activity and Function of Sensory Neurons in a Mouse Model of Sandhoff Disease DRG neurons are involved in many neurological diseases which impair the structural integrity and function of sensory neurons. However, few well characterized animal models are available to test the effects of restoration of function in sensory neurons. A mouse counterpart of Sandhoff disease in humans was a useful model for this purpose. Sandhoff disease is caused by mutations in the β-hexosaminidase β-subunit gene. Absence of this enzyme subunit leads to defective GM2 ganglioside degradation and massive accumulation of the ganglioside and other substrates in the lysosomes of neurons. The mouse model for this disease, hexb$^{-/-}$ mice, has been shown to develop progressive impairment of motor function (Sango et al., 1995). The DRG of these mice exhibit the typical histopathological changes of GM2 gangliosidosis; furthermore, the animals also display abnormal sensory nerve conduction velocity and action potential, objective measurements that can be used to gauge the severity of the disease.

Figure 12:
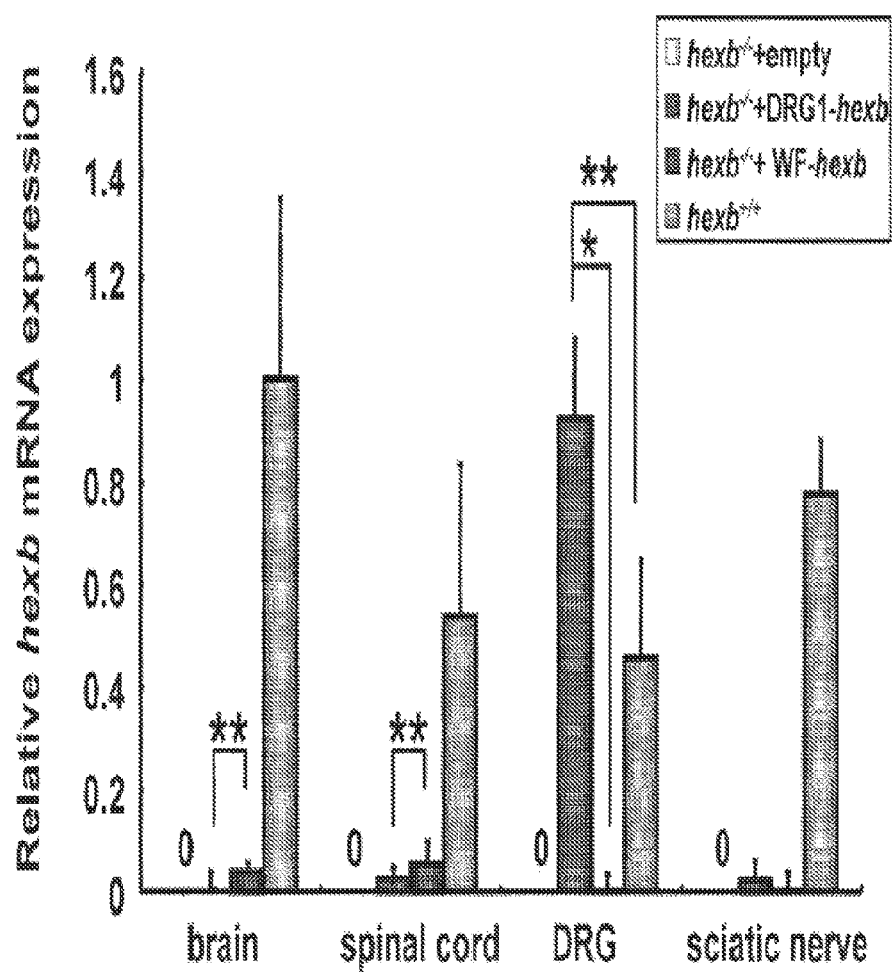
FIG. 12 Gene therapy for a mouse model of Sandhoff disease. (a) hexb gene expression in neuronal tissues. $1 \times 10^8$ vp of various fiber-modified HDAd vectors were injected into hexb−/− mice through subarachnoid space at lumbar level and neuronal tissues were isolated for extraction of cellular RNA 8 weeks after injection. The hexb mRNA was quantified by real time RT-PCR and relative hexb mRNA expression to that in brain of hexb+/+ mice was calculated. *$P<0.001$, **$P<0.05$. (b-d) Hexosaminidase (Hex) activities (total in b, Hexosaminidase A (HexA) in c and Hexosaminidase B (HexB) in d) in nervous tissues from hexb+/+ and hexb−/− mice with injection. HexB activity was calculated by subtracting hexA activity from total hex activity. *$P<0.001$, **$P<0.01$. †$P<0.01$ and ††$P<0.05$ vs. hexb−/− treated with HDAd-empty. (e-h) Immunofluorescence for Hexb protein in DRG. (i-l) In situ staining for hexosaminidase activity. Nuclear was stained with methyl green. Arrows indicate weak positive staining in neurons. Bar, 20 μm.
Figure 12:
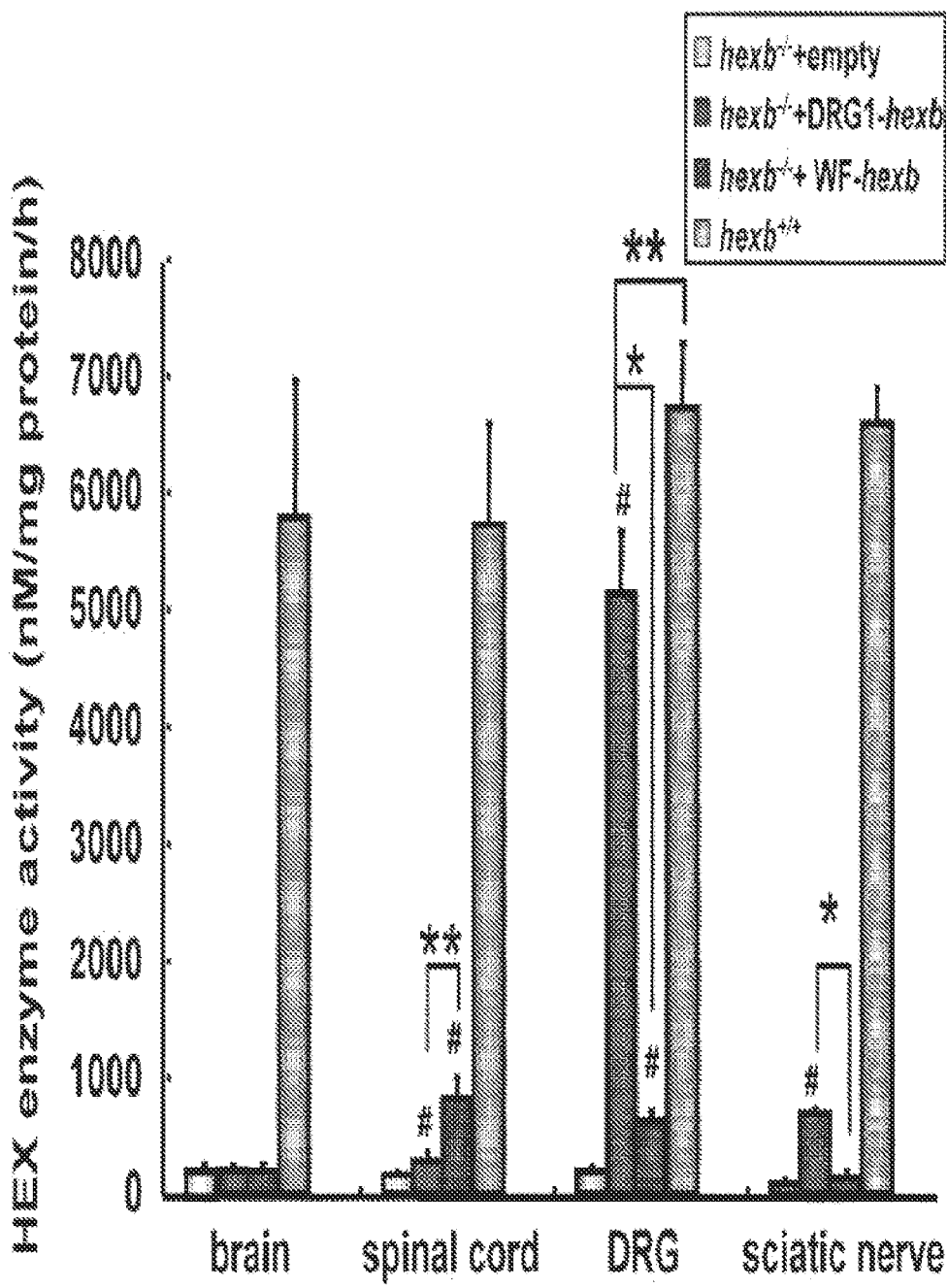
Figure 12:
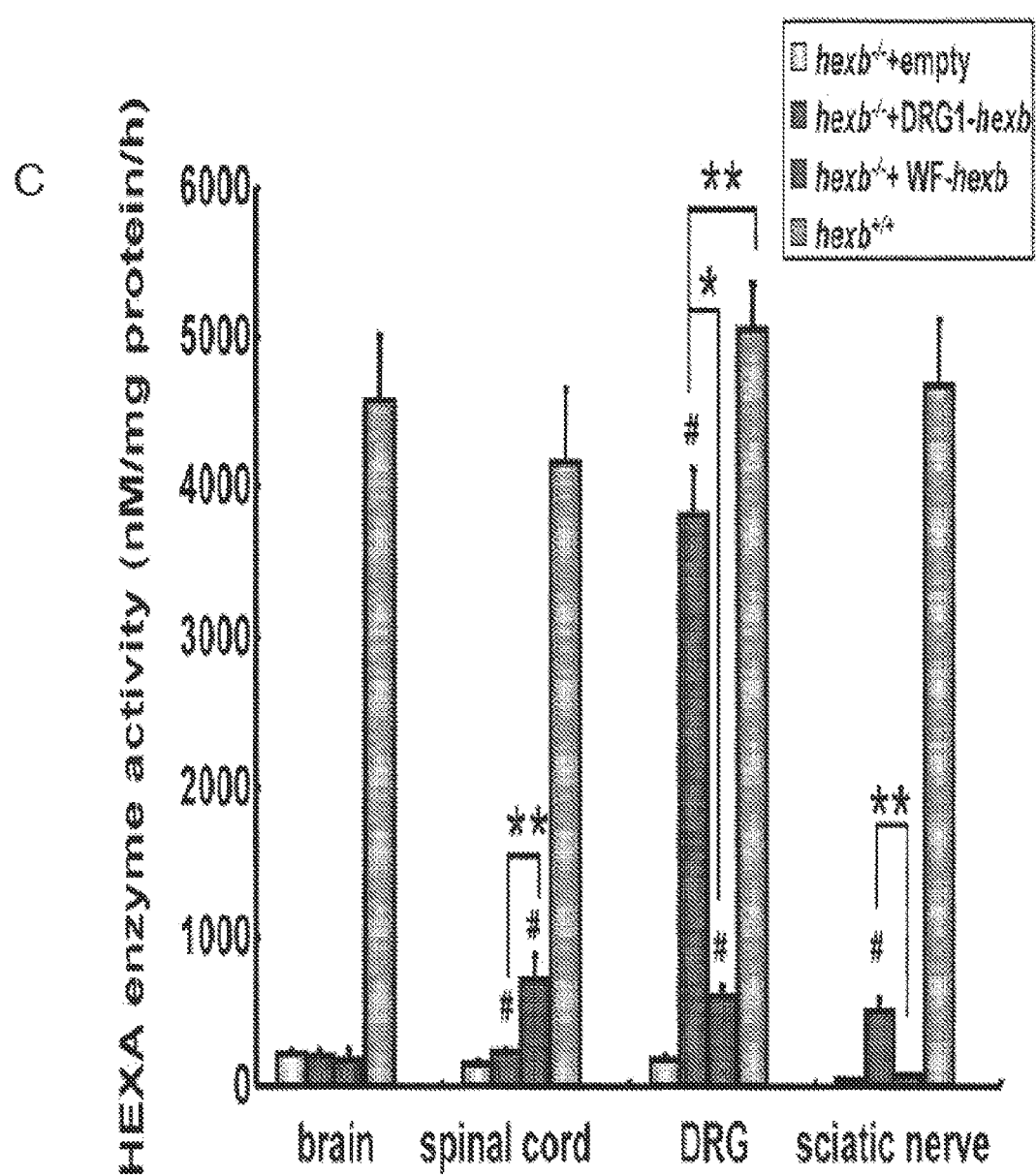
Figure 12:
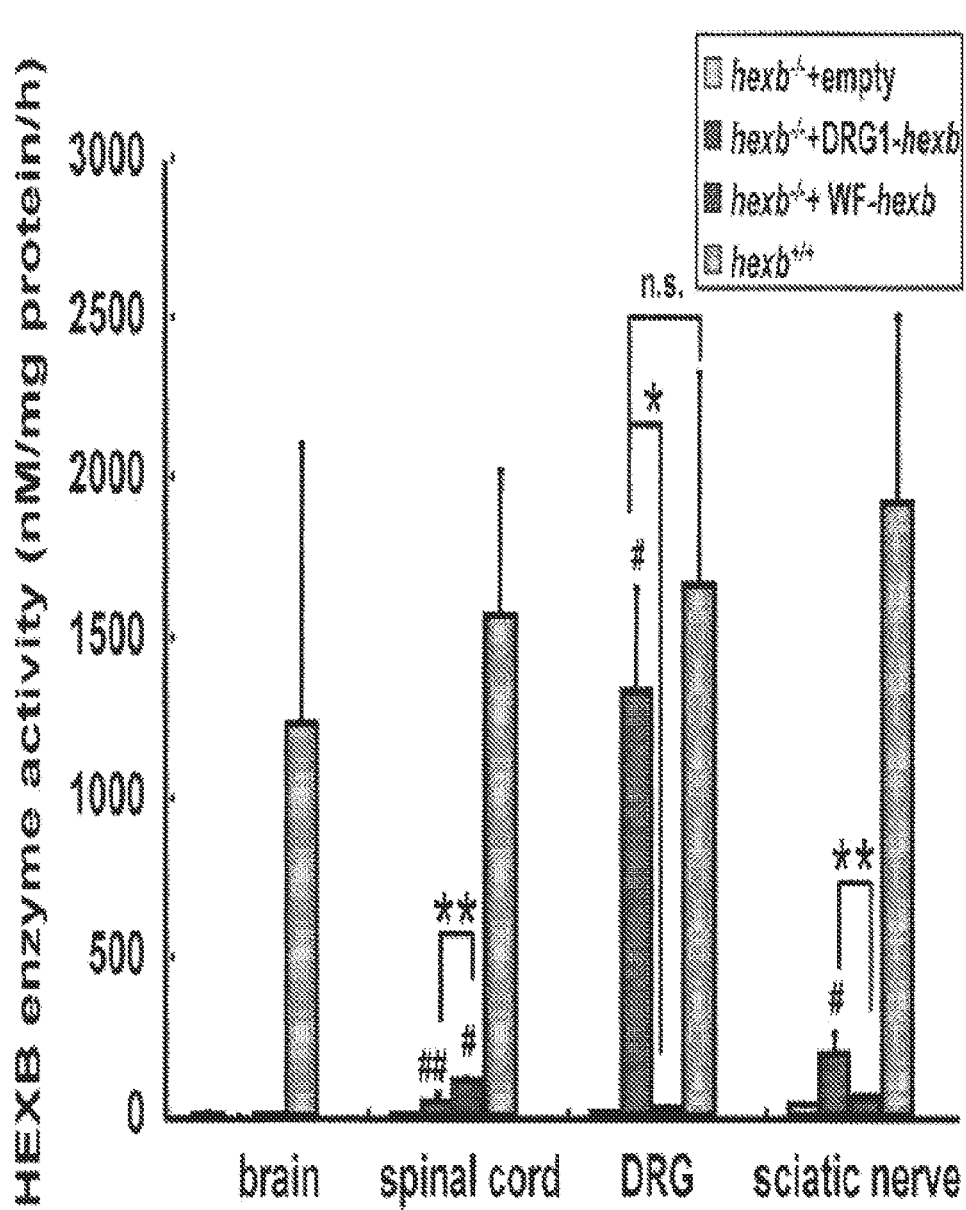
Figure 12:
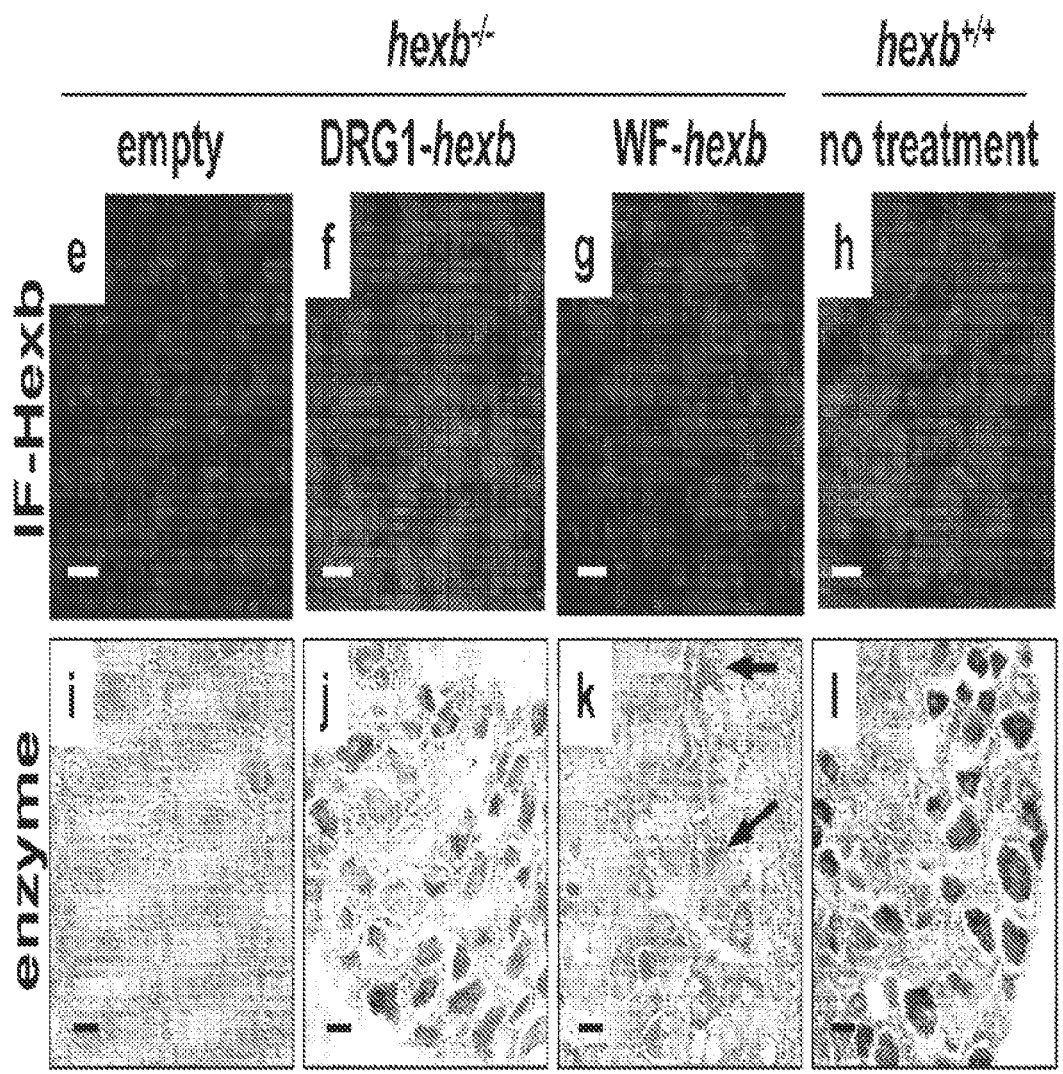
Figure 13:
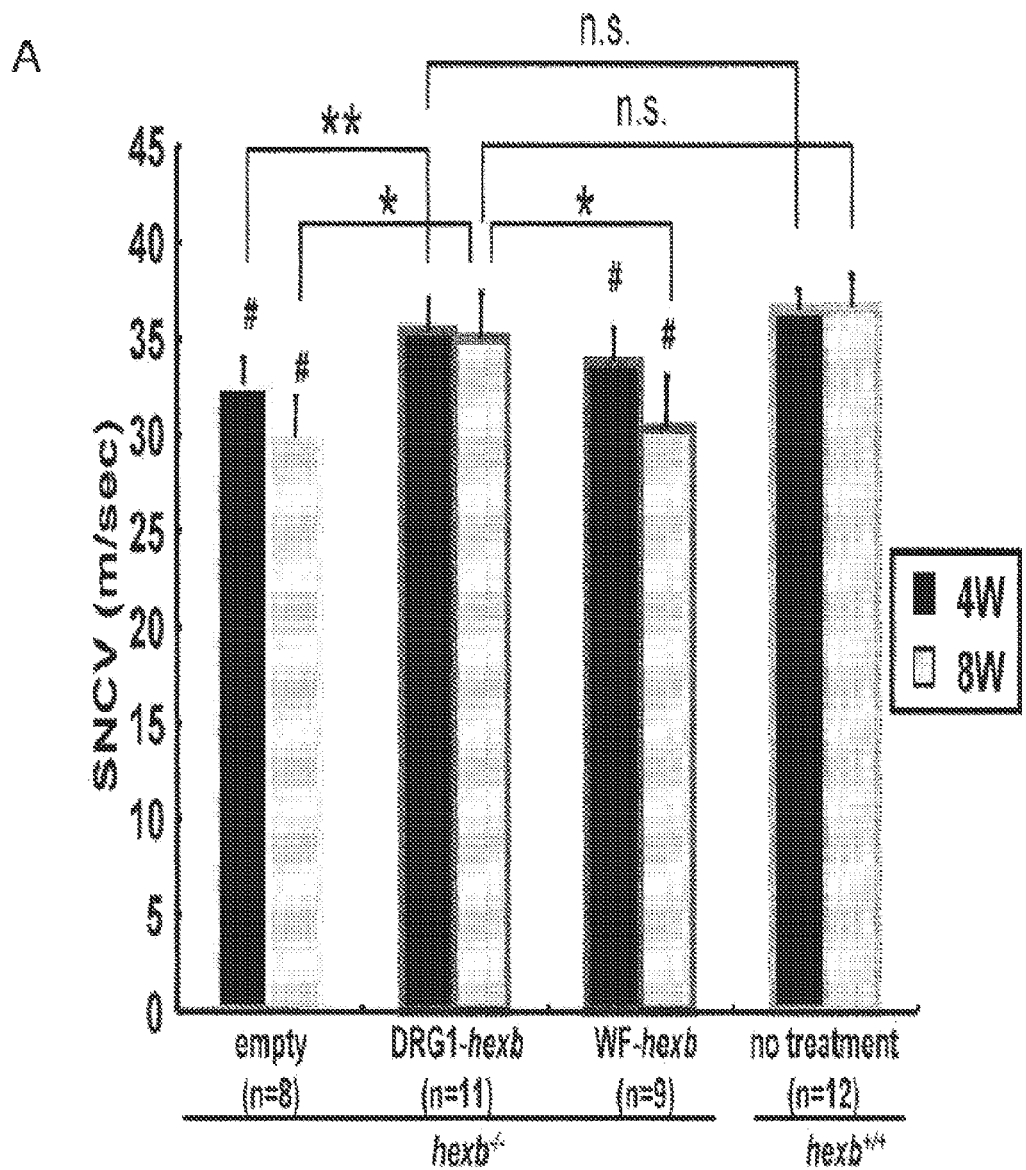
FIG. 13 DRG-targeted hexb expression rescues sensory neuronal responses in hexb−/− mice. Electrophysiological studies and behavior tests were performed at 4 and 8 weeks after treatment. (a) Sensory nerve conduction velocity was measured on sural nerve. (b) Sensory nerve action potential was recorded in proximal site after stimulation in the distal site at ankle joint. (c) First contact time. (d) Adhesive removal test. Data are expressed as means±S.D. (n=8-12). *$P<0.01$, **$P<0.05$. †$P<0.01$ and ††$P<0.05$ vs. hexb+/+ mice. (e-h) Nissl stain. (i-l) PAS stain with hematoxylin for nuclear stain. (m-p) Enlargement of black square in i-l. Arrows indicate granular formations in neurons. Bar, 20 μm.
Figure 13:
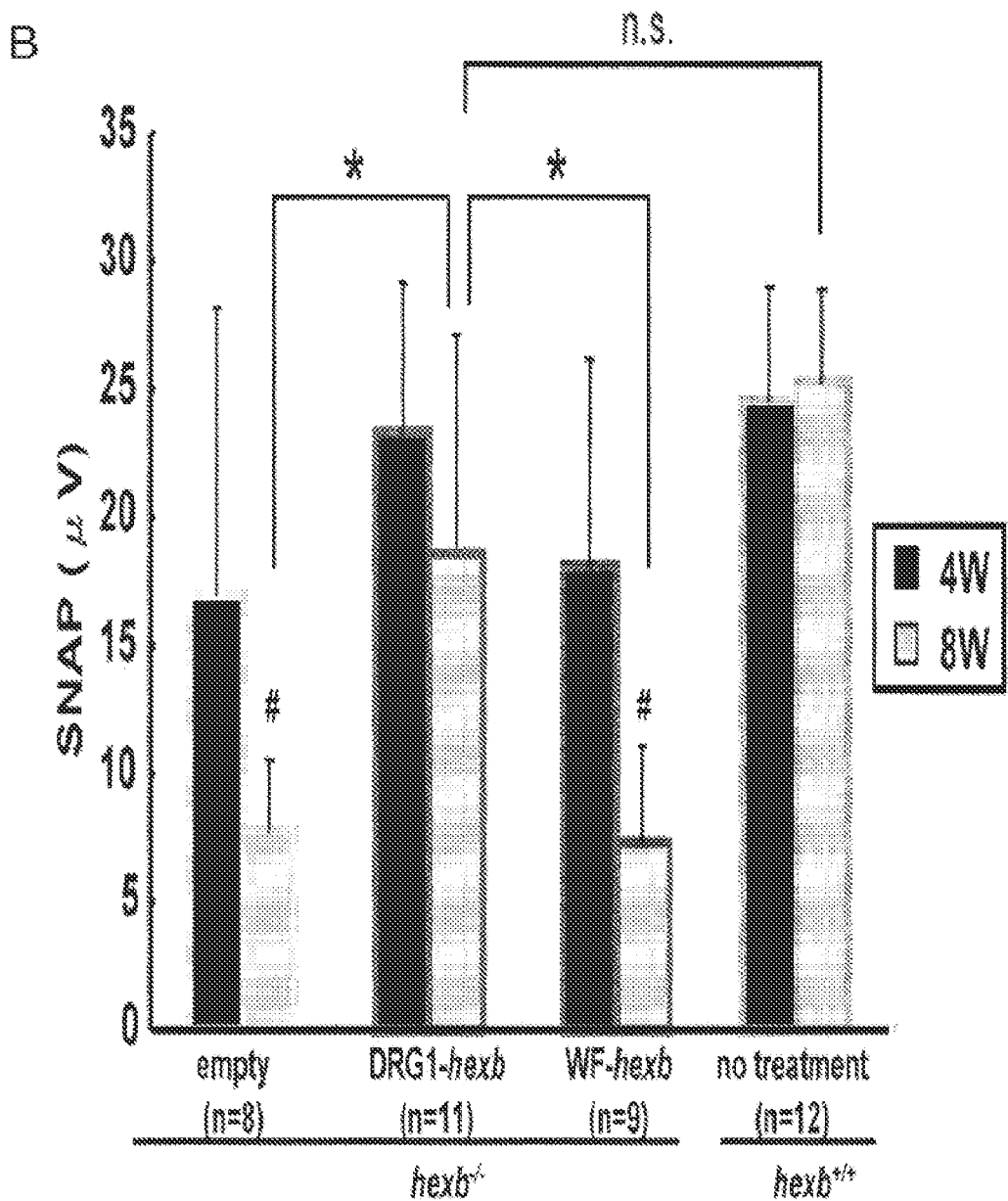
Figure 13:
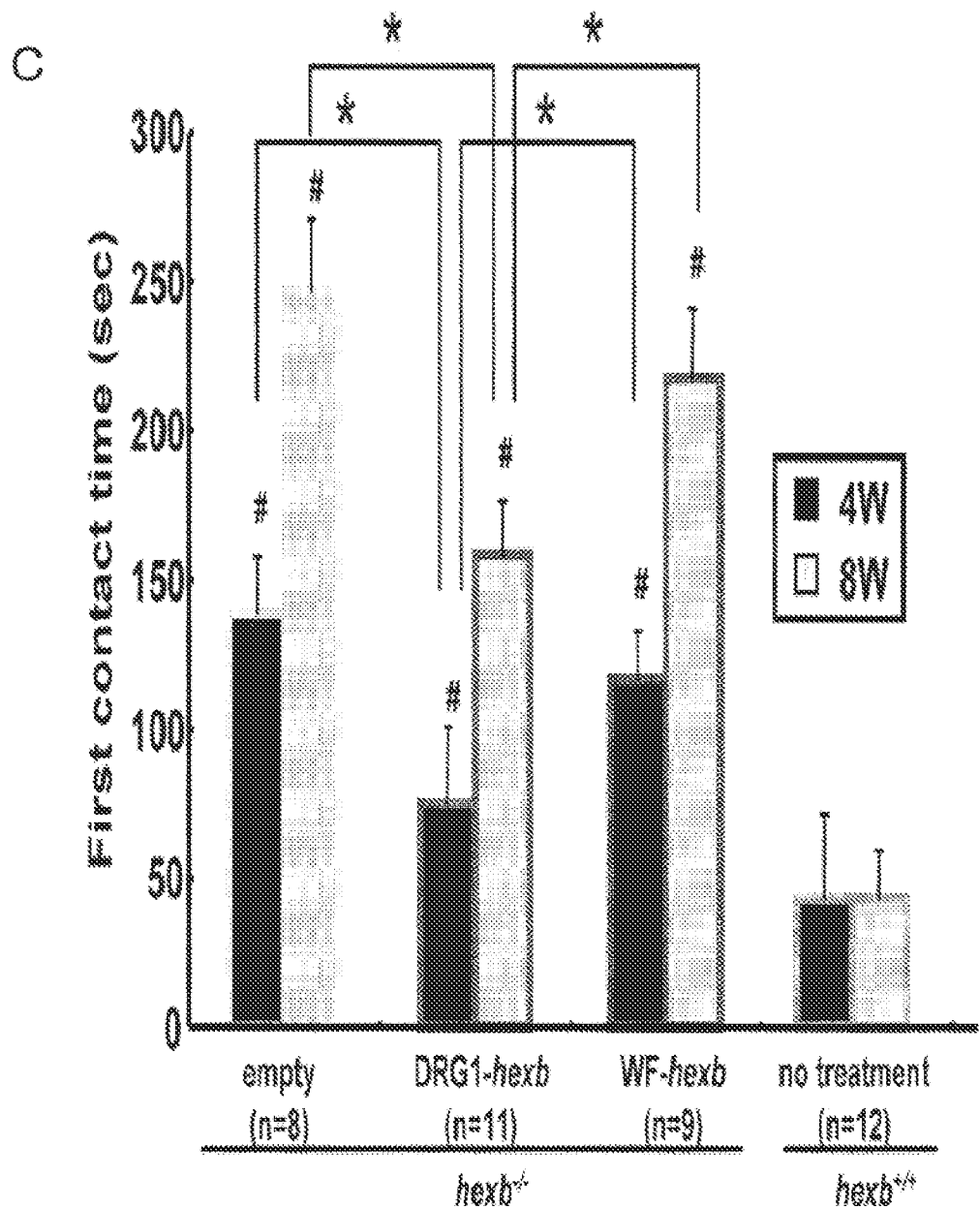
Figure 13:
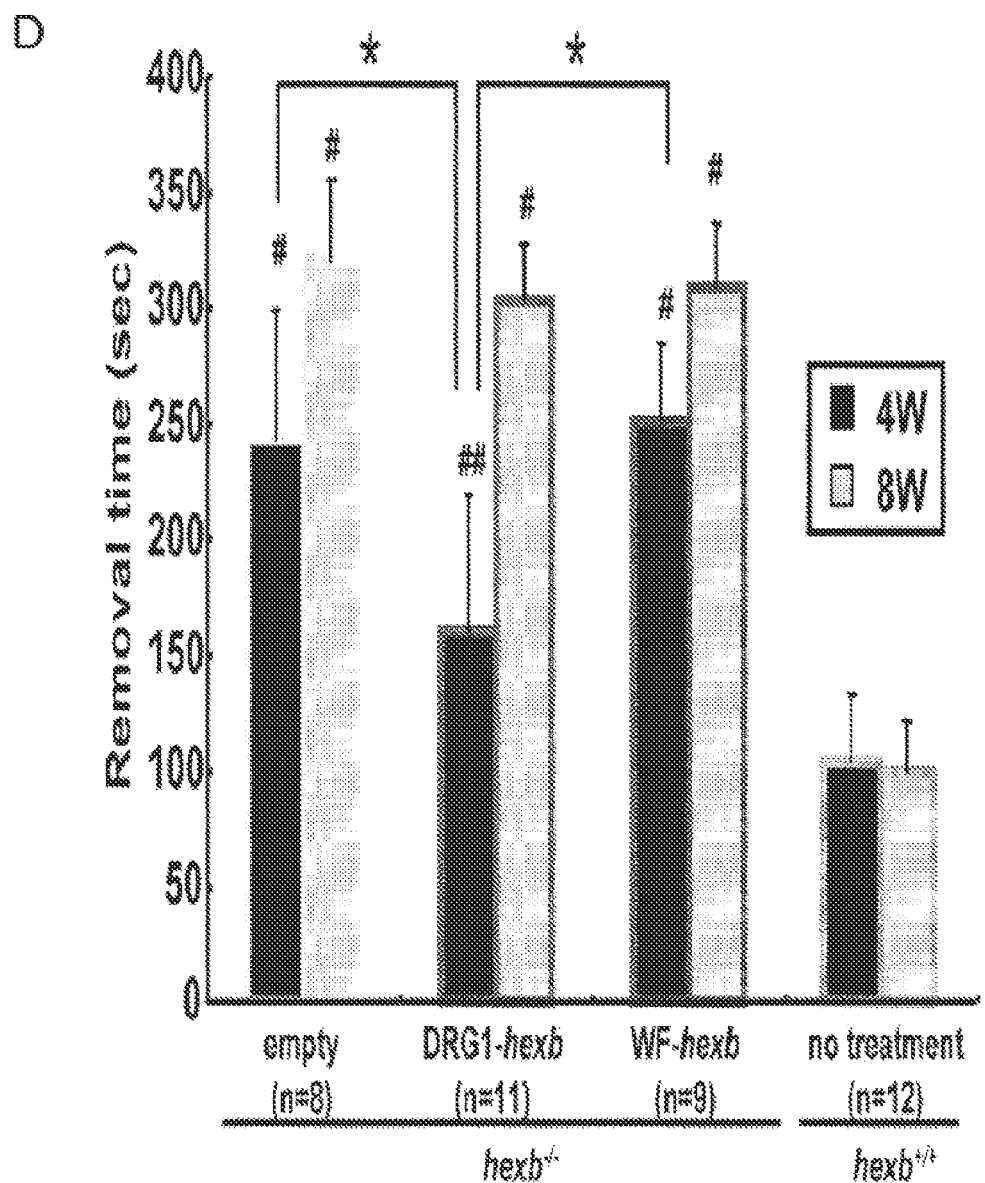
Figure 13:
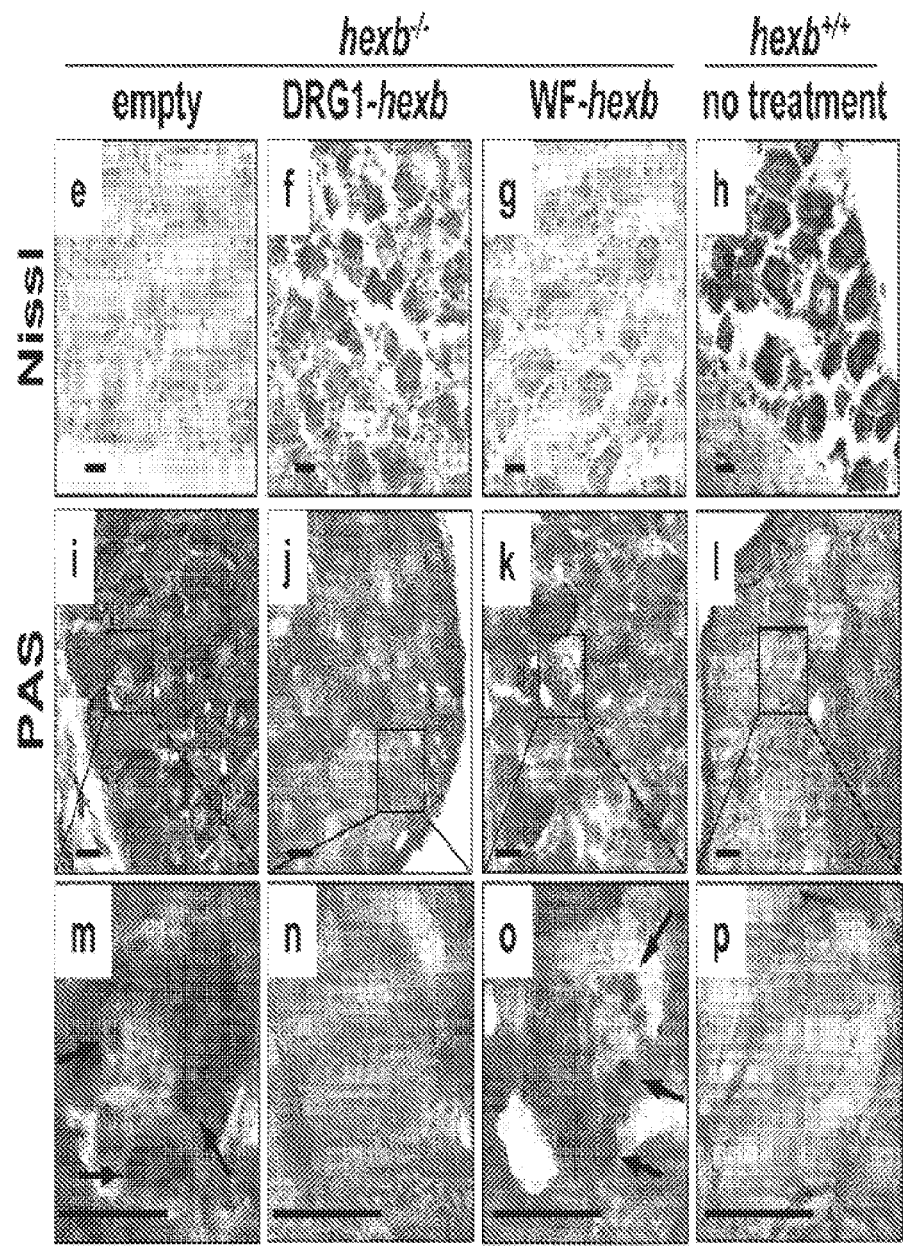
Figure 14:
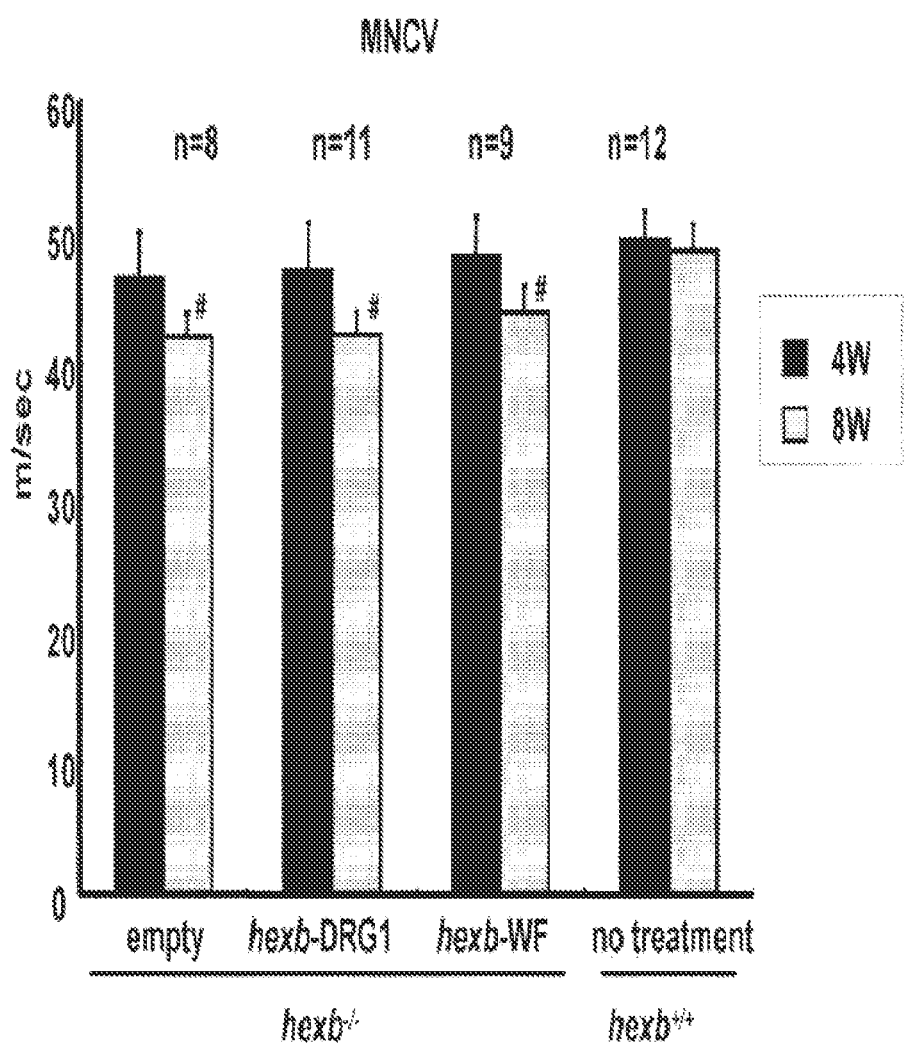
FIG. 14 Motor nerve conduction velocity (MNCV) and compound muscle action potential (CMAP) in hexb−/− mice after treatment with fiber-modified HDAd expressing hexb. (a,b) Measurement was performed at 4 and 8 weeks after injection. #$P<0.05$ vs. hexb+/+ mice (n=8-12).
Figure 14:
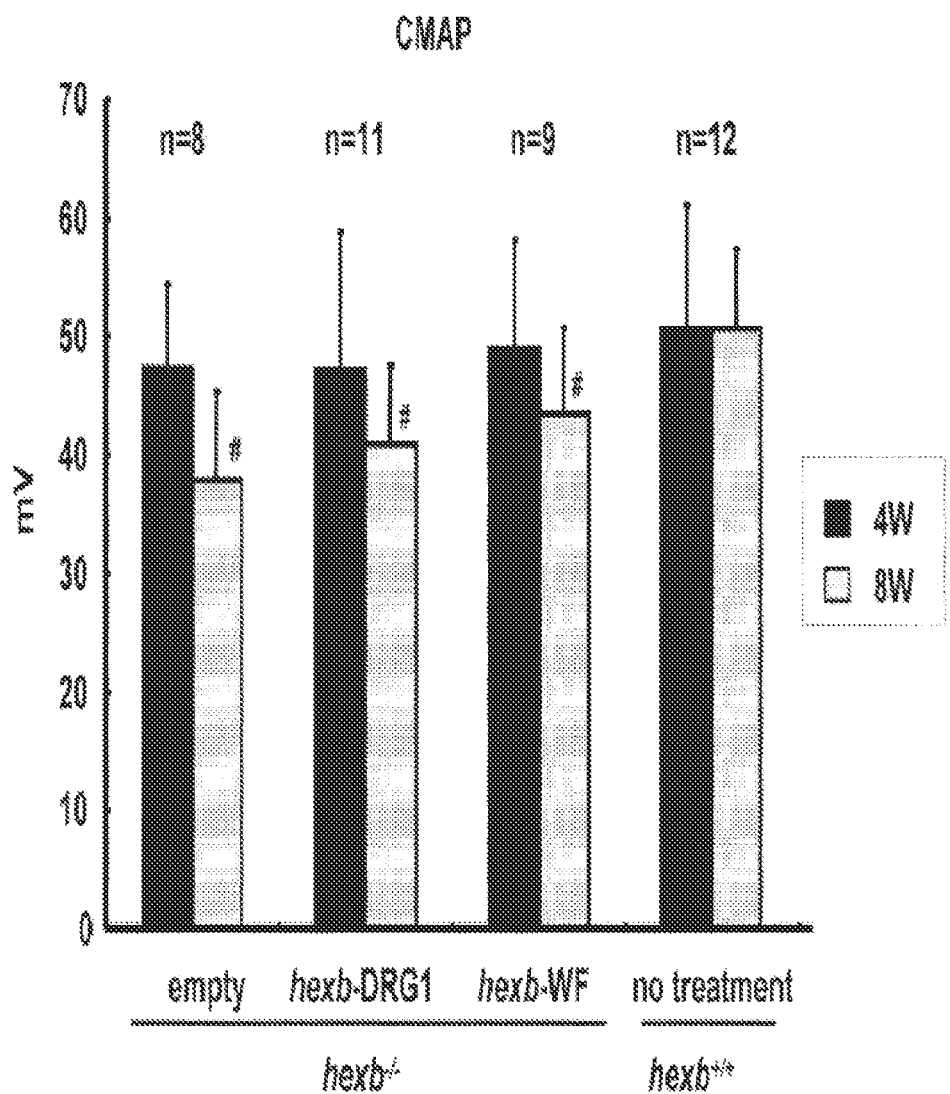

The effect of DRG neuron-targeted enzyme replacement was investigated on the abnormal histology and sensory neuronal impairment in hexb$^{-/-}$ mice. The inventors injected $1 \times 10^8$ vp of HDAd vectors expressing hexb driven by the EF-1 promoter into the subarachnoid space of hexb$^{-/-}$ mice at 4 weeks of age and measured mRNA level and enzyme activity in nerve tissues 8 weeks later. An empty vector was used as control. In hexb$^{-/-}$ mice, all neural tissues expressed hexb mRNA, empty vector-treated hexb$^{-/-}$ mice displayed no detectable hexb mRNA, while hexb$^{-/-}$ mice treated with HDAd-DRG1-hexb (DRG1-hexb) expressed hexb mRNA almost exclusively in DRG, at a level that was significantly higher than wild type mice (FIG. 12a). The wild type fiber HDAd (WF-hexb) produced hexb mRNA in brain and spinal cord at a level that was substantially lower than that in wild type mice. Hex A is a heterodimer of α and β subunits and Hex B is a homodimer of hexosaminidase β subunits. Expression of hexb rescues both Hex A and Hex B activities in hexb$^{-/-}$ mice. After treatment, total Hex and Hex A activities in DRG increased to 75-76% of those in wild type mice (FIG. 12b,c), and Hex B activity was similar to that in wild type mice (FIG. 12d). The small discrepancies between mRNA level and enzyme activities were probably attributed to the suboptimal ratio of the two subunits. As in wild type mice, hexb protein expression in DRG neurons in DRG1-hexb-treated hexb$^{-/-}$ mice was confirmed by immunofluorescence, which showed that most DRG neurons were positive for Hexb (FIG. 12f,h). In contrast, immunofluorescence staining was totally absent in the empty vector group and barely detectable in the WF-hexb-treated DRG (FIG. 12e,g). Histochemically, Hex enzyme activity was revealed in the section in situ by a purple-brown coloration resulting from diazonium coupling between fast Garnet GBC and the products catalyzed from naphtol-AS-BI-D-N-acetyl-β-glucosaminide by hexosaminidase. In agreement with enzyme activity, the histochemical stain in DRG1-hexb treated mice was present at a level similar to that in hexb$^{-/-}$ mice, while mice treated with WF-hexb exhibited much lower coupling and those with the empty vector displayed no evident coupling (FIG. 12i-l). Sandhoff disease is a serious gangliosidosis that affects both the central and the peripheral nervous systems and is associated with a much shortened lifespan (mice at 16-20 weeks of age had to be euthanized because of severe debilitating motor dysfunction.) DRG1-hexb treatment did not extend the time until euthanasia. However, progression of objective measures of DRG function was markedly improved by the treatment. The DRG1-hexb group maintained intact sensory nerve conduction velocity (SNCV) at a normal level 4 and 8 weeks after treatment, while mice treated with empty or WF-hexb group exhibited significantly impaired SNCV (FIG. 13a). Unlike the intact SNCV at 8 weeks in mice treated with DRG1-hexb, the motor nerve conduction velocity (MNCV) deteriorated at similar rates in all treatment groups compared to untreated wild type controls (FIG. 14a). Sensory nerve action potential (SNAP) deteriorated markedly in empty vector-treated hexb$^{-/-}$ mice at 8 weeks after treatment (12 weeks of age). DRG1-hexb treatment group maintained their SNAP at the same level between 4 and 8 weeks, whereas WF-hexb-treatment failed to slow down the progressive impairment of SNAP in hexb$^{-/-}$ mice (FIG. 13b). In contrast, none of the different HDAd treatments could slow down the deterioration in compound muscle action potential (CMAP) in any of these animals (FIG. 14b).

A functional neurological behavior test was performed by measuring the time needed for the mice to remove an adhesive tape on their hindpaw (Fleming et al., 2004). In hexb$^{-/-}$ mice, the time of first contact for tape removal goes up progressively with age. Treatment with WF-hexb had no effect on first contact time while DRG1-hexb treatment significantly shortened this time and slowed down the deterioration in this parameter (FIG. 13c), at 4 and 8 weeks. The time required for successful tape removal was also improved by DRG1-hexb, but not WF-hexb, at 4 weeks; however, the beneficial effect of the treatment on this parameter, which depends also on relatively intact motor function, disappeared after 8 weeks (FIG. 13d).

The structural integrity of DRG neurons was characterized histologically 8 weeks after vector injection. By Niss1 staining, DRG neurons in hexb-/- mice treated with DRG1-hexb were similar to those in wild type mice, though the staining in hexb-/- mice was slightly less intense than for wild type mice (FIG. 13f,h). This is consistent with the results of enzyme histochemistry shown in FIG. 12. In contrast, DRG neurons in the empty or WF-hexb group showed much lighter staining, suggesting neuronal degeneration (FIG. 13e,g). In periodic acid Schiff (PAS) staining, granular formation (FIG. 13i,m,k,o, arrows) was evident in many DRG neurons in mice treated with the empty or WF-hexb vector, while such accumulation of carbohydrate macromolecules was not detected in the DRG1-hexb-treated or hexb$^{-/-}$ group (FIG. 13j,n,l,p).

Example 7

Significance of Certain Embodiments of the Invention

Sensory neuronopathies affecting DRG neurons that manifest as pain, hyperalgesia, hypo- and anesthesia or ataxia can be caused by genetic, nutritional, metabolic, inflammatory or neoplastic processes. A strategy that enables the efficient delivery of therapeutic transgenes specifically to DRG neurons would represent a significant advance in the treatment of DRG neuronal disorders, because therapeutic measures aimed at the underlying disease process only often fails to reverse the neuronopathy (Sghirlanzoni et al., 2005; Kuntzer et al., 2004).

In an exemplary embodiment of the invention, this problem was addressed by engineering fiber-modified HDAd that specifically targets DRG neurons in vivo. HDAd was selected as the vector because of its large capacity, negligible toxicity, prolonged transgene expression in the absence of integration which minimizes its potential tumorigenic effects (Oka and Chan, 2005). The target tissue specificity of an HDAd is determined by the specificity of the helper virus (HV). By using a HV ablated for binding to primary attachment receptors in the fiber (KO1S* mutation) as a platform, the inventors inserted into the HI loop DRG neuron-homing peptides isolated by phage display and biopanning (Oi et al., 2008). Mutations were introduced in CAR and putative HSPG binding sites that detargeted Ad from 293 cells (Kritz et al., 2007 and DRG neurons. When Ad was into the subarachnoid space, modified Ad was also detargeted from DRG neurons in vivo. For subgroup C Ad, including Ad5, infection of Ad in vitro occurs first by direct attachment of the fiber to the CAR, followed by internalization through aV integrin via the RGD motif of penton bases, or by interaction with HSPG (Dechecchi et al., 2001). However, IV Ad5 directly binds to coagulation factors via interaction between the FX Gla domain and hypervariable regions of the Ad5 hexon surface (Waddington et al., 2008; Kalyuzhniy et al., 2008), and is subsequently internalized by binding to LRP and/or HSPG in the liver (Shayakhmetov et al., 2005; Parker et al., 2006). Koizumi et al. have reported that Ad ablated for binding to CAR, aV integrin and HSPG within the FG loop in the fiber knob, and Ads that carry a mutation of the AB loop and substitution of the fiber shaft derived from Ad type 35 have markedly reduced tropism to the liver; the modifications also attenuated the toxicity as defined by IL-6 secretory response after IV injection (2006). The penton and the RGD motif were left intact, as the RGD motif was thought to be needed for endocytosis and endosomal escape (Wickham et al., 1993; Shayakhmetov et al., 2005). Ablation for CAR and HSPG was sufficient to blunt natural tropism. In specific embodiments of the invention, the direct subarachnoid delivery of the vector, a routine procedure in clinical practice that also eliminates any direct interaction of Ad with blood components, is useful.

Chronic toxicity associated with early generation Ads has been largely eliminated in HDAd; however, the acute inflammatory response caused by innate immunity against capsid proteins was reported to be similar among the different types of Ad40. In certain embodiments of the present invention, markedly reduced IL-6 and TNF-α levels were identified after intrathecal HDAd. It is intriguing that the IL-1β response was not greatly attenuated by HDAd as compared with the HVs. An increase in IL-1β is an early response to both Ad and HDAd (McCaffrey et al., 2008) and is considered upstream to IL-6 and TNF-α. Intrathecal HDAd has been reported to invoke neither systemic or local toxicity, nor a CNS-specific immune reaction (Butti et al., 2008). Therefore, the low toxicity found in specific embodiments of the invention are in part due to presence of few immune cells in CSF, in certain aspects. In addition, use of detargeted HDAd-KO1 S* and HDAd-DRG1 (which is also based on KO1S*) was associated with a 2-fold reduction of IL-6 at 3 and 24 h after vector injection, an observation consistent with previous reports showing attenuated cytokine response by Ad detargeted for natural receptors (Koizumi et al., 2006).

Three exemplary peptide ligands were tested for their ability to target DRG neurons. Although surface proteins interacting with these peptides have not been identified, DRG1 and DRG3 appear to bind to small neurons while DRG2 binds to large neurons (Oi et al., 2008), in certain aspects of the invention. HVs containing these peptide ligands increased the efficiency of transduction of DRG neurons in vitro as well as in vivo (FIG. 4). DRG1 was the most potent and transduction of DRG neurons by HV-DRG1 was more than 100-fold more efficient than HV-WF. This DRG targeting HV had a profound effect on transgene expression. LacZ expression induced by HV-DRG1 at day 60 was still maintained at a level similar to that by HV-WF at day 5. Despite an enhanced transduction efficiency of the targeting vector, there was no apparent effect of targeting on decay of transgene expression (FIG. 10a). This is not unexpected, however. Although tissue or cell targeting plays an important role in efficient transduction, it does not influence intracellular processing or degradation of vector chromosome. Phage display is a powerful technique to identify homing peptides to specific in vivo molecular zip codes. DRG1 appears to support vector internalization and endosome escape, which does not always happen (Fechner et al., 1999). Phage is a small molecule compared to Ad and the access of bulky Ad particle could be hampered by physical and biological barriers (Fechner et al., 1999). In fact, although IT HV-DRG1 efficiently transduces DRG neurons, IV HV-DRG1 fails transduce DRG neurons in vivo.

Despite the many human diseases affecting DRG neurons, few mouse models of pure sensory neuron dysfunction are available. hexb−/− mice were used, which exhibits global neurological impairment at 3 months, followed by ataxia, bradykinesia, impaired motor activity and balance. By 18 weeks, hind-limb movement is lost and they die before 20 weeks (Sango et al., 1995; Sango et al., 2002). As in vivo measurements of sensory function have not been reported in this mouse model, the occurrence of peripheral sensory impairment in this disorder was first documented using sensory nerve conductions studies and mixed sensory/motor function (tape removal) tests (FIG. 13c,d). A single injection of DRG neuron targeting HDAd expressing Hexb by lumbar puncture into the CSF increased Hex activity in DRG neurons and restored peripheral sensory function but not motor neuron function in hexb−/− mice. In histological analysis, Hexb immunoreactive protein was readily detected in DRG neurons of mice treated by HDAd-DRG1-hexb but not those by HDAd-WF-hexb. Very few PAS+ granular formation in the cell body (representing ganglio side accumulation) was seen in the HDAd-DRG1-hexb-treated mice. Niss1 stain was strongly positive in HDAd-DRG1-hexb group similar to that seen in hexb+/+αmice. It is important to note that HDAd-DRG1-hexb treatment conferred protection to sensory neuron function but had no detectable effect on motor nerve function. When nerve function was assessed by the tape removal test, deterioration in first contact time was significantly improved by the treatment at both 4 and 8 weeks, because sensory function was dominant in this behavior test. In contrast, the tape removal time, which is determined by a combination of sensory and motor functions, was partially corrected only at 4 weeks but not at 8 weeks. Despite a marked improvement in sensory nerve conduction, the behavior tests were still quite abnormal because performance in these tests requires the presence of intact peripheral and central nervous systems and the treatment had no effect on the latter. Therefore, use of the hexb−/− mice enabled one to show that DRG neuron targeted gene therapy specifically restores DRG function without affecting motor nerve, spinal cord or brain function.

There are many clinical applications of the present invention. Neuropathic pain occurs commonly among patients with various metabolic and inflammatory disorders. For example, diabetic neuropathy is the most common chronic complication of diabetes, affecting millions of people in the United States (Sadosky et al., 2008). Many of these individuals suffer neuropathic pain caused by sensory neuron dysfunction (Yasuda et al., 2003). Patients with ganglionopathies caused by autoimmune diseases or drug toxicities also commonly experience severe neuropathic pain (Kuntzer et al., 2004). Treatment of these and other sensory neuronopathies by intrathecal DRG-targeting HDAd that express neurotrophic factors or analgesic peptides is a useful application of the invention. It has been reported that the immune response to foreign material injected IT is attenuated, which may allow for the repeat administration of HDAd via this route for repeated treatments (Muruve et al., 2004; Butti et al., 2008). HDAd can be administered repeatedly even when it is given by the IV route, as long as one employs HVs of different serotypes (Kim et al., 2001; Morral et al., 1999). Finally, the non-integrating nature of HDAd is an advantage in that it minimizes the chance of genotoxicity and induced tumorigenesis (Oka and Chan, 2005).

In the present invention, there are methods and compositions for a new strategy to produce HDAd that specifically target DRG neurons. One advantage of this approach is that HDAd expressing therapeutic gene made by a generic HV can be retargeted to tissues or cell types of interest by amplification with HV containing targeting ligands. HDAd and fiber-modified HV are separately produced and combined only at the final amplification step. In certain aspects of the invention, one can customize HDAd delivery to treat specific diseases and organ systems. Clinical trials using early generations Ads have been ongoing for years (Tolcher et al., 2006; Chiocca et al., 2008).

Example 8

Exemplary Methods and Materials

Cell culture. To generate Ad5 wild type fiber expressing 293 cells (293-fiber), lentiviral vector mediated gene transfer was employed. Ad5 fiber was subcloned by PCR from AdEasy vector using the following primers: 5' upstream primer, 5'-GGATCCGCCACCATGAAGCGCGCAAGAC- CGTC-3' (SEQ ID NO:88) and 3' downstream primer, 5'-GCGGCCGCTTATTCTTGGGCAATGTATG-3' (SEQ ID NO:89). They contained artificial cloning sites (underlined) and the Kozak sequence (bold faced). The Ad5 fiber cDNA was then subcloned into the pHIV-EF-1-puro (a first generation SIN vector modified from pHIV-AP; Sutton et al., 1998). LV-Ad5-fiber was produced by cotransfection of LV shuttle vector and pME-VSVG into 293T cells by standard calcium phosphate precipitation method (FIG. 5a). 293-fiber cells were established by selection on puromycin (1 µg/ml). 293, 293-fiber and 293Cre66 cells were maintained in α-MEM supplemented with 10% FBS and antibiotic-antimicotics (Invitrogen). Puromycin (1 µg/ml) and G418 (0.8 mg/ml) were included in the media for 293-fiber and 293Cre66, respectively. DRG neurons were isolated from C57BL/6 mice one day before experiments and cultured under F-12 with 10% FBS as previous described (Oi et al., 2008). Infection was performed in non-serum media at 37° C. for 30 min-1 hour in a $CO_2$ incubator.

Figure 15:
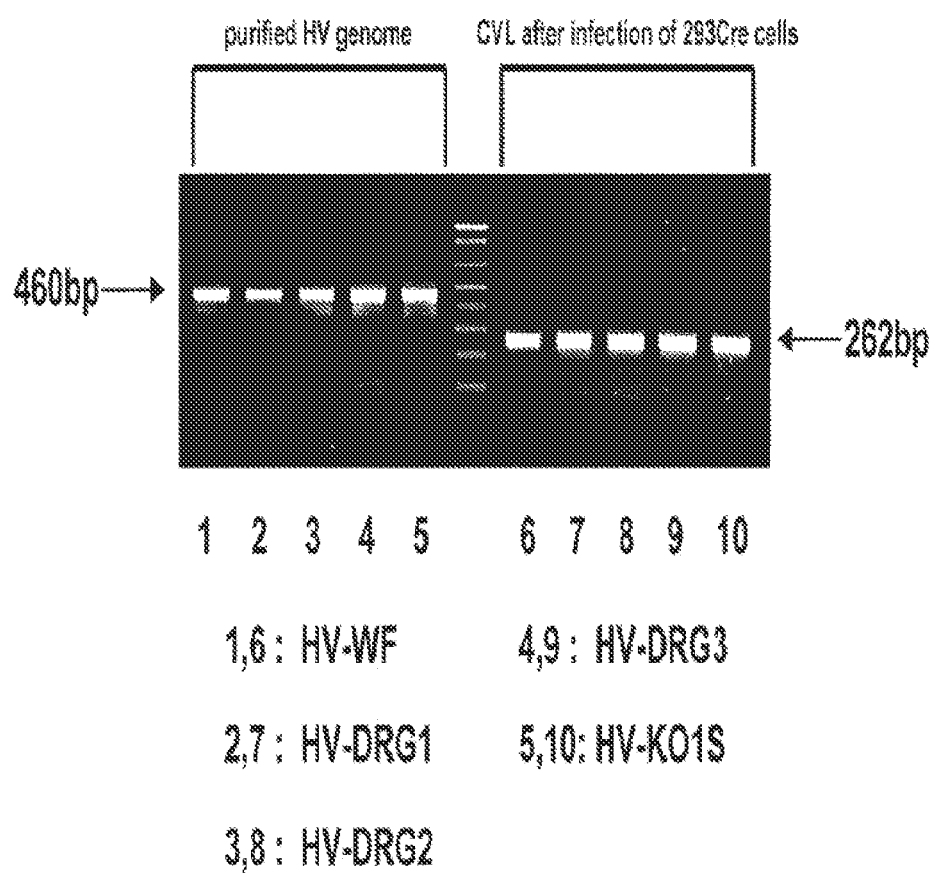
FIG. 15 PCR analysis for excision of the packaging signal from helper virus. (a) Excision of the packaging signal upon infection of 293Cre cells. Left panel: PCR of purified HV genome. PCR was performed using the following primers corresponding to 5' and 3' flanking sequence to the packaging signal: 5'-primer; 3'-primer. The expected PCR product is 460 bp. Right panel: HV genome extracted from CVL after infection of 293-cre cells. Due to excision of the packaging signal, the size of PCR product is reduced to 262 bp. (b) Nucleotide sequence of HV genome before (upper panel) and after (lower panel) infection of 293-cre cells. See Erturk et al. (2003).
Figure 15:
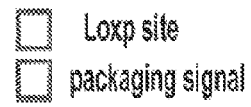
Figure 15:
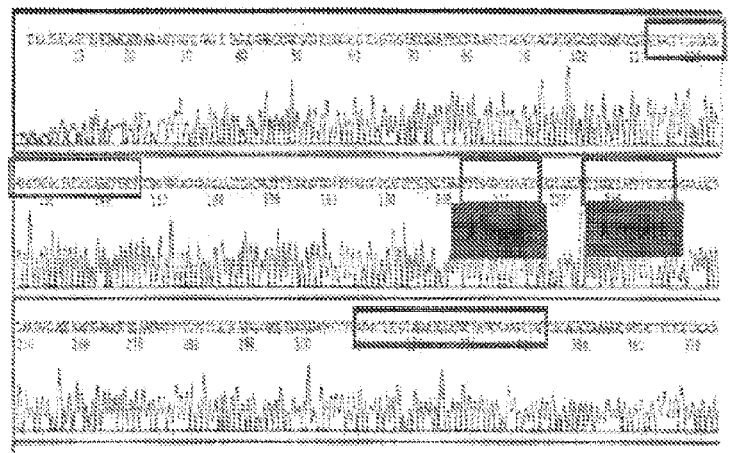
Figure 15:
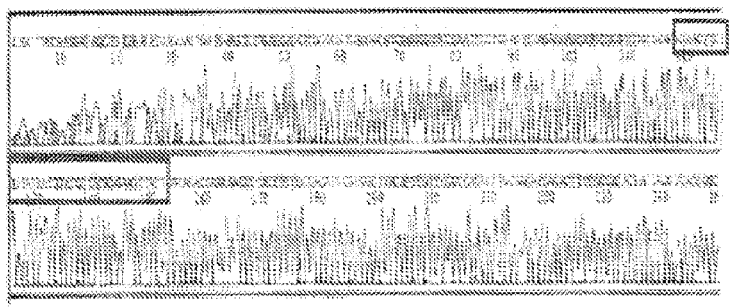

Construction of fiber-modified first generation helper virus (HV). To construct fiber-modified HV using AdEasy system (Stratagene) (FIG. 3a), a 2-kb fragment containing 1.7-kb NdeI/PmeI fragment coding for Ad5 fiber was first subcloned into pCR2.1-TOPO (Invitrogen) by PCR using pDV153-KO1S* as a template (pCR2.1-fiber-KO1S*). pDV153-KO1S* is a derivative of pDV137, but harboring the S* mutation (mutation of the putative HSPG-binding region) and the unique BspEI site in the HI loop33 (FIG. 4a). Three exemplary peptide ligands targeting DRG neurons isolated by biopanning of phage display (Oi et al., 2008) were then subcloned into the BspEI site of pCR2.1-fiber-KO1S*, resulting in pCR2.1-DRG1, -DRG2 and -DRG3. The 1.7 kb NdeI/PmeI fragment was excised from these three vectors and pCR2.1-fiber-KO1S* and then subcloned into pDV153-KO1S* vector. The 7 kb SpeI/PacI fragment from these four clones were subcloned into pAdEasy-1 vector (Stratagene). To make fiber modified HV, the inventors modified pShuttle (Stratagene) to have the packaging signal (φ) flanked by loxP sites with the MluI site downstream of the second loxP site for cloning purposes (pShuttle-loxP-φ-loxP). To insert two reporter genes in HV, the inventors first subcloned both 5.2 kb βgeo cassette and 2.2 kb BamHI/BglII fragment of RLCMV (Promega) containing Rluc expression cassette into pLPBL-1. The resulting dual gene expression cassette was excised by AscI digestion and subcloned into the MluI site of pShuttle-loxP-φ-loxP (pShuttle-loxP-φ-loxP-βgeo-RLCMV). HV plasmids were generated by homologous recombination in BJ5183 cells (Stratagene). HVs targeting DRG neurons (HV-DRG1, -DRG2 and -DRG3) and detargeted HV (HV-KO1S*) were produced by transfection into 293-fiber cells. HV-WF was produced on 293 cells. After production of HVs, these were tested the excision of the packaging signal by 293-Cre cells. Infection of 293-Cre with HVs removed the packaging signal, resulting in 262 bp PCR product instead of 460 bp product from the intact HV (FIG. 15a). The excision of the packaging signal was also confirmed by DNA sequence analysis (FIG. 15b).

Construction of helper-dependent adenoviral (HDAd) vectors. The cDNA of cre recombinase was cloned by PCR using pBS185 vector (Invitrogen) as template and the following PCR primers: 5' upstream primer, 5'-TTAATTAAGCCAC-CATG TCCAATTTACTGACCGTACAC-3' (SEQ ID NO:90) and 3' downstream primer, 5'-GCGGCCGCCTAATCGCCATCTTCCAGCAG-3' (SEQ ID NO:91). They contained artificial cloning sites (underlined) and the Kozak sequence (bold faced). The hexb cDNA was cloned from C57BL/6 mouse brain into pCR2.1-TOPO (Invitrogen) by RT-PCR using the following primers: 5' upstream primer, 5'-ATGCCGCAGTCCCCGCGTA-3' (SEQ ID NO:92) and 3' downstream primer, 5'-CTGGAATGCTG-TAGACGTCTGTC-3' (SEQ ID NO:93). These cDNAs were subcloned into pBOS vector that contains EF-1 promoter and rabbit β-globin polyadenylation signal on pLPBL-1 backbone. These expression cassettes and βgeo-RLCMV described above were excised by AscI digestion and then subcloned into pΔ28 vectors (Oka et al., 2001). All HDAd vectors were first made by the published method using HV-WF and 293Cre66 cells (FIG. 5b) (Oka and Chan, 2005). Fiber-modified HDAd vectors were made by coinfection of HDAd vector and fiber-modified HV as outlined in FIG. 3.

Mice. 8-12 week old male C57BL/6 male, B6; 129-Gt (ROSA)26Sor$^{tm2Sho}$/J (Rosa-GFP) and hexb+/− mice, a model of Sandhoff disease were purchased from the Jackson Laboratory. Homozygous hexb−/− and wild-type mice (hexb+/+) were generated by mating hexb+/− mice and the litter mates were used for studies. Genotyping was carried out according to the protocol posted on the home page of The Jackson Laboratory. All animals were housed, fed water and mouse chow ad libitum, and maintained under a 12-h light and dark cycle. All experimental protocols were performed according to the guidelines of Institutional Animal Care and Usage Committee at Baylor College of Medicine.

Luciferase assay in vitro and in vivo. For in vitro studies, the inventors plated 293 cells and isolated DRG neurons from C57BL/6 mice one day before infection and infected with HVs at 1,000 viral particles (vp)/cell. Next day, cells were harvested in a lysis buffer supplied with the luciferase assay kit (Promega) and the lysates were assayed for luciferase activity as described in manufacture's protocol. For in vivo studies, $1\times10^8$ vp of each vector were injected into mice through subarachnoid space at lumbar level. Mice were euthanized 5 days after vector treatment and brain, spinal cord, DRG and sciatic nerve were isolated. Tissues were homogenized with lysis buffer and the supernatants were assayed for luciferase activity.

X-gal staining of cells and nervous tissues. For in vitro studies, cells were fixed with fixation solution supplied in beta-gal staining kit (Invitrogen) one day after infection and incubated with X-gal as per manufacture's protocol. For in vivo studies, mice were transcardiacally fixed with 4% paraformaldehyde one day after vector injection and isolated nervous tissues were incubated with X-gal for 4 hours. All tissues were observed under standard microscope and stereomicroscope. Several pictures for brain and spinal cord were combined to show the whole central nervous system. Subsequently, 10 µm thick cryosections were prepared.

Quantitative RT-PCR. Total cellular RNA was extracted by Trizol (Invitrogen) and treated with DNase I digestion. After reverse transcription using oligo dT, mRNA was quantified by real-time PCR using iQ SYBR Green Supermix (Bio-Rad). The following exemplary primers were used: Lac-Z; 5' upstream primer, 5'-GTTGCAGTGCACGGCAGATA-CACTTGCTGA-3' (SEQ ID NO:94) and 3' downstream primer, 5'-GCCACTGGTGGGCCATAATTCAATTCGC-3' (SEQ ID NO:95), cre-recombinase; 5' upstream primer, 5'-GCATTACCGGTCGATGCAACGAGTGATGAG-3' (SEQ ID NO:96) and 3' downstream primer, 5' GAGTGAAC-GAACCTGGTCGAAATCAGTGCG-3' (SEQ ID NO:97), GFP; 5' upstream primer, 5'-GCACGACTTCTTCAAGTC-CGCCATGC-3' (SEQ ID NO:98) and 3' downstream primer, 5'-GCGGATCTTGAAGTTCACCTTGATGCC-3' (SEQ ID NO:99), hexb; 5' upstream primer, 5'-ACAGTTGCA-GAAGCTCCTGGT-3' (SEQ ID NO:100) and 3' downstream primer, 5'-CCTCTATGAGGGAATCTTGGAG-3' (SEQ ID NO:101), β-actin; 5' upstream primer, 5'-GACGGCCAGGT-CATCACTAT-3' (SEQ ID NO:102) and 3' downstream primer, 5'-CTTCTGCATCCTGTCAGCAA-3' (SEQ ID NO:103). The detection was carried out with Mx3000P QPCR system (Stratagene) and the results were analyzed by MxProQPCR software (Stratagene). All data were normalized to β-actin.

Immunoblots. DRG and 293-fiber cells were lysed with RIPA buffer [150 mM NaCl, 2 mM EDTA, 1% nonidet P-40, 1% sodium deoxycholate, 0.1% sodium dodecyl sulfate (SDS), 50 mM NaF, 10 μg/mL aprotinin, 10 μg/mL leupeptin, 1 mM phenylmethylsulfonyl fluoride, 20 mM Tris-HCl buffer, pH 7.4] and were centrifuged at 12,000×g for 20 min at 4° C. to collect the supernatant. 20 μg of proteins were separated by 7.5-15% SDS-PAGE and were transferred to a polyvinylidene difluoride filter (Immobilon Millipore, Bedford, Mass.). The blots were incubated overnight at 4° C. with rabbit anti-Cre antibody (1:1000, Novagen), mouse monoclonal anti-GFP antibody (1:1000, Clontech) or anti-adenovirus fiber (1:1000, ab3233, Abcam). Immunoreactive proteins were detected by enhanced chemiluminescence (PIERCE Biotechnology) after incubation with either horseradish peroxidase-conjugated anti-rabbit immunoglobulin or anti-mouse immunoglobulin (1:2000, Bio-Rad).

ELISA for cytokines in CSF. Cerebrospinal fluid (CSF) was collected from cistern magna at 3h, 24h, 3 days, 7 days and 14 days after vector injection. IL-1β, IL-6 and TNF-alpha levels were determined using an ELISA kit (eBioscience).

Hexosaminidase enzyme assay. Total β-Hexosaminidase activity was measured using 4-methylumbelliferyl-2-acetamido-2-deoxy-β-D-glucopyranoside (4-MUG; Sigma, St. Louis, Mo.) as the substrate. β-Hexosaminidase A activity was assayed using 4-methylumbelliferyl-6-sulfo-2-acetamido-2-deoxy-β-D-glucopyranoside (4-MUGS; Calbiochem, San Diego, Calif.). β-Hexosaminidase B activity was determined by subtracting β-Hexosaminidase A activity from total Hexosaminidase activity (Yamaguchi et al., 2003). Enzyme activity is expressed as nmol/mg protein/hr.

Histological analysis of GFP expression in ROSA-GFP mice. For GFP expression analysis, nervous tissues were directly observed under fluorescent microscope after dissections. The 10 μm cryo sections were prepared from DRG and mounted with VECTASHIELD mounting medium with DAPI (Vector Laboratories).

Histological analysis of hexb−/− mice. Mice were perfused transcardially with cold saline followed by 4% paraformaldehyde, 0.05% glutaraldehyde, 0.5% picric acid and 0.01 M phosphate buffer (pH 7.4) solution. L1-5 DRG tissues were removed and 10-μm thick cryosections were incubated with goat anti-hexb antibody (1:100, Santa Cruz Biotechnology) overnight at 4° C. Next day, the sections were incubated with rhodamine labeled donkey anti-goat IgG and mounted with VECTASHIELD mounting medium with DAPI (Vector Laboratories). Other sections from vector treated mice were also used for periodic acid schiff (PAS) (PAS staining system, Sigma) and Nissl stain with cresyl violet (Sigma). For enzymatic histochemical analysis of hexosaminidase, DRG were immersed in Baker fixative solution (4% paraformaldehyde, 1% anhydrous calcium chloride, pH7.2) for 1 h at 4° C., and then immersed into gum-sucrose solution (14% antiseptic thymol 100, 0.14% gum arabic, 1.25 M saccharose) for 24 h at 4° C. 10 μm cryosections were incubated in working solution containing 0.5 mM naphthol-AS-BI-D-N-acetyl-β-glucosaminide (Sigma) and 3.6 mM Fast Garnet GBC sulfate salt (Sigma) at pH 5.2 for 30 min at 37° C. and then counterstained with 1% methyl green for nuclei.

Electrophysiological studies and behavior tests. Nerve conduction studies (NCS) were performed with CADWELL SIERRA 6200A (Cadwell Laboratories) under anesthetization at 30° C.-32° C. temperature. Motor nerve conduction study was performed in the sciatic nerves as described previously (Terashima et al., 2005). For sensory nerve conduction studies, sural nerves were stimulated in the distal site at ankle joint level and were recorded in proximal site (Terashima et al., 2005). Adhesive removal tests were performed as neurological behavior tests. Small adhesive stimuli (Avery adhesive labels, one-quarter inch round) were placed on the hind-paw of the mouse, and the time to make contact and remove the sticker was recorded. To remove the stickers, animals would use both forelimbs toward their feet and swipe off the stimulus with both forepaws. Each mouse received three trials and had an inter-trial interval of at least 3 min. All testing was performed in the animal's home cage (Fleming et al., 2004).

Statistical analysis. All data are expressed as means±S.D. All in vitro experiments were performed in triplicate in at least three independent experiments. In vivo analyses were performed using five mice/group unless specified. The Student's unpaired two tailed t-test was used to calculate statistical significance. Data were considered significant at p<0.05.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Sergeeva, M. G. Kolonin, J. J. Molldrem, R. Pasqualini, W. Arap, Display technologies: application for the discovery of drug and gene delivery agents, Adv. Drug Deliv. Rev. 58 (2006) 1622-1654.

Sghirlanzoni, D. Pareyson, G. Lauria, Sensory neuron diseases, Lancet Neurol. 4 (2005) 349-361.

Bergelson, J. M. et al. Isolation of a common receptor for Coxsackie B viruses and adenoviruses 2 and 5. *Science* 275, 1320-3 (1997).

Biermann, V. et al. Targeting of high-capacity adenoviral vectors. *Hum Gene Ther* 12, 1757-69 (2001).

Brunetti-Pierri, N. & Ng, P. Progress and prospects: gene therapy for genetic diseases with helper-dependent adenoviral vectors. *Gene Ther* 15, 553-60 (2008).

Butti, E. et al. Absence of an intrathecal immune reaction to a helper-dependent adenoviral vector delivered into the cerebrospinal fluid of non-human primates. *Gene Ther* 15, 233-8 (2008).

Chattopadhyay, M. et al. HSV-mediated gene transfer of vascular endothelial growth factor to dorsal root ganglia prevents diabetic neuropathy. *Gene Ther* 12, 1377-84 (2005).

Chiocca, E. A. et al. A phase I trial of Ad.hIFN-beta gene therapy for glioma. *Mol Ther* 16, 618-26 (2008).

Sah, D. W. Therapeutic potential of RNA interference for neurological disorders, Life Sci. 79 (2006) 1773-1780.

Dechecchi, M. C. et al. Heparan sulfate glycosaminoglycans are receptors sufficient to mediate the initial binding of adenovirus types 2 and 5. *J Virol* 75, 8772-80 (2001).

Driesse, M. J. et al. Intra-CSF administered recombinant adenovirus causes an immune response-mediated toxicity. *Gene Ther* 7, 1401-9 (2000).

Du, S.-L., Pan, H., Lu, W.-Y., Wang, J., Wu, J., Wang, J.-Y. Cyclic Arg-Gly-Asp Peptide-Labeled Liposomes for Targeting Drug Therapy of Hepatic Fibrosis in Rats. J. Pharmacol. Exper. Ther. 322 (2), 560-568 (2007).

Erturk, E. et al. Binding of CCAAT displacement protein CDP to adenovirus packaging sequences. *J. Virol.* 77, 6255-6264. (2003)

Marmigere, F., P. Ernfors, Specification and connectivity of neuronal subtypes in the sensory lineage, Nat. Rev. Neurosci. 8 (2007) 114-127.

Hong, F. D., G. L. Clayman, Isolation of a peptide for targeted drug delivery into human head and neck solid tumors, Cancer Res. 60 (2000) 6551-6556.

Fechner, H. et al. Expression of coxsackie adenovirus receptor and alphav-integrin does not correlate with adenovector targeting in vivo indicating anatomical vector barriers. *Gene Ther* 6, 1520-35 (1999).

Fleming, S. M. et al. Early and progressive sensorimotor anomalies in mice overexpressing wild-type human alpha-synuclein. *J Neurosci* 24, 9434-40 (2004).

Glatzel, M. et al. Adenoviral and adeno-associated viral transfer of genes to the peripheral nervous system. *Proc Natl Acad Sci USA* 97, 442-7 (2000).

Kato, H., S. Chen, H, Kiyama, K, Ikeda, N. Kimura, K. Nakashima, T. Taga, Identification of a novel WD repeat-containing gene predominantly expressed in developing and regenerating neurons, J. Biochem. (Tokyo) 128 (2000) 923-932.

Hotta, Y., Honda, T., Naito, M. & Kuwano, R. Developmental distribution of coxsackie virus and adenovirus receptor localized in the nervous system. *Brain Res Dev Brain Res* 143, 1-13 (2003).

Dodd, J., T M. Jessell, Lactoseries carbohydrates specify subsets of dorsal root ganglion neurons projecting to the superficial dorsal horn of rat spinal cord, J. Neurosci. 5 (1985) 3278-3294.

Liu, J. K., Q. Teng, M. Garrity-Moses, T. Federici, D. Tanase, M. J. Imperiale, N. M. Boulis, A novel peptide defined through phage display for therapeutic protein and vector neuronal targeting, Neurobiol. Dis. 19 (2005) 407-418.

Goss, J. R. The therapeutic potential of gene transfer for the treatment of peripheral neuropathies, Expert Rev. Mol. Med. 9 (2007) 1-20.

Mendell, J. R., Z. Sahenk, Clinical practice. Painful sensory neuropathy, N. Engl. J. Med. 348 (2003) 1243-1255.

Jackson, C. A., Messinger, J., Palmer, M. T., Peduzzi, J. D. & Morrow, C. D. Gene expression in the muscle and central nervous system following intramuscular inoculation of encapsidated or naked poliovirus replicons. *Virology* 314, 45-61 (2003).

Kalyuzhniy, O. et al. Adenovirus serotype 5 hexon is critical for virus infection of hepatocytes in vivo. *Proc Natl Acad Sci USA* 105, 5483-8 (2008).

Kim, I. H., Jozkowicz, A., Piedra, P. A., Oka, K. & Chan, L. Lifetime correction of genetic deficiency in mice with a single injection of helper-dependent adenoviral vector. *Proc Natl Acad Sci USA* 98, 13282-7 (2001).

Koizumi, N. et al. Modified adenoviral vectors ablated for coxsackievirus-adenovirus receptor, alphav integrin, and heparan sulfate binding reduce in vivo tissue transduction and toxicity. *Hum Gene Ther* 17, 264-79 (2006).

Kritz, A. B. et al. Adenovirus 5 fibers mutated at the putative HSPG-binding site show restricted retargeting with targeting peptides in the HI loop. *Mol Ther* 15, 741-9 (2007).

Kuntzer, T., Antoine, J. C. & Steck, A. J. Clinical features and pathophysiological basis of sensory neuronopathies (ganglionopathies). *Muscle Nerve* 30, 255-68 (2004).

Mata, M., M. Chattopadhyay, D. J. Fink, Gene therapy for the treatment of sensory neuropathy, Expert Opin. Biol. Ther. 6 (2006) 499-507.

Kolonin, M. G., P. K. Saha, L. Chan, R. Pasqualini, W. Arap, Reversal of obesity by targeted ablation of adipose tissue, Nat. Med. 10 (2004) 625-632.

Malinow, K. et al. Subacute sensory neuronopathy secondary to dorsal root ganglionitis in primary Sjogren's syndrome. *Ann Neurol* 20, 535-7 (1986).

McCaffrey, A. P. et al. The host response to adenovirus, helper-dependent adenovirus, and adeno-associated virus in mouse liver. *Mol Ther* 16, 931-41 (2008).

McGuire, M. J., Sykes, K. F., et al. A Library-Selected, Langerhans Cell-Targeting Peptide Enhances an Immune Response. DNA and Cell Biol. 23 (11), 742-752.

Mizuguchi, H. & Hayakawa, T. Targeted adenovirus vectors. *Hum Gene Ther* 15, 1034-44 (2004).

Montpetit, V. J., Clapin, D. F., Tryphonas, L. & Dancea, S. Alteration of neuronal cytoskeletal organization in dorsal root ganglia associated with pyridoxine neurotoxicity. *Acta Neuropathol* 76, 71-81 (1988).

Morral, N. et al. Administration of helper-dependent adenoviral vectors and sequential delivery of different vector serotype for long-term liver-directed gene transfer in baboons. *Proc Natl Acad Sci USA* 96, 12816-21 (1999).

Muruve, D. A. et al. Helper-dependent adenovirus vectors elicit intact innate but attenuated adaptive host immune responses in vivo. J Virol 78, 5966-72 (2004).

Adey, N. B, A. H. Mataragnon, J. E. Rider, J. M. Carter, B. K. Kay, Characterization of phage that bind plastic from phage-displayed random peptide libraries, Gene 156 (1995) 27-31.

Petty, N. K., T. J. Evans, P. C. Fineran, G. P. Salmond, Biotechnological exploitation of bacteriophage research, Trends Biotechnol. 25 (2007) 7-15.

Oi, J. et al. Isolation of specific peptides that home to dorsal root ganglion neurons in mice. *Neurosci Lett* 434, 266-72 (2008).

Oka, K. & Chan, L. Helper-Dependent Adenoviral Vectors. in *Current Protocols in Molecular Biology* 16.24.1-16.24.23 (John Wiley & Sons, Inc., Hoboken, N.J., 2005).

Oka, K. et al. Long-term stable correction of low-density lipoprotein receptor-deficient mice with a helper-dependent adenoviral vector expressing the very low-density lipoprotein receptor. *Circulation* 103, 1274-81 (2001).

Parker, A. L. et al. Multiple vitamin K-dependent coagulation zymogens promote adenovirus-mediated gene delivery to hepatocytes. *Blood* 108, 2554-61 (2006).

Pezet, S. et al. Reversal of neurochemical changes and pain-related behavior in a model of neuropathic pain using modified lentiviral vectors expressing GDNF. *Mol Ther* 13, 1101-9 (2006).

de Vega, S., T. Iwamoto, T. Nakamura, K. Hozumi, D. A. McKnight, L. W. Fisher, S. Fukumoto, Y. Yamada, TM14 is a new member of the fibulin family (fibulin-7) that interacts with extracellular matrix molecules and is active for cell binding, J. Biol. Chem. Epub ahead of print (2007) PMID: 17699513 [PubMed—as supplied by publisher].

Kusunoki, S., K. Inoue, M. Iwamori, Y. Nagai, T. Mannen, Fucosylated glycoconjugates in human dorsal root ganglion cells with unmyelinated axons, Neurosci. Lett. 126 (1991) 159-162.

Liang, S., T. Lin, J. Ding, Y. Pan, D. Dang, C. Guo, M. Zhi, P. Zhao, L. Sun, L. Hong, Y. Shi, L. Yao, J. Liu, K. Wu, D. Fan, Screening and identification of vascular-endothelial-cell-specific binding peptide in gastric cancer, J. Mol. Med. 84 (2006) 764-773.

Nicklin, S. A., S. J. White, S. J. Watkins, R. E. Hawkins, A. H. Baker, Selective targeting of gene transfer to vascular endothelial cells by use of peptides isolated by phage display, Circulation 102 (2000) 231-237.

White, S. J., S. A. Nicklin, H. Buning, M. J. Brosnan, K. Leike, E. D. Papadakis, M. Hallek, A. H. Baker, Targeted gene delivery to vascular tissue in vivo by tropism-modified adeno-associated virus vectors, Circulation 109 (2004) 513-519.

Lawson, S. N., Phenotype and function of somatic primary afferent nociceptive neurones with C-, Adelta- or Aalpha/beta-fibres, Exp. Physiol. 87 (2002) 239-244.

Lawson, S. N., P. J. Waddell, Soma neurofilament immunoreactivity is related to cell size and fibre conduction velocity in rat primary sensory neurons, J. Physiol. 435 (1991) 41-63.

Sidhu, S. S., Engineering M13 for phage display, Biomol. Eng. 18 (2001) 57-63.

Sadosky, A., McDermott, A. M., Brandenburg, N. A. & Strauss, M. A review of the epidemiology of painful diabetic peripheral neuropathy, postherpetic neuralgia, and less commonly studied neuropathic pain conditions. *Pain Pract* 8, 45-56 (2008).

Sango, K. et al. Mouse models of Tay-Sachs and Sandhoff diseases differ in neurologic phenotype and ganglioside metabolism. *Nat Genet* 11, 170-6 (1995).

Sango, K., Yamanaka, S., Ajiki, K., Tokashiki, A. & Watabe, K. Lysosomal storage results in impaired survival but normal neurite outgrowth in dorsal root ganglion neurones from a mouse model of Sandhoff disease. *Neuropathol Appl Neurobiol* 28, 23-34 (2002).

Seiler, M. P., Cerullo, V. & Lee, B. Immune response to helper dependent adenoviral mediated liver gene therapy: challenges and prospects. *Curr Gene Ther* 7, 297-305 (2007).

Sghirlanzoni, A., Pareyson, D. & Lauria, G. Sensory neuron diseases. *Lancet Neurol* 4, 349-61 (2005).

Shayakhmetov, D. M., Gaggar, A., Ni, S., Li, Z. Y. & Lieber, A. Adenovirus binding to blood factors results in liver cell infection and hepatotoxicity. *J Virol* 79, 7478-91 (2005).

Shayakhmetov, D. M., Eberly, A. M., Li, Z. Y. & Lieber, A. Deletion of penton RGD motifs affects the efficiency of both the internalization and the endosome escape of viral particles containing adenovirus serotype 5 or 35 fiber knobs. *J Virol* 79, 1053-61 (2005).

Siniscalco, D., de Novellis, V., Rossi, F., Maione, S. Neuropathic pain: Is the End of Suffering Starting in the Gene Therapy? Current Drug Targets 6, 75-80 (2005).

Storek, B., Reinhardt, M., Wang, C., Janssen, W. G. M., Harder, N. M., Banck, M. S., Morrison, J. H., and Beutler, A. S. Sensory neuron targeting by self-complementary AAV8 via lumbar puncture for chronic pain. Proc. Natl Acad. Sci. 105(3), 1055-1060 (2008).

Sutton, R. E., Wu, H. T., Rigg, R., Bohnlein, E. & Brown, P. O. Human immunodeficiency virus type 1 vectors efficiently transduce human hematopoietic stem cells. *J Virol* 72, 5781-8 (1998).

Swanson, A. G., Buchan, G. C. & Alvord, E. C., Jr. Anatomic Changes in Congenital Insensitivity to Pain. Absence of Small Primary Sensory Neurons in Ganglia, Roots, and Lissauer's Tract. *Arch Neurol* 12, 12-8 (1965).

Terashima, T., H. Kojima, M. Fujimiya, K. Matsumura, J. Oi, M. Hara, A. Kashiwagi, H. Kimura, H. Yasuda, L. Chan, The fusion of bone-marrow-derived proinsulin-expressing cells with nerve cells underlies diabetic neuropathy, Proc. Natl. Acad. Sci. U.S.A. 102 (2005) 12525-12530.

Price, T. J., C. M. Flores, Critical evaluation of the colocalization between calcitonin gene-related peptide, substance P, transient receptor potential vanilloid subfamily type 1 immunoreactivities, and isolectin B4 binding in primary afferent neurons of the rat and mouse, J. Pain 8 (2007) 263-272.

Terashima, T. et al. The fusion of bone-marrow-derived pro-insulin-expressing cells with nerve cells underlies diabetic neuropathy. *Proc Natl Acad Sci USA* 102, 12525-30 (2005).

Tolcher, A. W. et al. Phase I, pharmacokinetic, and pharmacodynamic study of intravenously administered Ad5CMV-p53, an adenoviral vector containing the wild-type p53 gene, in patients with advanced cancer. *J Clin Oncol* 24, 2052-8 (2006).

Tomko, R. P., Xu, R. & Philipson, L. HCAR and MCAR: the human and mouse cellular receptors for subgroup C adenoviruses and group B coxsackieviruses. *Proc Natl Acad Sci USA* 94, 3352-6 (1997).

Arap, W., M. G. Kolonin, M. Trepel, J. Landenranta, M. Cardo-Vila, R. J. Giordano, P. J. Mintz, P. U. Ardelt, V. J. Yao, C. I. Vidal, L. Chen, A. Flamm, H. Valtanen, L. M. Weavind, M. E. Hicks, R. E. Pollock, G. H. Botz, C. D. Bucana, E. Koivunen, D. Cahill, P. Troncoso, K. A. Baggerly, R. D. Pentz, K. A. Do, J. Logothetis, R. Pasqualini, Steps toward mapping the human vasculature by phage display, Nat. Med. 8 (2002) 121-127.

Waddington, S. N. et al. Adenovirus serotype 5 hexon mediates liver gene transfer. *Cell* 132, 397-409 (2008).

Waehler, R., Russell, S. J. & Curiel, D. T. Engineering targeted viral vectors for gene therapy. *Nat Rev Genet* 8, 573-87 (2007).

Wang, X. et al. Gene transfer to dorsal root ganglia by intrathecal injection: effects on regeneration of peripheral nerves. *Mol Ther* 12, 314-20 (2005).

Wang, H. et al. A capsid-modified helper-dependent adenovirus vector containing the beta-globin locus control region displays a nonrandom integration pattern and allows stable, erythroid-specific gene expression. *J Virol* 79, 10999-1013 (2005).

Wang, X., Wang, C., Zeng, J., Xu, X., Hwang, P. Y. K., Yee, W.-C., Ng, Y.-K., Wang, S. Gene Transfer to Dorsal Root Ganglia by Intrathecal Injection: Effects on Regeneration of Peripheral Nerves. Molec. Ther. 12(2), 314-320 (2005).

Wanschitz, J., Hainfellner, J. A., Kristoferitsch, W., Drlicek, M. & Budka, H. Ganglionitis in paraneoplastic subacute sensory neuronopathy: a morphologic study. *Neurology* 49, 1156-9 (1997).

Wickham, T. J., Mathias, P., Cheresh, D. A. & Nemerow, G. R. Integrins alpha v beta 3 and alpha v beta 5 promote adenovirus internalization but not virus attachment. *Cell* 73, 309-19 (1993).

Zhang, X., L. Bao, The development and modulation of nociceptive circuitry, Curr. Opin. Neurobiol. 16 (2006) 460-466.

Xu, Y., Gu, Y., Wu, P., Li, G. W. & Huang, L. Y. Efficiencies of transgene expression in nociceptive neurons through different routes of delivery of adeno-associated viral vectors. *Hum Gene Ther* 14, 897-906 (2003).

Yamaguchi, A. et al. Plasmid-based gene transfer ameliorates visceral storage in a mouse model of Sandhoff disease. *J Mol Med* 81, 185-93 (2003).

Yasuda, H. et al. Diabetic neuropathy and nerve regeneration. *Prog Neurobiol* 69, 229-85 (2003).

Although the present invention and its advantages have been described in detail, it should be understood that various changes, substitutions and alterations can be made herein without departing from the invention as defined by the appended claims. Moreover, the scope of the present appli-

What is claimed is:

1. An isolated peptide of SEQ ID NO:2.

2. The peptide of claim 1, comprised in a pharmaceutically acceptable excipient.

3. The peptide of claim 1, linked to a protein or a liposome.

4. The peptide of claim 3, wherein the protein is a therapeutic protein.

5. The peptide of claim 4, wherein the therapeutic protein is NGF, EGF, FGF, BDNF, IGF1, CTNF, PDNF, VAD, DEVD, NGN1, NGN2, NGN3, RUNX3, or a signal peptide.

6. The peptide of claim 3, wherein the protein is present on the surface of a helper-dependent adenoviral particle.

7. The peptide of claim 6, wherein the particle is defined as further comprising a therapeutic polynucleotide.

8. The peptide of claim 7, wherein the therapeutic polynucleotide is selected from the group consisting of NGF, EGF, FGF, BDNF, IGF1, CTNF, PDNF, VAD, DEVD, NGN1, NGN2, NGN3, RUNX3, IL-10, anti-TNFα, EPO, or prepro-β endorphin.

9. A polynucleotide encoding the peptide of SEQ ID NO:2.

* * * * *

SEQUENCE LISTING

<160> NUMBER OF SEQ ID NOS: 114

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Ser Pro Gly Ala Arg Ala Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Asp Gly Pro Trp Arg Lys Met
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Phe Gly Gln Lys Ala Ser Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Thr Gly Phe Gln Ser Gly Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Asp Ser Ser Arg Thr Arg Leu
1               5

<210> SEQ ID NO 6
<211> LENGTH: 7
<212> TYPE: PRT

```
<213> ORGANISM: Artificial Sequence
<220> FEATURE:
<223> OTHER INFORMATION: Synthetic Peptide

<400> SEQUENCE: 6

Asp Phe Ile Arg Thr Gln Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Leu Lys His Thr Asn Glu Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Gln Gly Ala His Asn Asn Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Asn Pro His Lys Ala Pro Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Asn Pro Ser Leu Gln Ala Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Pro Pro Trp Ser Ser Pro Lys
1               5

<210> SEQ ID NO 12
<211> LENGTH: 7
<212> TYPE: PRT
<213> ORGANISM: Artificial Sequence
```

```
<220> FEATURE:
<223> OTHER INFORMATION: Synthetic Peptide

<400> SEQUENCE: 12

Ala Gln Ser His Asn Lys Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Leu Pro Thr Ser Lys Lys Met
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Asn His Leu Lys Asn Pro Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Thr Phe Ser Ile Gly Glu Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 16

Gln Ala Ile Gln Asn Ser Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 17

His Asn Thr Asn Ala Gln His
1               5

<210> SEQ ID NO 18
<211> LENGTH: 7
<212> TYPE: PRT
<213> ORGANISM: Artificial Sequence
<220> FEATURE:
```

```
<223> OTHER INFORMATION: Synthetic Peptide

<400> SEQUENCE: 18

Thr Pro Ser Leu Pro Gln Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Asn Met Pro Thr Gln Arg Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 20

Pro Val Arg Ser Pro Ala Val
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

Ser Ser Gln Ala Pro Gln Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 22

Asp Ala Gln Lys Asn Met Asn
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 23

Gly Leu Gln Leu Ser Gln Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Peptide
```

```
<400> SEQUENCE: 24

Ser Ala Ser Asn Thr Gln Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 25

Glu Gly His Leu Val Ser Gln
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 26

Ser Asp Pro Gly Asn Tyr Met
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 27

Ala Leu Asp Asn Val Pro His
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 28

Pro Thr Lys Gln His Ala Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 29

Thr Glu Leu Gln Arg His Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Peptide
```

```
<400> SEQUENCE: 30

His Thr Thr Ser Ser Leu Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 31

Met Gly Gln Asn Leu Arg Phe
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 32

Asn Leu Gln Leu Ala Pro Asp
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 33

Ser Ser Phe Arg Gly Ala Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 34

Leu His Lys Ser His Leu Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 35

Ala Pro Pro Glu Leu Arg Leu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 36
```

His Arg Thr Ile Ala Ser Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 37

Thr Glu Ser Ile Gly Asp Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 38

Ala Pro Asp Glu Thr Glu Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 39

Lys Gly Leu Pro Pro Gly His
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 40

Pro Ser Gly Thr Pro Ser Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 41

Ser Asn Arg Ser Pro Leu Met
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 42

```
Thr Ile Gly Gln Ser Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 43

Ser Pro Thr Glu Gly Thr Pro
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 44

Pro Leu Ser Gly Ala Pro Trp
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 45

Asp Ala Pro Thr His Met His
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 46

Thr Asp Phe Arg Ser Arg Val
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 47

Leu Val Leu Pro Pro Leu Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 48

Ser Ser Ser Pro Ala Arg Leu
```

```
1               5
```

<210> SEQ ID NO 49
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 49

```
Thr Ala Thr Asn Thr Arg Thr
1               5
```

<210> SEQ ID NO 50
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 50

```
Asp Gly Ala Gly Thr Trp Val
1               5
```

<210> SEQ ID NO 51
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 51

```
Glu Lys His Leu Ala Pro Arg
1               5
```

<210> SEQ ID NO 52
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 52

```
Pro Leu Thr Pro Leu Gly Phe
1               5
```

<210> SEQ ID NO 53
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 53

```
Met Thr Pro Phe Met Gly Ser
1               5
```

<210> SEQ ID NO 54
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 54

```
Asp Ser Pro Gly Trp Pro His
1               5
```

```
<210> SEQ ID NO 55
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 55

Gly Glu Arg His Ser Leu Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 56

Thr Thr Ala Val Ala Leu Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 57

Asn Gly Leu His Val Gln Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 58

Thr Leu Ser Pro Arg Ser Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 59

His Thr Gly Pro Phe Gly Leu
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 60

Leu Ser Thr Ser Ser Lys Lys
1               5
```

<210> SEQ ID NO 61
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 61

Thr Pro Pro Ser Pro Arg Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 62

Pro Ala Leu Ser His Ser Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 63

Thr Pro Ser Trp Ser Lys Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 64

Ser Thr Pro Ala Val Pro Pro
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 65

Asn Leu Asn Ala His His Lys
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 66

Gln His Gln Lys Gln Gly Tyr
1               5

-continued

```
<210> SEQ ID NO 67
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 67

Asn Lys Thr Thr Asn Ile Met
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 68

Thr Ser Ala Ser Leu Ser Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 69

Arg Ser Ser Pro Pro Asn Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 70

Ser Pro Pro Arg Pro Thr Gly
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 71

Val Asn Thr Pro Glu Arg His
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 72

Thr Pro Gln Tyr Pro Lys Leu
1               5

<210> SEQ ID NO 73
```

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 73

Pro Thr Leu Leu Pro His Gln
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 74

Asn Asn Ala Asn Tyr Arg Leu
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 75

Gly Pro His Phe His Gln Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 76

Pro Ala Met Asn Ser Val Lys
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 77

Gly Thr Thr Pro Thr Ser Thr
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 78

His Asn Ser Thr Arg Gly Ser
1               5

<210> SEQ ID NO 79
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 79

Asp Asp Ser Gly Pro Leu Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 80

Asn Met His Pro Thr Ala Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 81

His Gln Asn Trp Arg His Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 82

Pro Ser Thr Lys Tyr His Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 83

Pro Leu Arg Leu Ala His Gln
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 84

Gln Met Pro Gly Asn Asn Leu
1               5

<210> SEQ ID NO 85
<211> LENGTH: 7
<212> TYPE: PRT
```

<213> ORGANISM: Artificial Sequence
<220> FEATURE:
<223> OTHER INFORMATION: Synthetic Peptide

<400> SEQUENCE: 85

Leu Ala Thr Pro Leu Arg Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 86

Leu Asn Gly Leu Lys Ala Ala
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 87

Thr Val Ser Ser His Arg Ala
1               5

<210> SEQ ID NO 88
<211> LENGTH: 32
<212> TYPE: DNA
<213> ORGANISM: Artificial Sequence
<220> FEATURE:
<223> OTHER INFORMATION: Synthetic Primer

<400> SEQUENCE: 88
ggatccgcca ccatgaagcg cgcaagaccg tc                             32

<210> SEQ ID NO 89
<211> LENGTH: 28
<212> TYPE: DNA
<213> ORGANISM: Artificial Sequence
<220> FEATURE:
<223> OTHER INFORMATION: Synthetic Primer

<400> SEQUENCE: 89
gcggccgctt attcttgggc aatgtatg                                 28

<210> SEQ ID NO 90
<211> LENGTH: 38
<212> TYPE: DNA
<213> ORGANISM: Artificial Sequence
<220> FEATURE:
<223> OTHER INFORMATION: Synthetic Primer

<400> SEQUENCE: 90
ttaattaagc caccatgtcc aatttactga ccgtacac                      38

<210> SEQ ID NO 91
<211> LENGTH: 29
<212> TYPE: DNA
<213> ORGANISM: Artificial Sequence
<220> FEATURE:
<223> OTHER INFORMATION: Synthetic Primer

<400> SEQUENCE: 91
gcggccgcct aatcgccatc ttccagcag					29

<210> SEQ ID NO 92
<211> LENGTH: 19
<212> TYPE: DNA
<213> ORGANISM: Artificial Sequence
<220> FEATURE:
<223> OTHER INFORMATION: Synthetic Primer

<400> SEQUENCE: 92
atgccgcagt ccccgcgta					19

<210> SEQ ID NO 93
<211> LENGTH: 23
<212> TYPE: DNA
<213> ORGANISM: Artificial Sequence
<220> FEATURE:
<223> OTHER INFORMATION: Synthetic Primer

<400> SEQUENCE: 93
ctggaatgct gtagacgtct gtc					23

<210> SEQ ID NO 94
<211> LENGTH: 30
<212> TYPE: DNA
<213> ORGANISM: Artificial Sequence
<220> FEATURE:
<223> OTHER INFORMATION: Synthetic Primer

<400> SEQUENCE: 94
gttgcagtgc acggcagata cacttgctga					30

<210> SEQ ID NO 95
<211> LENGTH: 28
<212> TYPE: DNA
<213> ORGANISM: Artificial Sequence
<220> FEATURE:
<223> OTHER INFORMATION: Synthetic Primer

<400> SEQUENCE: 95
gccactggtg ggccataatt caattcgc					28

<210> SEQ ID NO 96
<211> LENGTH: 30
<212> TYPE: DNA
<213> ORGANISM: Artificial Sequence
<220> FEATURE:
<223> OTHER INFORMATION: Synthetic Primer

<400> SEQUENCE: 96
gcattaccgg tcgatgcaac gagtgatgag					30

<210> SEQ ID NO 97
<211> LENGTH: 30
<212> TYPE: DNA
<213> ORGANISM: Artificial Sequence
<220> FEATURE:
<223> OTHER INFORMATION: Synthetic Primer

<400> SEQUENCE: 97
gagtgaacga acctggtcga aatcagtgcg					30

<210> SEQ ID NO 98
<211> LENGTH: 26

<212> TYPE: DNA
<213> ORGANISM: Artificial Sequence
<220> FEATURE:
<223> OTHER INFORMATION: Synthetic Primer

<400> SEQUENCE: 98
gcacgacttc ttcaagtccg ccatgc                                26

<210> SEQ ID NO 99
<211> LENGTH: 27
<212> TYPE: DNA
<213> ORGANISM: Artificial Sequence
<220> FEATURE:
<223> OTHER INFORMATION: Synthetic Primer

<400> SEQUENCE: 99
gcggatcttg aagttcacct tgatgcc                               27

<210> SEQ ID NO 100
<211> LENGTH: 21
<212> TYPE: DNA
<213> ORGANISM: Artificial Sequence
<220> FEATURE:
<223> OTHER INFORMATION: Synthetic Primer

<400> SEQUENCE: 100
acagttgcag aagctcctgg t                                     21

<210> SEQ ID NO 101
<211> LENGTH: 22
<212> TYPE: DNA
<213> ORGANISM: Artificial Sequence
<220> FEATURE:
<223> OTHER INFORMATION: Synthetic Primer

<400> SEQUENCE: 101
cctctatgag ggaatcttgg ag                                    22

<210> SEQ ID NO 102
<211> LENGTH: 20
<212> TYPE: DNA
<213> ORGANISM: Artificial Sequence
<220> FEATURE:
<223> OTHER INFORMATION: Synthetic Primer

<400> SEQUENCE: 102
gacggccagg tcatcactat                                       20

<210> SEQ ID NO 103
<211> LENGTH: 20
<212> TYPE: DNA
<213> ORGANISM: Artificial Sequence
<220> FEATURE:
<223> OTHER INFORMATION: Synthetic Primer

<400> SEQUENCE: 103
cttctgcatc ctgtcagcaa                                       20

<210> SEQ ID NO 104
<211> LENGTH: 12
<212> TYPE: DNA
<213> ORGANISM: Artificial Sequence
<220> FEATURE:
<223> OTHER INFORMATION: Synthetic Primer

<400> SEQUENCE: 104

```
aaaaaaacca ag                                                    12
```

<210> SEQ ID NO 105
<211> LENGTH: 12
<212> TYPE: DNA
<213> ORGANISM: Artificial Sequence
<220> FEATURE:
<223> OTHER INFORMATION: Synthetic Primer

<400> SEQUENCE: 105

```
ggcgccggcg cc                                                    12
```

<210> SEQ ID NO 106
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 106

Gly Gly Ser Gly Gly Gly
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 107

Cys Ser Pro Gly Ala Arg Ala Phe Cys
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 108

Cys Asp Gly Pro Trp Arg Lys Met Cys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 109

Cys Phe Gly Gln Lys Ala Ser Ser Cys
1               5

<210> SEQ ID NO 110
<211> LENGTH: 24
<212> TYPE: DNA
<213> ORGANISM: Artificial Sequence
<220> FEATURE:
<223> OTHER INFORMATION: Synthetic Primer

<400> SEQUENCE: 110

```
acaggaggtt ccggaggtgg agga                                       24
```

```
<210> SEQ ID NO 111
<211> LENGTH: 31
<212> TYPE: DNA
<213> ORGANISM: Artificial Sequence
<220> FEATURE:
<223> OTHER INFORMATION: Synthetic Primer

<400> SEQUENCE: 111
gaaacaggag gttccggagg tggaggagac a                              31

<210> SEQ ID NO 112
<211> LENGTH: 63
<212> TYPE: DNA
<213> ORGANISM: Artificial Sequence
<220> FEATURE:
<223> OTHER INFORMATION: Synthetic Primer

<400> SEQUENCE: 112
gaaacaggag gttccggatg ctcgccgggg gcgcgtgctt tttgcgccgg aggtggagga    60
gac                                                                 63

<210> SEQ ID NO 113
<211> LENGTH: 63
<212> TYPE: DNA
<213> ORGANISM: Artificial Sequence
<220> FEATURE:
<223> OTHER INFORMATION: Synthetic Primer

<400> SEQUENCE: 113
gaaacaggag gttccggatg cgatggtccg tggcgtaaga tgtgcgccgg aggtggagga    60
gac                                                                 63

<210> SEQ ID NO 114
<211> LENGTH: 63
<212> TYPE: DNA
<213> ORGANISM: Artificial Sequence
<220> FEATURE:
<223> OTHER INFORMATION: Synthetic Primer

<400> SEQUENCE: 114
gaaacaggag gttccggatg ctttgggcag aaggcgtctt cttgcgccgg aggtggagga    60
gac                                                                 63
```